United States Patent
Allen et al.

(10) Patent No.: US 8,138,181 B2
(45) Date of Patent: Mar. 20, 2012

(54) IMIDAZO[1,2-A]PYRIDINE COMPOUNDS AS RECEPTOR TYROSINE KINASE INHIBITORS

(75) Inventors: Shelley Allen, Loveland, CO (US); Julie Marie Greschuk, Erie, CO (US); Nicholas C. Kallan, Boulder, CO (US); Fredrik P. Marmsäter, Boulder, CO (US); Mark C. Munson, Louisville, CO (US); James P. Rizzi, Longmont, CO (US); John E. Robinson, Commerce City, CO (US); Stephen T. Schlachter, Boulder, CO (US); George T. Topalov, Superior, CO (US); Qian Zhao, Superior, CO (US); Joseph P. Lyssikatos, Piedmont, CA (US)

(73) Assignee: Array BioPharma Inc., Boulder, CO (US)

( * ) Notice: Subject to any disclaimer, the term of this patent is extended or adjusted under 35 U.S.C. 154(b) by 410 days.

(21) Appl. No.: 12/593,879

(22) PCT Filed: Mar. 27, 2008

(86) PCT No.: PCT/US2008/058395
§ 371 (c)(1),
(2), (4) Date: Sep. 29, 2009

(87) PCT Pub. No.: WO2008/124323
PCT Pub. Date: Oct. 16, 2008

(65) Prior Publication Data
US 2010/0029633 A1      Feb. 4, 2010

Related U.S. Application Data

(60) Provisional application No. 60/909,857, filed on Apr. 3, 2007.

(51) Int. Cl.
A61K 31/5386    (2006.01)
A61K 31/437     (2006.01)
A61K 31/506     (2006.01)
C07D 471/02     (2006.01)
C07D 401/14     (2006.01)
C07D 498/08     (2006.01)
A61P 35/04      (2006.01)

(52) U.S. Cl. .............. 514/230.5; 514/300; 514/256; 546/121; 544/333; 544/105

(58) Field of Classification Search .......... 514/230.5, 514/300, 256; 546/121; 544/333, 105
See application file for complete search history.

(56) References Cited

U.S. PATENT DOCUMENTS

2005/0256309 A1    11/2005   Altenbach et al.
2011/0184013 A1*    7/2011   Allen et al. .......... 514/300

FOREIGN PATENT DOCUMENTS

| EP | 1277754 B1 | 1/2003 |
| WO | 0140217 A1 | 6/2001 |
| WO | 0183481 A1 | 11/2001 |
| WO | 02066477 A2 | 8/2002 |
| WO | 02088107 A1 | 11/2002 |
| WO | 03092595 A2 | 11/2003 |
| WO | 2004020431 A2 | 3/2004 |
| WO | 2004078110 A2 | 9/2004 |
| WO | 2006034402 A2 | 3/2006 |
| WO | 2006038111 A1 | 4/2006 |
| WO | 2007115289 A2 | 10/2007 |

OTHER PUBLICATIONS

Buckley, George M., Irak-4 inhibitors. Part II: A structure-based assessment of imidazo[1,2-a]pyridine binding, Bioorganic & Medicinal Chemistry Letters, vol. 18 (2008), pp. 3291-3295.
Buckley, George M., Irak-4 inhibitors. Part III: A series of imidazo[1,2-a]pyridines, Bioorganic & Medicinal Chemistry Letters, vol. 18 (2008), pp. 3656-3660.

* cited by examiner

*Primary Examiner* — Janet Andres
*Assistant Examiner* — Niloofar Rahmani
(74) *Attorney, Agent, or Firm* — John R. Moore; Sarah S. Mastous

(57) ABSTRACT

Compounds of Formula I: in which A, B, $R^1$, $R^{1a}$, $R^2$, $R^3$, $R^4$, $R^5$ $R^6$, $R^7$ and $R^8$ have the meanings given in the specification, are receptor tyrosine inhibitors useful in the treatment of diseases mediated by class 3 and class 5 receptor tyrosine kinases. Particular compounds of this invention have also been found to be inhibitors of Pim-1.

29 Claims, No Drawings

IMIDAZO[1,2-A]PYRIDINE COMPOUNDS AS RECEPTOR TYROSINE KINASE INHIBITORS

The present invention relates to novel compounds, to pharmaceutical compositions comprising the compounds, to a process for making the compounds and to the use of the compounds in therapy. More particularly, it relates to certain imidazopyridine compounds useful in the treatment and prevention of diseases mediated by class 3 and class 5 receptor tyrosine kinases. Particular compounds of this invention have also been found to be inhibitors of Pim-1.

Receptor tyrosine kinases (RTK's) include the class 3 receptor tyrosine kinases (PDGF-α, PDGFR-β, MCSF-1R, c-kit, and FLT3) and the class 5 receptor tyrosine kinases (VEGFR and KDR). It is known that such kinases are frequently aberrantly expressed in common human cancers, such as breast cancer, gastrointestinal cancer such as colon, rectal or stomach cancer, leukemia, and ovarian, bronchial or pancreatic cancer, renal cell carcinoma and gliomas.

FLT3 (fms-like tyrosine kinase; also known as Flk-2) is a member of the class 3 receptor tyrosine kinase (RTK) family, and is presumed to be involved in the hematopoietic system (Rosnet, et al., 1991, Genomics 9:380-385, Rosnet, et al., 1993, Blood 82:1110-1119). Aberrant expression of the FLT3 gene has been documented in both adult and childhood leukemias including acute myeloid leukemia (AML), AML with trilineage myelodysplasia (AML/TMDS), acute lymphoblastic leukemia (ALL), and myelodysplastic syndrome (MDS). Activating mutations of the FLT3 receptor have been found in about 35% of patients with acute myeloblastic leukemia (AML), and are associated with a poor prognosis. These types of mutations are associated with constitutive activation of the tyrosine kinase activity of FLT3, and result in proliferation and viability signals in the absence of ligand. Patients expressing the mutant form of the receptor have been shown to have a decreased chance for cure. In addition to activating mutations, ligand dependent (autocrine or paracrine) stimulation of over-expressed wild-type FLT3 contributes to AML. Thus, there is accumulating evidence for a role for hyperactivated (mutated) FLT3 kinase activity in human leukemias and myelodysplastic syndrome. FLT3 inhibitors may also be useful for treating immune related disorders and is involved in the process of angiogenesis through its expression in pericytes.

PDGFR is expressed on early stem cells, mast cells, myeloid cells, mesenchymal cells, and smooth muscles cells. PDGFR-β has been implicated in myeloid leukemias. Recently, it was shown that activating mutations in PDGFR-α kinase domain are in gastrointestinal stromal tumors (GIST) (Wong et al., 2007, Histopathology 51(6): 758-762).

In addition, blockade of PDGF signaling has been shown to reduce the development of fibrosis in various experimental models (Yoshiji et al., 2006, International Journal Molecular Medicine 17:899-904).

Accordingly, it has been recognized that inhibitors of receptor tyrosine kinases are useful as inhibitors of the growth of mammalian cancer cells or for treating immune related disorders.

The Pim kinases are a family of three distinct vertebrate protein serine/threonine kinases (Pim-1, -2 and -3) belonging to the calmodulin-dependent protein kinase-related (CAMK) group. The over-expression of Pim-1 has been reported in various human lymphomas and acute leukemias (Amson, R. et al, Proc. Natl. Acad. Sci. U.S.A., 1989, 86: 8857-8861). In addition, there is evidence that Pim-1 is over-expressed in prostatic neoplasia and human prostate cancer (Valdman, A. et al, The Prostate, 2004, 60: 367-371; Cibull, T. L. et al, J. Clin. Pathol., 2006, 59: 285-288) and may serve as a useful biomarker in identification of prostate cancer (Dhanasekaran, S. M. et al, Nature, 2001, 412(13): 822-826). Recently, it has been discovered that Pim-1 is up-regulated by Flt-3 and may play an ancillary role in Flt-3 mediated cell survival (Kim, K. T. et al Neoplasia, 2005, 105(4): 1759-1767). Since Flt-3 itself is implicated in leukemias like AML, additional knockdown of Pim-1 may be a useful approach to treating leukemias driven by Flt-3 or various mutations. Accordingly, Pim-1 inhibitors may be useful as therapeutic agents for a variety of cancers such as hematological cancers.

Tyrosine kinase inhibitors are known in the art. U.S. Pat. No. 7,125,888 describes certain imidazo[1,2-a]pyridine compounds substituted at the 3 position with a pyridyl, thiazolyl, oxazolyl or phenyl group and at the 7 position with an optionally substituted phenyl or pyridone group, which are purported to be tyrosine kinase inhibitors. U.S. patent publication 2005/0124637 discloses certain purine derivatives as inhibitors of receptor tyrosine kinases, including FLT3. PCT publication number WO 01/40217 and U.S. Pat. No. 7,019,147 disclose certain benzimidazole compounds having activity as tyrosine kinase inhibitors.

It has now been found that certain imidazo[1,2-a]pyridine compounds bearing a quinolinyl group at the 3 position of the imidazopyridine ring are inhibitors of receptor tyrosine kinases, in particular class 3 and class 5 receptor tyrosine kinases, which are useful for treating diseases mediated by class 3 and class 5 receptor tyrosine kinases, such as cancers, fibrosis, sclerosis, autoimmune disorders and scleroderma.

In certain embodiments, the imidazopyridine compounds are class 3 receptor tyrosine kinases inhibitors. In particular embodiments, the compounds are inhibitors of the class 3 receptor tyrosine kinases PDGFR and FLT3.

A subset of compounds of the imidazopyridine compounds disclosed herein are also inhibitors of the kinase PIM-1.

Accordingly, provided is a compound of general Formula I:

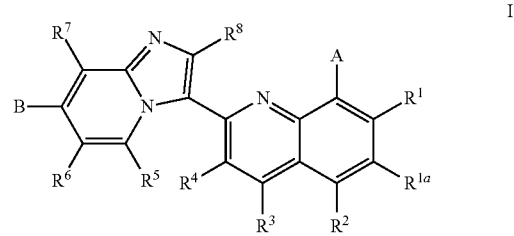

or a pharmaceutically acceptable salt thereof, wherein:
A is —Z—(CH$_2$)$_p$-(hetCyc$^{2a}$), —Z-(hetCyc$^{2b}$), Z—R$^{10}$ or Z—R$^{11}$;
Z is O or NH;
p is 0, 1, or 2;
hetCyc$^{2a}$ is a 5 or 6 membered heterocyclic ring optionally substituted with one or more R$^9$ groups;
hetCyc$^{2b}$ is a 7-12 membered spirocyclic or bridged heterobicyclic ring system optionally substituted with one or more R$^9$ groups;
R$^{10}$ is (1-6C)alkyl substituted with NR'R";
R$^{11}$ is (5-6C)cycloalkyl substituted with NR'R";
B is H, CN, OR$^h$, Ar$^1$, hetAr$^2$, C(O)NR'R$^j$, C(O)-hetCyc$^3$, C(O)NH(1-6C alkyl)-hetCyc$^3$, C(O)(1-6C alkyl)-hetCyc$^3$, SR$^k$, SO$_2$N(1-6C alkyl)$_2$, (1-6C alkyl)NR'R" or (1-3C)alkyl;
R$^1$, R$^{1a}$, R$^2$, R$^3$ and R$^4$ are independently H, F, Cl, CN, Me, Et, isopropyl, cyclopropyl, C(O)NR'R", CH$_2$OH, or hetAr$^3$;

$R^5$, $R^6$, $R^7$ and $R^8$ are independently H, F, Cl, CN or Me;

each $R^9$ is independently selected from halogen, CN, $CF_3$, (1-6C)alkyl, $NR^aR^b$, -(1-6C alkyl)$NR^aR^c$, $OR^a$, (1-6C alkyl)$OR^a$ [optionally substituted with amino], $C(O)NR^aR^c$, $C(O)(CR^xR^y)NR^aR^c$, $NHC(O)R^e$, $NHC(O)(CR^mR^n)NR^aR^c$, $NHC(O)NR^fR^g$, (1-6C alkyl)-hetAr$^1$, (1-6C alkyl)-hetCyc$^1$, oxo, and $C(O)_2$(1-6C alkyl);

each $R^a$ is independently H or (1-6C)alkyl;

each $R^b$ is independently H, (1-6C)alkyl, (1-6C alkyl)OH, (3-6C)cycloalkyl, $CH_2$hetAr$^4$, (1-6C fluoroalkyl) or -(1-6C alkyl)-O-(1-6C alkyl), each $R^c$ is independently H, (1-6C)alkyl, (3-6C)cycloalkyl, or aryl;

each $R^e$ is independently (1-6C alkyl);

each $R^f$ and $R^g$ is independently H or (1-6C)alkyl;

$R^h$ is H, $CF_3$, (1-6C)alkyl, (1-6Calkyl)-(3-6C cycloalkyl), (1-6C alkyl)-O-(1-6C alkyl), (1-6C alkyl)OH, (1-6C alkyl)-S-(1-6C alkyl), (1-6C alkyl)NR'R", hetCyc$^4$, (1-6C alkyl)hetCyc$^4$, (1-6C alkyl)aryl, or (1-6C alkyl)-hetAr$^5$;

$R^i$ is H or 1-6C alkyl;

$R^j$ is (1-6C)alkyl, (1-6C alkyl)-O-(1-6C alkyl), or (1-6C alkyl)-OH;

$R^k$ is (1-6C)alkyl, (3-6C)cycloalkyl, or (1-6C alkyl)-O-(1-6C alkyl);

$R^m$ and $R^n$ are independently H or (1-6C)alkyl;

$R^x$ and $R^y$ are independently H or (1-6C alkyl), or $R^x$ and $R^y$ together with the atom to which they are attached form a cyclopropyl ring;

Ar$^1$ is aryl optionally substituted with OH, O-(1-6C alkyl), $C(O)_2$(1-6C alkyl), or (1-6C alkyl)NR'R";

hetCyc$^1$ is a 5-6 membered heterocyclic ring which is optionally substituted with (1-6C)alkyl or OH;

hetCyc$^3$ and hetCyc$^4$ are independently a 5 or 6 membered heterocyclic ring optionally substituted with OH or —O(1-6C alkyl);

hetAr$^1$ and hetAr$^2$ are a 5-6 membered heteroaryl ring optionally substituted with one to three groups independently selected from (1-6C)alkyl, (3-6C)cycloalkyl, halogen, CN, $CF_3$, $OCH_2F$, $OCF_3$, O(1-6C alkyl), O(3-6C)cycloalkyl, and NR'R";

hetAr$^3$ and hetAr$^4$ are independently a 5-6 membered heteroaryl ring;

hetAr$^5$ is a 5-6 membered heteroaryl ring optionally substituted with (1-6C)alkyl; and R' and R" are independently H or (1-6C)alkyl.

Compounds of Formula I include compounds wherein:

A is —Z—$(CH_2)_p$-(hetCyc$^{2a}$), —Z-(hetCyc$^{2b}$), Z—R$^{10}$ or Z—R$^{11}$;

Z is O or NH;

p is 0, 1, or 2;

hetCyc$^{2a}$ is a 5 or 6 membered heterocyclic ring optionally substituted with one or more $R^9$ groups;

hetCyc$^{2b}$ is a 7-12 membered spirocyclic or bridged heterobicyclic ring system optionally substituted with one or more $R^9$ groups;

$R^{10}$ is (1-6C)alkyl substituted with NR'R";

$R^{11}$ is (5-6C)cycloalkyl substituted with NR'R";

B is H, CN, OR$^h$, Ar$^1$, hetAr$^2$, $C(O)NR^iR^j$, C(O)-hetCyc$^3$, C(O)(1-6C alkyl)-hetCyc$^3$, SR$^k$, $SO_2N$(1-6C alkyl)$_2$, or (1-6C alkyl)NR'R";

$R^1$, $R^{1a}$, $R^2$, $R^3$ and $R^4$ are independently H, F, Cl, CN, Me, Et, isopropyl, cyclopropyl, C(O)NR'R", $CH_2OH$, or hetAr$^3$;

$R^5$, $R^6$ and $R^7$ are independently H, F, Cl, CN or Me;

each $R^9$ is independently selected from halogen, CN, $CF_3$, (1-6C)alkyl, $NR^aR^b$, -(1-6C alkyl)$NR^aR^c$, $OR^a$, (1-6C alkyl)$OR^a$ [optionally substituted with amino], $C(O)NR^aR^c$, $C(O)(CR^xR^y)NR^aR^c$, $NHC(O)R^e$, $NHC(O)(CR^mR^n)NR^aR^c$, $NHC(O)NR^fR^g$, (1-6C alkyl)-hetAr$^1$, (1-6C alkyl)-hetCyc$^1$, oxo, and C(O)(1-6C alkyl);

$R^h$ is H, $CF_3$, (1-6C)alkyl, (1-6Calkyl)-(3-6C cycloalkyl), (1-6C alkyl)-O-(1-6C alkyl), (1-6C alkyl)OH, (1-6C alkyl)-S-(1-6C alkyl), (1-6C alkyl)NR'R", hetCyc$^4$, (1-6C alkyl)hetCyc$^4$, (1-6C alkyl)aryl, or (1-6C alkyl)-hetAr$^5$;

$R^i$ is H or 1-6C alkyl;

$R^j$ is (1-6C)alkyl, (1-6C alkyl)-O-(1-6C alkyl), or (1-6C alkyl)-OH;

$R^k$ is (1-6C)alkyl, (3-6C)cycloalkyl, or (1-6C alkyl)-O-(1-6C alkyl);

Ar$^1$ is aryl optionally substituted with OH, O-(1-6C alkyl), $C(O)_2$(1-6C alkyl), or (1-6C alkyl)NR'R";

hetCyc$^3$ and hetCyc$^4$ are independently a 5 or 6 membered heterocyclic ring optionally substituted with OH;

hetAr$^2$ is a 5-6 membered heteroaryl ring optionally substituted with one to three groups independently selected from (1-6C)alkyl, (3-6C)cycloalkyl, halogen, CN, $CF_3$, $OCH_2F$, $OCF_3$, O(1-6C alkyl), O(3-6C)cycloalkyl, and NR'R";

hetAr$^3$ is a 5-6 membered heteroaryl ring;

hetAr$^5$ is a 5-6 membered heteroaryl ring optionally substituted with (1-6C)alkyl; and R' and R" are independently H or (1-6C)alkyl.

In certain embodiments of Formula I, $R^1$ is H, F, Cl, Me, Et or isopropyl.

In certain embodiments of Formula I, $R^1$ is H, F or Cl.

In certain embodiments of Formula I, $R^1$ is H, Me, Et or isopropyl.

In one embodiment, $R^1$ is H.

In certain embodiments, $R^{1a}$ is H, F, Cl, CN, Me, Et, or isopropyl.

In certain embodiments, $R^{1a}$ is H, F, Cl, or Me.

In certain embodiments of Formula I, $R^{1a}$ is H or F.

In one embodiment, $R^{1a}$ is H.

In one embodiment, $R^{1a}$ is F.

In certain embodiments of Formula I, $R^2$ is H, F, Cl, Me, Et or isopropyl.

In certain embodiments of Formula I, $R^2$ is H, F or Cl.

In certain embodiments of Formula I, $R^2$ is H, Me, Et or isopropyl.

In one embodiment, $R^2$ is H.

In one embodiment, $R^2$ is F.

In certain embodiments of Formula I, $R^3$ is H, methyl, ethyl, isopropyl, cyclopropyl, or hetAr$^3$. Examples of hetAr$^3$ include 5 membered heteroaryl rings having a nitrogen atom and optionally having a second heteroatom selected from N and O. An example is oxazolyl. A particular value for $R^3$ is the structure:

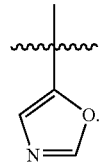

In certain embodiments of Formula I, $R^3$ is H, methyl, ethyl, isopropyl, or oxazolyl.

In certain embodiments of Formula I, $R^3$ is H, methyl, ethyl, or isopropyl.

In certain embodiments of Formula I, $R^3$ is H, methyl, or hetAr$^3$.

In certain embodiments of Formula I, $R^3$ is H, methyl, or oxazolyl.

In certain embodiments of Formula I, $R^3$ is H.

In certain embodiments of Formula I, $R^4$ is H, F, Cl, Me, Et or isopropyl.

In certain embodiments of Formula I, $R^4$ is H, F or Cl.

In certain embodiments of Formula I, $R^4$ is H, Me, Et or isopropyl.

In one embodiment, $R^4$ is H.

In one embodiment, $R^4$ is F.

In certain embodiments, $R^5$, $R^6$, $R^7$ and $R^8$ are independently selected from H, F and Me.

In one embodiment, $R^5$ is H.

In one embodiment, $R^6$ is H.

In one embodiment, $R^7$ is H.

In one embodiment, $R^8$ is H.

In certain embodiments, of Formula I, each of $R^1$ and $R^4$ is hydrogen.

In certain embodiments, of Formula I, each of $R^5$, $R^6$, $R^7$ and $R^8$ is hydrogen.

In certain embodiments, of Formula I, each of $R^1$, $R^4$, $R^5$, $R^6$, $R^7$ and $R^8$ is hydrogen.

In certain embodiments, of Formula I, each of $R^1$, $R^{1a}$, $R^2$, $R^3$, $R^4$, $R^5$, $R^6$, $R^7$ and $R^8$ is hydrogen.

In certain embodiments, A is $-Z(CH_2)_p(hetCyc^{2a})$.

In certain embodiments, A is represented by the formula $-NH\text{-}hetCyc^{2a}$.

In certain embodiments, A is represented by the formula $-NH-(CH_2)\text{-}hetCyc^{2a}$.

In certain embodiments, A is represented by the formula $-NH-(CH_2)_2\text{-}hetCyc^{2a}$.

In certain embodiments, A is represented by the formula $-O\text{-}hetCyc^{2a}$.

In certain embodiments, A is represented by the formula $-O-(CH_2)\text{-}hetCyc^{2a}$.

In certain embodiments, A is represented by the formula $-O-(CH_2)_2\text{-}hetCyc^{2a}$.

Examples of $hetCyc^{2a}$ include 5-6 membered heterocyclic rings having one or two heteroatoms independently selected from N and O. Particular values of $hetCyc^{2a}$ include pyrrolidinyl, piperidinyl rings and morpholinyl rings. In certain embodiments, $hetCyc^{2a}$ is substituted with one or more $R^9$ groups. In certain embodiments, $hetCyc^{2a}$ is unsubstituted.

In certain embodiments, A is Z-$hetCyc^{2b}$.

In certain embodiments, A is $-NH(hetCyc^{2b})$.

In other embodiments, A is $-O\text{-}(hetCyc^{2b})$.

Examples of $hetCyc^{2b}$ include 7-11 membered bridged aza- or diaza-heterocycles. Particular values of $hetCyc^{2b}$ include azabicyclo[2.2.1]heptane, azabicyclo[3.2.1]octane, 3-azabicyclo[3.2.1]octane, diazabicyclo[2.2.1]heptane, and diazabicyclo[3.2.1]octane.

In certain embodiments, $hetCyc^{2b}$ is substituted with one or more $R^9$ groups.

In certain embodiments, $hetCyc^{2b}$ is unsubstituted.

In certain embodiments, $hetCyc^{2a}$ and $hetCyc^{2b}$ are optionally substituted with one or more $R^9$ groups independently selected from halogen, (1-6C)alkyl, $NR^aR^b$, -(1-6C alkyl)$NR^aR^c$, $OR^a$, (1-6C alkyl)$OR^a$ [optionally substituted with amino], $C(O)NR^aR^c$, $C(O)(CR^xR^y)NR^aR^c$, $NHC(O)R^e$, $NHC(O)(CR^mR^n)NR^aR^c$, $NHC(O)NR^fR^g$, (1-6C alkyl)-$hetAr^1$, (1-6C alkyl)-$hetCyc^1$, oxo, and C(O)O(1-6C alkyl).

Examples of $R^9$ groups having the formula (1-6C)alkyl include methyl, ethyl, and propyl.

Examples of $R^9$ groups having the formula $NR^aR^b$ include groups where $R^a$ is H or Me and $R^b$ is H, methyl, ethyl, propyl, butyl, t-butyl, $CH_2C(CH_3)_2OH$, cyclopropyl, phenyl, or $CH_2hetAr^4$. Examples of $hetAr^4$ include 6 membered heteroaryl rings having 1-2 nitrogen atoms, for example pyridyl and pyrimidyl. Particular values of $R^9$ when represented by $NR^aR^b$ include $NH_2$ and $NMe_2$.

In other embodiments, $R^9$ is a group having the formula $NR^aR^b$ wherein $R^a$ is H or (1-6C alkyl), and $R^b$ is H, (1-6C alkyl), (1-6C fluoroalkyl), (1-6C alkyl)-O-(1-6C alkyl) or (1-6C alkyl)OH. Further particular values of $R^9$ include $NH_2$, NHMe, $NMe_2$, $NHCH(CH_3)CH_2F$, $NHCH_2CH_2OMe$, $NHCH_2CH_2OH$ and $N(CH_3)CH_2CH_2OH$.

Examples of $R^9$ groups having the formula (1-6C alkyl)$NR^aR^c$ include groups where $R^a$ is H or Me and $R^c$ is H, methyl, or cyclopropyl. Particular values of $R^9$ when represented by (1-6C alkyl)$NR^aR^c$ include $CH_2CH_2$ and $CH_2CH_2NMe_2$.

Examples of $R^9$ groups having the formula $OR^a$ include groups where $R^a$ is H or (1-6C) alkyl. Particular mention is made of OH. Further mention is made of OMe.

Examples of $R^9$ groups having the formula (1-6C alkyl)$OR^a$ optionally substituted with an amino group include groups where $R^a$ is H. Particular values of such substituents include $CH_2OH$. A further example of $R^9$ is $CH(NH_2)CH_2OH$.

Examples of $R^9$ groups having the formula $C(O)NR^aR^c$ include groups where $R^a$ is H or Me and $R^c$ is (1-6C)alkyl, for example methyl. A particular value of $R^1$ is C(O)NHMe.

Examples of $R^9$ groups having the formula $C(O)(CR^xR^y)NR^aR^c$ include groups wherein $R^x$ and $R^y$ are independently H or methyl, $R^a$ is H or methyl, and $R^c$ is H or (1-6C)alkyl, for example methyl. In another embodiment, $R^x$ and $R^y$ together with the atom to which they are attached form a cyclopropyl ring. That is, $CR^xR^y$ forms a cyclopropyl ring. Particular values of $R^9$ include $C(O)C(CH_3)_2NH_2$, $C(O)CH(CH_3)NH_2$, $C(O)CH_2NH_2$, $C(O)CH_2NMe_2$, and C(O)C(cyclopropylidine)$NH_2$.

Examples of $R^9$ groups having the formula $NHC(O)R^e$ include groups wherein $R^e$ is methyl.

Examples of $R^9$ groups having the formula $NHC(O)(CR^mR^n)NR^aR^c$ include groups wherein $R^m$ and $R^n$ are independently H or methyl, $R^a$ is H or Me, and $R^c$ is H or Me. Particular values of $R^9$ include $NHC(O)CH_2NH_2$, $NHC(O)CH(CH_3)NH_2$, and $NHC(O)C(CH_3)_2NH_2$.

Examples of $R^9$ groups having the formula $NHC(O)NR^fR^g$ include groups wherein $R^f$ and $R^g$ are independently H or Me. A particular value includes $NHC(O)NH_2$.

Examples of $R^9$ groups having the formula (1-6C alkyl)-$hetAr^1$ include groups wherein $hetAr^1$ is a 6 membered heteroaryl having at least one nitrogen atom, for example a pyridyl group. Particular values of $R^9$ include $CH_2$(pyrid-2-yl) and $CH_2$(pyrid-4-yl).

Examples of $R^9$ groups having the formula (1-6C alkyl)-$hetCyc^1$ include groups wherein $hetCyc^1$ is a 5-6 membered ring having 1-2 nitrogen atoms. Particular values of $hetCyc^1$ include optionally substituted piperazinyl or pyrrolidinyl rings. In certain embodiments, $hetCyc^1$ is optionally substituted with OH or an alkyl group, for example methyl.

In certain embodiments, $R^9$ is halogen. A particular example is fluoro.

In certain embodiments, $R^9$ is $CF_3$.

In certain embodiments, $R^9$ is CN.

In certain embodiments of Formula I, A is $-Z(CH_2)_p(hetCyc^{2a})$ wherein $hetCyc^{2a}$ is optionally substituted with one or more $R^9$ groups independently selected from halogen, (1-6C alkyl), C(O)O(1-6C alkyl) and $-OR^a$.

In certain embodiments, $hetCyc^{2a}$ is optionally substituted with one or more $R^9$ groups independently selected from F, methyl, $C(O)_2Me$, OH, and OMe.

In certain embodiments of Formula I, A is Z-hetCyc$^{2b}$ wherein hetCyc$^{2b}$ is optionally substituted with one or more R$^9$ groups independently selected from halogen, (1-6C alkyl), and —OR$^a$.

In certain embodiments, hetCyc$^{2b}$ is optionally substituted with one or more R$^9$ groups independently selected from F, Me and OH.

In certain embodiments, hetCyc$^{2b}$ is unsubstituted.

In other embodiments, hetCyc$^{2a}$ and hetCyc$^{2b}$ are optionally substituted with one or more R$^9$ groups independently selected from NH$_2$, NMe$_2$, Me, OH, CH$_2$OH, C(O)NHMe, CH$_2$NH$_2$, CH$_2$CH$_2$NH$_2$ and CO$_2$Me. Particular mention is made of NH$_2$.

In other embodiments, hetCyc$^{2a}$ and hetCyc$^{2b}$ are optionally substituted with one or more R$^9$ groups independently selected from NH-cyclopropyl, NH(t-butyl), NHMe, NHCH$_2$C(CH$_3$)$_2$OH, NHCH$_2$(pyrid-2-yl), NHCH$_2$(pyrid-4-yl), oxo, CH(NH$_2$)CH$_2$OH, C(O)C(CH$_3$)$_2$NH$_2$, C(O)CH(CH$_3$)NH$_2$, C(O)CH$_2$NH$_2$, C(O)CH$_2$NMe$_2$, C(O)C(cyclopropylidine)NH$_2$, CH$_2$CH$_2$NHMe, CH$_2$NMe$_2$, CH$_2$NH-cyclopropyl, CH$_2$NHMe, CH$_2$-(4-methylpiperazinyl), CH$_2$(3-hydroxypyrrolidinyl), NHC(O)Me, NHC(O)NH$_2$, NHC(O)CH$_2$NH$_2$, NHC(O)CH(CH$_3$)NH$_2$, NHC(O)C(CH$_3$)$_2$NH$_2$, CH$_2$(pyrid-2-yl), and CH$_2$(pyrid-4-yl).

Particular values of A when represented by the formula —Z(CH$_2$)$_p$(hetCyc$^{2a}$) or Z-hetCyc$^{2b}$ include the structures:

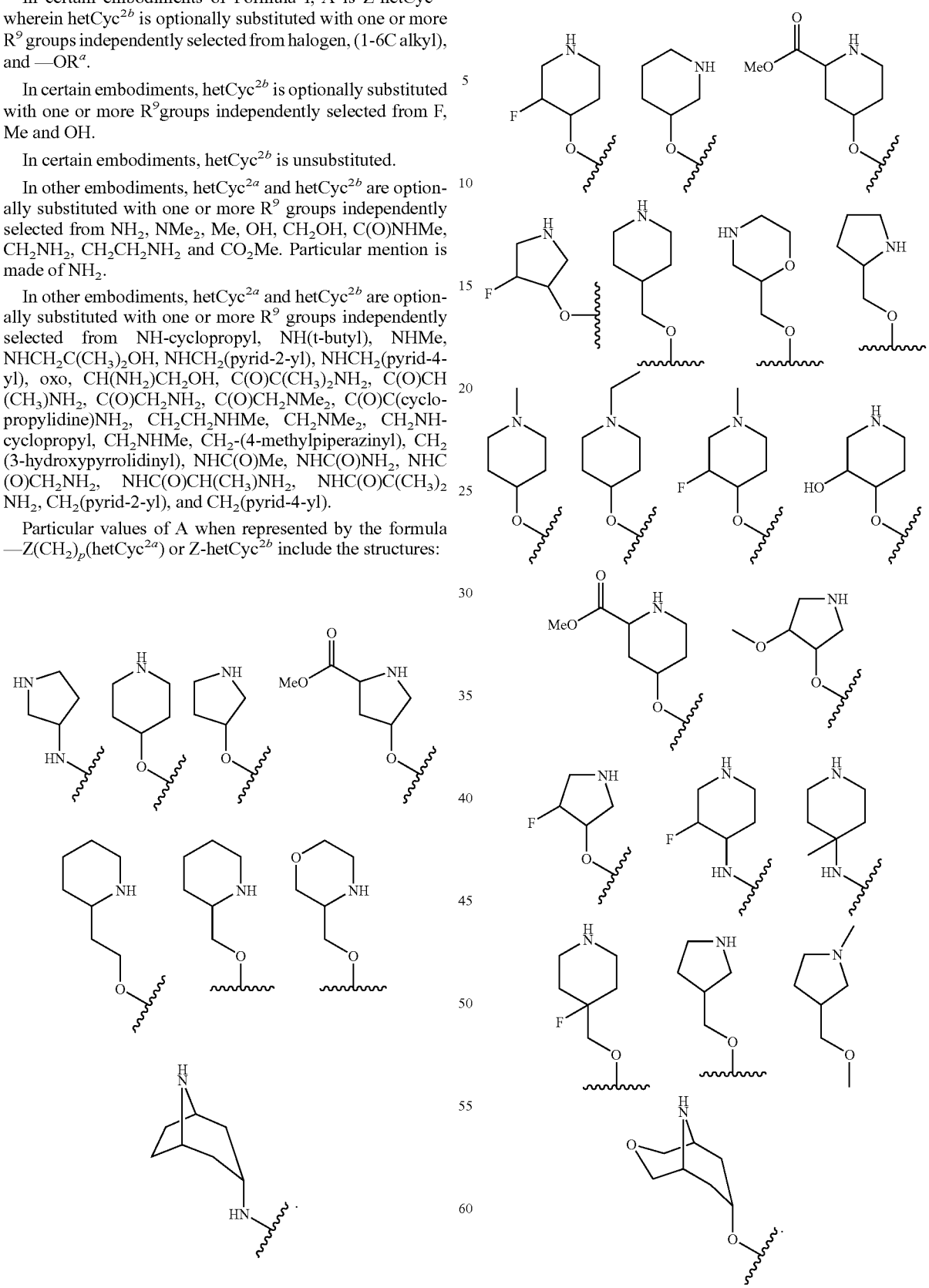

Additional values for the A group when represented by the formula —Z(CH$_2$)$_p$(hetCyc$^{2a}$) or Z-hetCyc$^{2b}$ include the structures:

The values of A shown above include the cis- and trans-isomers where possible.

In certain embodiments of Formula I, A is —O-hetCyc$^{2a}$. In particular embodiments, hetCyc$^{2a}$ is substituted with a fluoro group. In particular embodiments, hetCyc$^{2a}$ is a piperidinyl ring. In particular embodiments, A is a group having the formula:

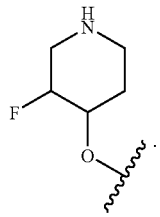

In particular embodiments, the A group is in the trans-configuration.

In certain embodiments, A is ZR$^{10}$. In certain embodiments, Z is O. In certain embodiments, Z is N.

Particular values for R$^{10}$ include straight chain and branched (1-6C alkyl) groups. In certain embodiments, R$^{10}$ is substituted with NR'R". Particular mention is made of NH$_2$. A particular value for R$^{10}$ is CH$_2$C(CH$_3$)$_2$CH$_2$NH$_2$. Additional values for R$^{10}$ include CH$_2$C(CH$_3$)$_2$N(CH$_3$)$_2$ and CH$_2$CH$_2$NH$_2$.

Particular values for A when represented by ZR$^{10}$ include —OMe, —OCH$_2$C(CH$_3$)$_2$CH$_2$NH$_2$, —OCH$_2$C(CH$_3$)$_2$N(CH$_3$)$_2$ and —OCH$_2$CH$_2$NH$_2$.

In certain embodiments, A is ZR$^{11}$. In certain embodiments, Z is O. In certain embodiments, A is N. In certain embodiments, R$^{11}$ is substituted with NR'R". In certain embodiments, R' and R" are independently selected from H and methyl. Particular mention is made of NH$_2$. Particular examples of R$^{11}$ include amino-substituted cyclopentyl and amino-substituted cyclohexyl rings. A particular value of A is:

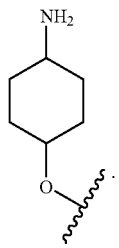

The examples of A when represented by ZR$^{11}$ include the cis- and trans-isomers.

In certain embodiments, B is CN.
In certain embodiments, B is H.
In certain embodiments, B is OR$^h$.
In certain embodiments, B is represented by OR$^h$ wherein R$^h$ is H.
In certain embodiments, B is represented by OR$^h$ wherein R$^h$ is CF$_3$.

Particular values for OR$^h$ when R$^h$ is represented by (1-6C) alkyl include OMe, OEt and O-(isobutyl).

Particular values for OR$^h$ when R$^h$ is represented by -(1-6Calkyl)-(3-6C cycloalkyl) include —O-(1-6Calkyl)-cyclopropyl, for example —OCH$_2$-cyclopropyl.

Particular values for OR$^h$ when R$^h$ is represented by -(1-6C alkyl)-O-(1-6C alkyl) include —OCH$_2$CH$_2$OMe and —OCH$_2$CH$_2$CH$_2$OMe.

Particular values for OR$^h$ when R$^h$ is represented by -(1-6C alkyl)OH include —OCH$_2$CH$_2$OH.

A particular value for OR$^h$ when R$^h$ is represented by -(1-6C alkyl)-S-(1-6C alkyl) includes —OCH$_2$CH$_2$CH$_2$SMe.

Particular values for OR$^h$ when R$^h$ is represented by -(1-6C alkyl)NR'R" include groups wherein R' and R" are independently H or Me, for example, —OCH$_2$CH$_2$CH$_2$NH$_2$, —OCH$_2$CH$_2$NMe$_2$, and —OCH$_2$CH$_2$CH$_2$NMe$_2$. A further example of OR$^h$ includes —OCH$_2$CH$_2$NH$_2$.

Particular values for OR$^h$ when R$^h$ is represented by hetCyc$^4$ include groups wherein hetCyc$^4$ is a 5-6 membered heterocyclic ring having 1-2 atoms independently selected from N and O. In certain embodiments, R$^h$ is a 5-6 membered heterocycle having a ring oxygen atom, for example a tetrahydrofuranyl or tetrahydropyranyl ring. Examples of OR$^h$ include:

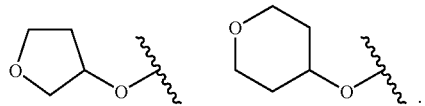

Particular values for OR$^h$ when R$^h$ is represented by (1-6C alkyl)hetCyc$^4$ include groups wherein hetCyc$^4$ is a 5-6 membered heterocyclic ring having 1-2 atoms independently selected from N and O. A particular example of OR$^h$ includes the structure:

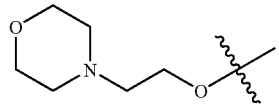

Particular values for OR$^h$ when R$^h$ is represented by (1-6C alkyl)aryl include groups wherein the aryl is a phenyl group, such as OCH$_2$Ph.

Particular values for OR$^h$ when R$^h$ is represented by (1-6C alkyl)-hetAr$^5$ include groups wherein hetAr$^5$ is a 5-6 membered heteroaryl ring having 1-3 nitrogen atoms. Examples include pyridyl, triazolyl and pyrazolyl rings. In certain embodiments, hetAr$^5$ is substituted with a group selected from (1-6C) alkyl. Particular examples of OR$^h$ include the structures:

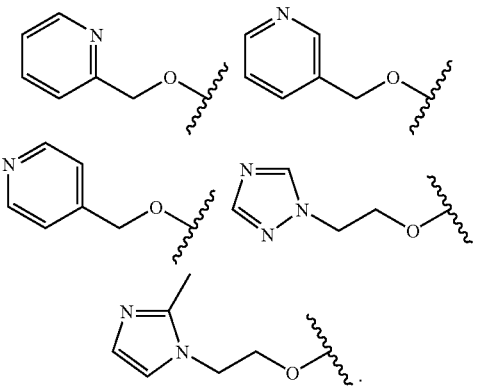

In certain embodiments of Formula I, B is OR$^h$ wherein R$^h$ is (1-6C alkyl)-O-(1-6C alkyl), hetCyc$^4$ or -(1-6C alkyl)-(3-6C cycloalkyl).

In certain embodiments, of Formula I, B is OR$^h$ wherein R$^h$ is (1-6C alkyl)-O-(1-6C alkyl), a 5-6 membered heterocycle having a ring oxygen atom, or —CH$_2$(cyclopropyl).

In certain embodiments, B is C(O)NR$^i$R$^j$. In certain embodiments, R$^i$ is H. In certain embodiments, R$^j$ is (1-6C alkyl), for example methyl. In other embodiments, R$^j$ is (1-6C alkyl)O(1-6 alkyl), for example (1-6C alkyl)OMe. In other embodiments, R$^j$ is (1-6C alkyl)OH for example (1-6C alkyl)OH. Particular values for B include —C(O)NHMe, —C(O)NHCH$_2$CH$_2$OMe, and —C(O)NHCH$_2$CH$_2$OH. A further example includes —C(O)NMe$_2$.

In certain embodiments, B is C(O)-hetCyc$^3$. Examples of hetCyc$^3$ include 5-6 membered heterocyclic rings having 1-2 atoms independently selected from N and O. Particular values for B in include the structures:

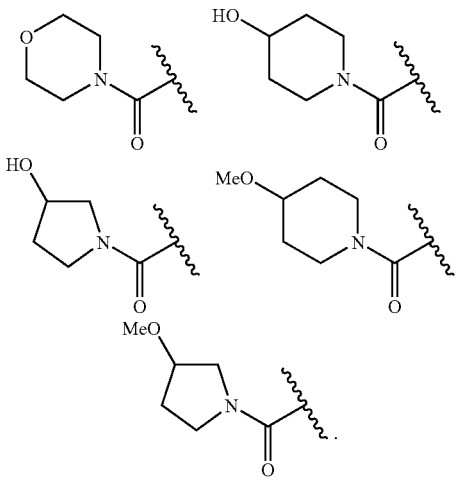

In certain embodiments, B is C(O)(1-6C alkyl)hetCyc$^3$. In certain embodiments, B is C(O)NH(1-6C alkyl)hetCyc$^3$. Examples of hetCyc$^3$ include 5-6 membered heterocyclic rings having 1-2 atoms independently selected from N and O. In certain embodiments, hetCyc$^3$ is substituted with OH or OMe. A particular value for B includes the structure:

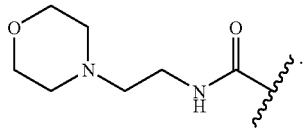

In certain embodiments, B is hetAr$^2$. Examples of hetAr$^2$ include 5-6 membered heteroaryl rings having 1-2 nitrogen atoms. In certain embodiments, hetAr$^2$ is substituted with —O(1-6C alkyl), such as methoxy. Particular values for B include 3-pyridyl, 4-pyridyl, and 4-methoxypyridin-3-yl. Examples further include pyridyl groups optionally substituted with (1-6C)alkyl, for example methyl. A particular example includes 4-methylpyrid-3-yl. Additional examples of B when represented by hetAr$^2$ include pyrimidyl groups, such as 2-pyrimidyl and 5-pyrimidyl.

In certain embodiments, B is SR$^k$. In certain embodiments, R$^k$ is a 3-6 membered carbocyclic ring. In other embodiments, R$^k$ is -(1-6C alkyl)O(1-6 alkyl), e.g., (1-6C alkyl)OCH$_3$. Particular values for B include S-cyclohexyl and S(CH$_2$CH$_2$)OCH$_3$.

In certain embodiments, B is Ar$^1$. In certain embodiments, Ar$^1$ is phenyl which is unsubstituted or substituted with OH, O-(1-6C alkyl), C(O)$_2$(1-6C alkyl), or (1-6C alkyl)NR'R". Particular values for B include phenyl, hydroxyphenyl, 3-methoxyphenyl, 4-(methylamino)phenyl, or 4-(methoxycarbonyl)phenyl.

In certain embodiments, B is -(1-6 alkyl)NR'R". Particular values include CH$_2$NHMe and CH$_2$NMe$_2$.

In certain embodiments, B is —SO$_2$N(1-6 alkyl)$_2$, for example SO$_2$NMe$_2$.

In certain embodiments, B is (1-3C)alkyl. A particular value is ethyl.

In certain embodiments of Formula I, B is selected from OR$^h$, (1-3C)alkyl, hetAr$^2$ and hetCyc$^4$. In certain embodiments, B is selected from —OCH$_2$CH$_2$OCH$_3$, —OCH$_2$CH$_2$OH, —OCH$_2$(cyclopropyl), ethyl, 2-pyridyl, 3-pyridyl, 4-pyridyl, 4-methylpyrid-3-yl, 2-pyrimidyl, 5-pyrimidyl,

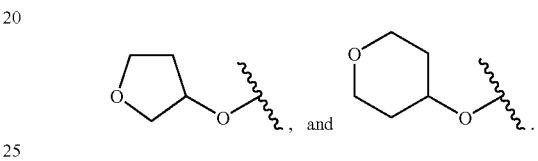

In certain embodiments of Formula I, B is selected from OR$^h$.

In certain embodiments, R$^h$ is (1-6C alkyl)-O-(1-6C alkyl), (1-6C alkyl)-(3-6C cycloalkyl), -(1-6C alkyl)OH, or hetCyc$^4$.

In certain embodiments of Formula I, B is selected from —OCH$_2$CH$_2$OCH$_3$, —OCH$_2$CH$_2$OH, —OCH$_2$(cyclopropyl),

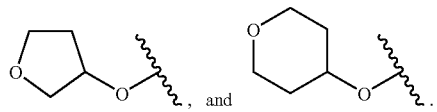

In certain embodiments of Formula I, B is —OCH$_2$CH$_2$OCH$_3$.

In certain embodiments of Formula I, B is hetAr$^2$.

In certain embodiments, B is a pyridyl ring or a pyrimidyl ring.

In certain embodiments of Formula I, B is selected from 2-pyridyl, 3-pyridyl, 4-pyridyl, or 2-pyrimidyl.

In certain embodiments of Formula I, B is 3-pyridyl.

Compounds of Formula I include compounds wherein:

A is —Z—(CH$_2$)$_p$-(hetCyc$^{2a}$), —Z-(hetCyc$^{2b}$), Z—R$^{10}$ or Z—R$^{11}$;

Z is O or NH;

p is 0, 1 or 2;

hetCyc$^{2a}$ is a 5 or 6 membered heterocyclic ring having 1-2 ring heteroatoms independently selected from N and O, wherein hetCyc$^{2a}$ is optionally substituted with one or more R$^9$ groups;

hetCyc$^{2b}$ is a 7-12 membered spirocyclic or bridged heterobicyclic ring system having 1-2 ring heteroatoms independently selected from N and O, wherein hetCyc$^{2b}$ is optionally substituted with one or more R$^9$ groups;

R$^{10}$ is 1-6C alkyl or (1-6C alkyl)NR'R";

R$^{11}$ is (5-6C)cycloalkyl substituted with NR'R";

B is OR$^h$, (1-3C)alkyl, or pyridyl;

R$^1$, R$^{1a}$, R$^2$, and R$^4$ are independently H or F;

R$^3$ is H, For hetAr$^3$;

R$^5$, R$^6$, R$^7$ and R$^8$ are independently H or F;

each $R^9$ is independently selected from halogen, C(O)O(1-6C alkyl), (1-6C alkyl), OH, and —O(1-6C alkyl);

$R^h$ is (1-6C alkyl)-O-(1-6C alkyl), a 5-6 membered heterocycle having a ring oxygen atom, or cyclopropylmethyl;

hetAr$^3$ is a 5-6 membered heteroaryl ring having 1-2 ring heteroatoms independently selected from N and O; and R' and R" are independently H or (1-6C)alkyl.

The term "halogen" as used herein includes F, Cl, Br, and I.

The term "$C_1$-$C_6$ alkyl" as used herein refers to saturated linear or branched-chain monovalent hydrocarbon radicals of one to six carbon atoms, respectively. Examples include, but are not limited to, methyl, ethyl, 1-propyl, 2-propyl, 1-butyl, 2-methyl-1-propyl, 2-butyl, 2-methyl-2-propyl, 2,2-dimethylpropyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl.

The term "-(1-6C alkyl)-(3-6C cycloalkyl)" refers to a saturated linear or branched-chain monovalent hydrocarbon radical of one to six carbon atoms, wherein one of the hydrogen atoms is replaced with a 3-6 membered cycloalkyl group.

Compounds according to the present invention have been found to be class 3 receptor tyrosine kinase inhibitors and are useful in the treatment of cancers, such as hematological cancers (e.g., leukemias such as AML), breast cancer, colon cancer, gliomas, fibrosis (including liver fibrosis and lung fibrosis, and scleroderma.

It will be appreciated that certain compounds according to the invention may contain one or more centers of asymmetry and may therefore be prepared and isolated in a mixture of isomers such as a racemic mixture, or in an enantiomerically pure form.

It will further be appreciated that the compounds of Formula I or their salts may be isolated in the form of solvates, and accordingly that any such solvate is included within the scope of the present invention.

The compounds of Formula I include pharmaceutically acceptable salts thereof. In addition, the compounds of Formula I also include other salts of such compounds which are not necessarily pharmaceutically acceptable salts, and which may be useful as intermediates for preparing and/or purifying compounds of Formula I and/or for separating enantiomers of compounds of Formula I.

According to another aspect, the present invention provides a process for the preparation a compound of Formula I or a salt thereof as defined herein which comprises:

(a) for a compound of the Formula I wherein A is —NH—(CH$_2$)$_n$(hetCyc$^{2a}$), —NH-(hetCyc$^{2b}$), NHR$^{10}$ or NHR$^{11}$, coupling a corresponding compound having the formula II

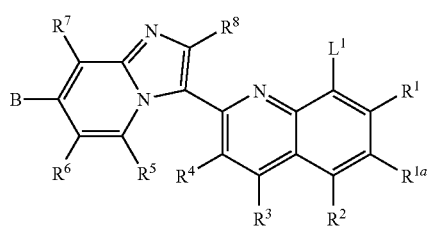

wherein L$^1$ represents a leaving group or atom, with a compound having the formula NH$_2$(CH$_2$)$_n$(hetCyc$^{2a}$), H$_2$N-hetCyc$^{2b}$, NH$_2$R$^{10}$ or NH$_2$R$^{11}$, using a palladium catalyst and a ligand in the presence of a base; or (b) for a compound of Formula I where B is OR$^h$, reacting a corresponding compound having the Formula III

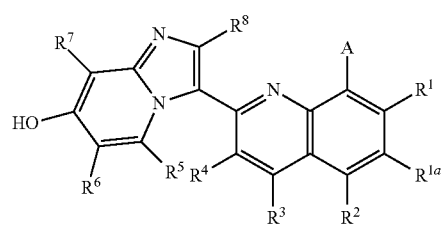

with a compound of the formula R$^h$-L$^2$ wherein L$^2$ represents a leaving group in the presence of a base; or (c) for a compound of Formula I where B is OR$^h$, reacting a corresponding compound having the Formula III with a compound having the formula R$^h$—OH in the presence of a coupling reagent; or (d) for a compound of Formula I wherein A is —O—(CH$_2$)$_n$ hetCyc$^{2a}$, —O-hetCyc$^{2b}$, OR$^{10}$ or OR$^{11}$, reacting a corresponding compound having the formula IV

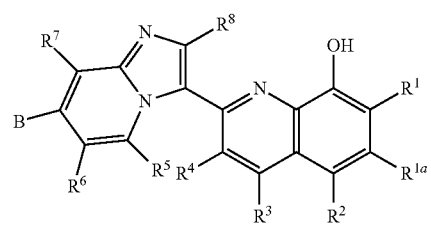

with a corresponding compound having the formula HO—(CH$_2$)$_n$hetCyc$^{2a}$, HO-hetCyc$^{2b}$, HOR$^{10}$ or HOR$^{11}$ in the presence of a coupling agent and triphenylphosphine in a suitable solvent; or e) for a compound of Formula I wherein A is —O—(CH$_2$)$_n$ hetCyc$^{2a}$, reacting a compound of Formula IV with a compound having the formula MeSO$_2$—O(CH$_2$)$_n$hetCyc$^{2a}$ in the presence of a base; or (f) for a compound of Formula I wherein R$^3$ is hetAr$^3$ and hetAr$^3$ is oxazolyl, cyclizing a compound having the formula V

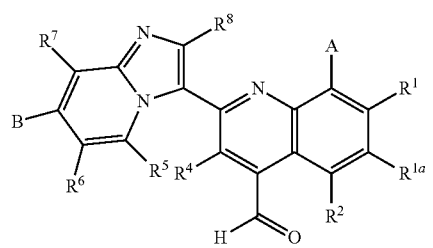

with a compound having the formula

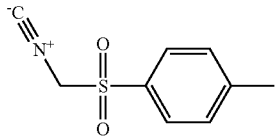

in the presence of a base; or (g) for a compound of Formula I wherein A is

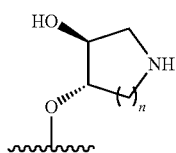

and n is 1 or 2, reacting a corresponding compound having the formula IV

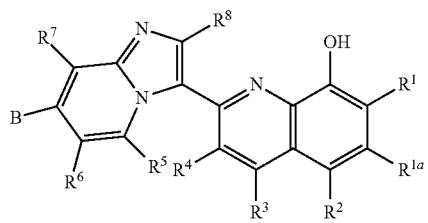

with a compound having the formula

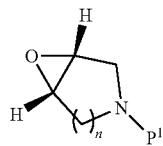

wherein n is 1 or 2 and $P^1$ is an amine protecting group, in the presence of a base; or (h) for a compound of Formula I wherein A is:

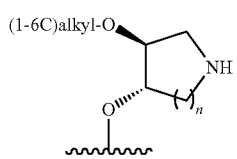

and n is 1 or 2, reacting a corresponding compound having the formula VII

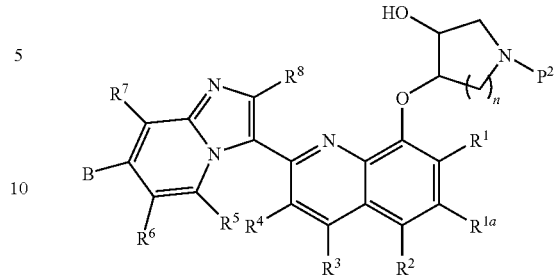

wherein n is 1 or 2, and $P^2$ is H or an amine protecting group, with a compound having the formula (1-6C alkyl)$L^3$ where $L^3$ is a leaving group or atom in the presence of a base; or (i) for a compound of Formula I wherein A is O-(1-6C alkyl)NR'R", reacting a compound having the formula IV

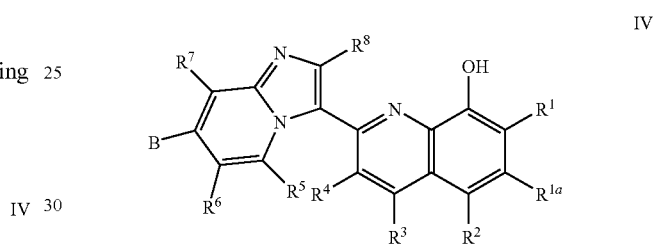

with a compound having the formula $L^4$-(1-6C alkyl)NR'R" where $L^4$ is a leaving group or atom, in the presence of a base and optionally in the presence of a phase transfer catalyst; or (j) for a compound of Formula I wherein A is:

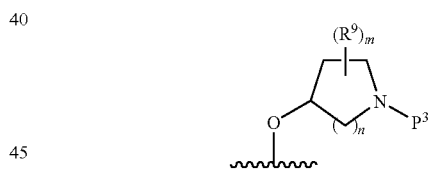

and n is 1 or 2, $P^3$ is (1-6C)alkyl, reacting a corresponding compound having the formula VIII

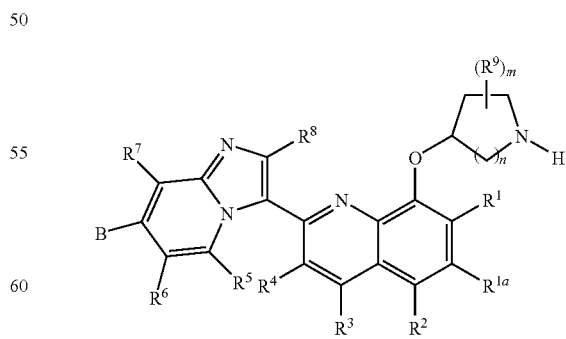

with a compound having the formula HC(O)$P^{3a}$ where $P^{3a}$ is H or (1-6C)alkyl, in the presence of a reducing agent; and
removing any protecting group or groups and optionally forming a salt.

Referring to method (a), the leaving atom $L^1$ may be, for example a halogen atom such as Br or I. Alternatively, $L^1$ can be a leaving group, such as a hydrocarbylsulfonyloxy group, for example, a triflate group, or an arylsulfonyloxy group or an alkylsulfonyloxy group, such as a mesylate or a tosylate group. Suitable palladium catalysts include Pd(0) and Pd(II) catalysts, for example $Pd_2(dba)_3$ and $Pd(OAc)_2$. Suitable ligands include rac-BINAP or DIPHOS. The base may be, for example, an alkali metal carbonate or alkoxide, such as for example cesium carbonate or sodium tert-butoxide. Convenient solvents include aprotic solvents such as ethers (for example tetrahydrofuran or p-dioxane) or toluene. The coupling of a compound of formula (II) with $HNR^{10}R^{11}$ can be conveniently performed at a temperature between 0° C. and reflux, and more particularly at reflux.

Referring to method (b), the leaving atom $L^1$ may be, for example a halogen atom such as Br, Cl or I. Alternatively, $L^1$ can be a leaving group, for example an arylsulfonyloxy group or an alkylsulfonyloxy group, such as a mesylate or a tosylate group. The base may be, for example, an alkali metal hydride or carbonate, such as sodium hydride, potassium hydride, sodium carbonate, potassium carbonate or cesium carbonate. Convenient solvents include aprotic solvents such as ethers (for example tetrahydrofuran or p-dioxane), DMF, or acetone. The reaction can be conveniently performed at a temperature ranging from −78 to 100° C.

Referring to method (c), the coupling reagent may be any suitable reagent(s) known to those skilled in the art, for example, DEAD and $PPh_3$. Convenient solvents include aprotic solvents such as ethers (for example tetrahydrofuran). The reaction can be conveniently performed at a temperature ranging from −78 to 100° C.

Referring to method (d), the coupling reagent may be any suitable reagent(s) known to those skilled in the art, for example, DEAD and $PPh_3$. Convenient solvents include aprotic solvents such as ethers (for example tetrahydrofuran). The reaction can be conveniently performed at a temperature ranging from −78 to 100° C.

Referring to method (e), the base may be, for example, an alkali metal hydride or carbonate, such as sodium hydride, potassium hydride, sodium carbonate, potassium carbonate or cesium carbonate. Convenient solvents include aprotic solvents such as ethers (for example tetrahydrofuran or p-dioxane), dimethylformamide, dimethylacetamide, or acetone. The reaction can be conveniently performed at a temperature ranging from ambient temperature to 100° C.

Referring to method (f), the base may be, for example, an alkali metal hydride or carbonate, such as sodium hydride, potassium hydride, sodium carbonate, potassium carbonate or cesium carbonate. Convenient solvents include alcohols such as methanol. The reaction can be conveniently performed at a temperature ranging from ambient temperature to 100° C.

Referring to method (g), the base may be, for example, an alkali metal hydride or carbonate, such as sodium hydride, potassium hydride, sodium carbonate, potassium carbonate or cesium carbonate. Convenient solvents include aprotic solvents such as ethers (for example tetrahydrofuran or p-dioxane), dimethylformamide, dimethylacetamide, or acetone. The reaction can be conveniently performed at a temperature ranging from ambient temperature to 100° C.

Referring to method (h), the base may be, for example, an alkali metal hydride, such as sodium hydride, potassium hydride, or lithium hydride. Convenient solvents include aprotic solvents such as ethers (for example tetrahydrofuran or p-dioxane), dimethylformamide, dimethylacetamide, or acetone. The leaving atom $L^3$ may be, for example a halogen atom such as Br, Cl or I. Alternatively, $L^3$ can be a leaving group, for example an arylsulfonyloxy group or an alkylsulfonyloxy group, such as a mesylate or a tosylate group.

Referring to method (i), the base may be, for example, an alkali metal hydroxide, such as sodium hydroxide, potassium hydroxide, lithium hydroxide or cesium hydroxide. Convenient solvents include aprotic solvents such as ethers (for example tetrahydrofuran or p-dioxane), dimethylformamide, dimethylacetamide, or acetone. The leaving atom $L^4$ may be, for example a halogen atom such as Br, Cl or I. Alternatively, $L^4$ can be a leaving group, for example an arylsulfonyloxy group or an alkylsulfonyloxy group, such as a mesylate or a tosylate group. The reaction is optionally performed in the presence of a phase transfer catalyst such as tetrabutylammonium iodide. The reaction can be conveniently performed at a temperature ranging from ambient temperature to 100° C.

Referring to method (j), suitable reducing agents include borohydride reagents such as sodium triacetoxyborohydride or sodium cyanoborohydride.

Suitable amine protecting groups for the above methods include any convenient amine protecting group, for example as described in Greene & Wuts, eds., "Protecting Groups in Organic Synthesis", John Wiley & Sons, Inc. Examples of amine protecting groups include acyl and alkoxycarbonyl groups, such as t-butoxycarbonyl (BOC).

A compound of Formula II

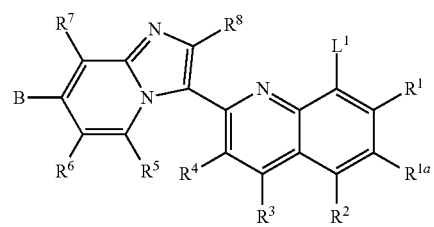

can be prepared by reacting corresponding 2,8-dibromoquinoline having the formula

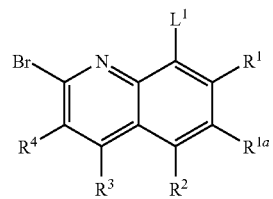

with a corresponding compound having the formula

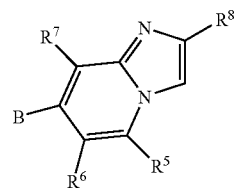

using a palladium catalyst (such as $Pd(PPh_3)_4$, $Pd_2(dba)_3$ or $Pd(OAc)_2$) and a palladium ligand (for example rac-BINAP or DIPHOS) in the presence of a suitable base, for example an alkali metal carbonate or alkoxide base (e.g., cesium carbonate, potassium carbonate, or sodium tert-butoxide) in a suitable solvent (such as toluene or dioxane) at a temperature ranging from about ambient temperature to reflux.

A compound of Formula IV can be prepared by reacting a compound having the formula

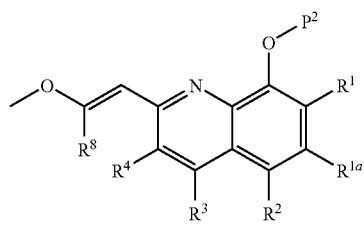

wherein $P^2$ represents an alcohol protecting group, such as t-butyldimethylsilyl, with a compound having the formula

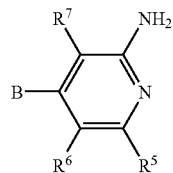

in the presence of N-bromosuccimide or N-chlorosuccinimide in a suitable solvent (such as THF).

The compounds of the formulas (II), (III) and (IV) are believed to be novel and are provided as further aspects of the invention.

The ability of test compounds to act as PDGFR inhibitors may be demonstrated by the assay described in Example A.

The ability of test compounds to act as FLT3 inhibitors may be demonstrated by the assay described in Example B.

Compounds of Formula I are useful for treating diseases and disorders mediated by class 3 and/or class 5 receptor tyrosine kinases. In particular embodiments, compounds of this invention are inhibitors of one or more of the class 3 receptor tyrosine kinases, for example PDGFR and FLT3. For example, compounds of this invention are useful in the treatment fibrosis (including lung, liver and kidney fibroses), scleroderma, and cancers, including hematological malignancies.

As used herein, the term treatment includes prophylaxis as well as treatment of an existing condition.

Examples of hematological malignancies include, for instance, leukemias, lymphomas (non-Hodgkin's lymphoma), Hodgkin's disease (also called Hodgkin's lymphoma), and myeloma—or instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), and multiple myeloma (MM).

Particular examples of PDGFR-driven or dependent cancers which may be treated with compounds of this invention include dermatofibrosarcoma protuberans (DFSB), chronic myelomonocytic leukemia (CMML), hypereosinophilic syndrome (LIES), glioblastoma multiforme (GBM) and gastrointestinal stromal tumors (GIST).

FLT3 inhibitors may also be useful for treating immune related disorders such as bone marrow transplant rejection, solid organ rejection after transplant, ankylosing spondylitis, arthritis, aplastic anemia, Behcet's disease, Graves' disease, hemolytic anemia, hyper IgE syndrome, idiopathic thrombocytopenia purpura (ITP), multiple sclerosis (MS), rheumatoid arthritis, Wegener's granulomatosis, type 1 diabetes mellitus, Myasthenia gravis, and psoriasis.

Particular compounds of this invention are inhibitors of Pim-1 and therefore are useful in treating diseases and disorders mediated by Pim-1, such as cancers such as hematological cancers.

Accordingly, another aspect of this invention provides a method of treating diseases or medical conditions in a mammal mediated by a class 3 and/or class 5 receptor tyrosine kinase, comprising administering to said mammal One or more compounds of Formula I or a pharmaceutically acceptable salt or prodrug thereof in an amount effective to treat or prevent said disorder.

Another aspect of this invention provides a method of treating diseases or medical conditions in a mammal mediated by Pim-1, comprising administering to said mammal one or more compounds of Formula I or a pharmaceutically acceptable salt or prodrug thereof in an amount effective to treat or prevent said disorder.

The phrase "effective amount" means an amount of compound that, when administered to a mammal in need of such treatment, is sufficient to (i) treat or prevent a particular disease, condition, or disorder mediated by a class 3 receptor tyrosine kinase, (ii) attenuate, ameliorate, or eliminate one or more symptoms of the particular disease, condition, or disorder, or (iii) prevent or delay the onset of one or more symptoms of the particular disease, condition, or disorder described herein.

The amount of a compound of Formula I that will correspond to such an amount will vary depending upon factors such as the particular compound, disease condition, and its severity, the identity (e.g., weight) of the mammal in need of treatment, but can nevertheless be routinely determined by one skilled in the art.

As used herein, the term "mammal" refers to a warm-blooded animal that has or is at risk of developing a disease described herein and includes, but is not limited to, guinea pigs, dogs, cats, rats, mice, hamsters, and primates, including humans.

Compounds of the present invention can be used in combination with one or more additional drugs, for example an anti-inflammatory compound, anti-fibrotic compound or a chemotherapeutic that works by the same or by a different mechanism of action.

Compounds of the invention may be administered by any convenient route, e.g. into the gastrointestinal tract (e.g. rectally or orally), the nose, lungs, musculature or vasculature, or transdermally or dermally. The compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a former aspect of the invention.

According to another aspect, the present invention provides a pharmaceutical composition, which comprises a compound of Formula I or a pharmaceutically acceptable salt thereof, as defined hereinabove. In one embodiment, the pharmaceutical composition includes the compound of Formula I together with a pharmaceutically acceptable diluent or carrier.

According to another aspect, the present invention provides a compound of Formula I or a pharmaceutically acceptable salt thereof, for use in therapy, such as the treatment of a class 3 receptor tyrosine kinase-mediated condition.

In certain embodiments, the invention provides a compound of Formula I or a pharmaceutically acceptable salt thereof, for use in the treatment of cancer.

In certain embodiments, the invention provides a compound of Formula I or a pharmaceutically acceptable salt thereof, for use in the treatment of fibrosis.

In certain embodiments, the invention provides a compound of Formula I or a pharmaceutically acceptable salt thereof, for use in the treatment of scleroderma.

According to another aspect, the present invention provides a compound of Formula I or a pharmaceutically acceptable salt thereof, for use in therapy, such as the treatment of a Pim-1-mediated condition.

According to a further aspect, the present invention provides the use of a compound of Formula I or a pharmaceutically acceptable salt thereof, in the manufacture of a medicament to treat a class 3 receptor tyrosine kinase-mediated condition.

According to a further aspect, the present invention provides the use of a compound of Formula I or a pharmaceutically acceptable salt thereof, in the manufacture of a medicament to treat a Pim-1-mediated condition.

EXAMPLES

The following examples illustrate the invention. In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. Tetrahydrofuran (THF), dichloromethane (DCM, methylene chloride), toluene, and dioxane were purchased from Aldrich in Sure seal bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

$^1$HNMR spectra were obtained as $CDCl_3$, $CD_3OD$, $D_2O$ or $d_6$-DMSO solutions (reported in ppm), using tetramethylsilane (0.00 ppm) or residual solvent ($CDCl_3$: 7.25 ppm; $CD_3OD$: 3.31 ppm; $D_2O$: 4.79 ppm; $d_6$-DMSO: 2.50 ppm) as the reference standard. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example A

Cellular PDGFR Assay

The ability of compounds of this invention to inhibit PDGF-induced PDGFR phosphorylation was assessed by using mouse NIH3T3 cells.

25,000 cells in DMEM supplemented with 10% fetal bovine serum were added to each well of a black 96-well cell culture plate. Plates were incubated in a 37° C./5% $CO_2$ incubator for 6-8 hours. Plates were then washed and incubated with serum-free DMEM, and the cells were returned to the 37° C./5% $CO_2$ incubator for 16-20 hours.

Compound test solutions were added at a final concentration of 0.5% DMSO, and the cells were incubated in a 37° C./5% $CO_2$ incubator for 1 hour. PDGF-BB ligand was then added (75 ng/mL) and incubated for 15 minutes. Cells were washed with PBS and fixed in 3.7% formaldehyde in PBS for 10 minutes. This was followed by washing in PBS/0.2% Triton X-100 and permeabilizing in 100% MeOH for 10 minutes. Cells were blocked in Odyssey blocking buffer (LI-COR Biosciences) for 1 hour. Antibodies to phosphorylated PDGFRβ and total PDGFRβ were added to the cells and incubated for 3 hours. After washing with PBS/0.2% TritonX-100, the cells were incubated with fluorescently-labeled secondary antibodies (goat anti-rabbit IgG-IRDye800 and goat anti-mouse IgG-Alexa Fluor 680) for an additional hour. Cells were then washed with PBS and analyzed for fluorescence at both wavelengths using the Odyssey Infrared Imaging System (LI-COR Biosciences). Phosphorylated PDGFR signal was normalized to total PDGFR signal. Compounds of this invention had $IC_{50}$'s values less than 10 μM in this assay.

Example B

Cellular FLT3 Assay

The inhibition of FLT3 ligand (FL)-induced phosphorylated FLT3 in human RS4;11 cells was measured as follows. Cells were plated in 96-well V-bottom plates in RPMI/10%FCS at a concentration of 1 million cells/well. Diluted compounds were added at a final concentration of 0.5% DMSO for one hour. FL was added at a final concentration of 50 ng/ml. After a 15 minute incubation, the cells were pelleted by centrifugation and resuspended in lysis buffer. Phospho-FLT3 was detected by standard ELISA procedure (R&D Systems; DYC368). Briefly, after 20 minutes on ice, the lysate was added to 96-well plates coated with capture antibody to total FLT3. Phospho-FLT3 was detected by the addition of antibody to phospho-tyrosine conjugated to HRP. After addition of substrate and stop solution, the signal was read at A450. Compounds of this invention had $IC_{50}$'s values less than 10 μM in this assay.

Example 1

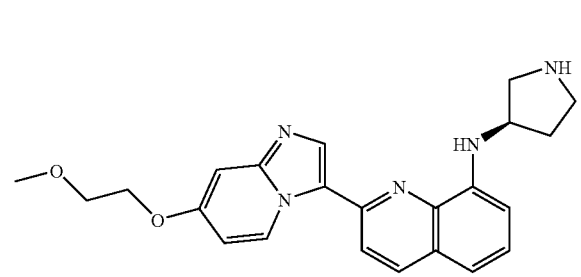

(R)-2-(7-(2-methoxyethoxy)imidazo[1,2-a]pyridin-3-yl)-N-(pyrrolidin-3-yl)quinolin-8-amine Step 1A: Preparation of 2-chloro-4-(2-methoxyethoxy)pyridine: A mixture of 2-chloro-4-nitropyridine (43.6 g, 275.0 mmol) and 2-methoxyethanol (325.6 ml, 425 mmol) was cooled to 0° C. Potassium 2-methylpropan-2-olate (35.73 g, 302.5 mmol) was added and the resulting mixture was stirred while warming to ambient temp over 2 hours. The reaction mixture was concentrated under reduced pressure followed by dilution with 500 ml of water. The resulting mixture was extracted twice with 250 ml of dichloromethane. The combined organic layers were dried over $MgSO_4$ and concentrated under reduced pressure to produce the desired compound as a golden oil (50.2 g, 97% yield) MS APCI (+) m/z 188 and 189.9 (M+1 of each isotope) detected.

Step 1B: Preparation of 4-(2-methoxyethoxy)pyridin-2-amine: A steady stream of nitrogen was passed through a mixture of 2-chloro-4-(2-methoxyethoxy)pyridine (50.17 g, 267.4 mmol), $Pd_2dba_3$ (4.897 g, 5.348 mmol), XPHOS (5.099 g, 10.70 mmol) and tetrahydrofuran (445.7 ml) for 10 minutes. To the resulting degassed mixture was added lithium bis(trimethylsilyl)amide (561.5 ml, 561.5 mmol). After addition, the resulting mixture was heated to 60° C. for 18 hours. The reaction was cooled to ambient temperature and diluted with 1 N hydrochloric acid (200 mL). The resulting solution was washed twice with 500 ml of methyl-tert-butyl ether. The pH of the aqueous layer was taken to 11 with 6 N NaOH and was extracted with dichloromethane (3×500 ml). The combined organic layers were dried over $MgSO_4$ and concentrated under reduced pressure to yield title compound. (35 g, 78% yield) MS APCI (+) m/z 169 (M+1) detected.

Step 1C: Preparation of 7-(2-methoxyethoxy)imidazo[1,2-a]pyridine: A mixture of 4-(2-methoxyethoxy)pyridin-2-amine (20.0 g, 119 mmol), 2-chloroacetaldehyde (32.2 ml, 250 mmol) and tetrahydrofuran (100 mL) were heated in a sealed tube to 75° C. over 3 days. The reaction mixture was concentrated under reduced pressure and dissolved in ethyl acetate. The resulting solution was washed twice sodium bicarbonate. The combined organic layers were dried over $MgSO_4$ and concentrated under reduced pressure to yield title compound (23.5 g, quantitative yield) MS APCI (+) m/z 193 (M+1) detected.

Step 2A: Preparation of N-(2-bromophenyl)cinnamamide: To a mixture of 2-bromobenzenamine (200.0 g, 1163 mmol), pyridine (188.1 ml, 2325 mmol) and dry dichloromethane (1000 ml) at 0° C. was added slowly cinnamoyl chloride (193.7 g, 1163 mmol). The resulting mixture was stirred while warming to ambient temperature overnight. The resulting mixture was washed with sodium bicarbonate (1000 ml), 10% sodium bisulfate (1000 ml), sodium bicarbonate (1000 ml) and brine (1000 ml). The organic layer was dried over $MgSO_4$ and concentrated under reduced pressure to yield title compound as a solid (172.3 gm, 98% yield) MS ESI (+) m/z 224 and 226 (M+1 of each isotope) detected.

Step 2B: Preparation of 8-bromoquinolin-2(1H)-one: A mixture of N-(2-bromophenyl)cinnamamide (172.3 g, 570.3 mmol), aluminum chloride (456 g, 342 mmol) and chlorobenzene (1000 ml) were allowed to stir at 100° C. for 7 hours followed by cooling to ambient temperature overnight. The resulting mixture was poured onto 2 kg of ice and was allowed to warm to ambient temperature over 1 hour. The resulting mixture was extracted with dichloromethane. The combined organic layers were dried over $MgSO_4$ and concentrated under reduced pressure. The resulting solids were triturated with 1000 ml hexanes. The solids were vacuum dried to yield title compound. (83 g, 65% yield) MS ESI (+) m/z 224 and 226 (M+1 of each isotope) detected.

Step 2C: Preparation of 2,8-dibromoquinoline: A mixture of 8-bromoquinolin-2(1H)-one (5 g, 22 mmol) and phosphoryl tribromide (13 g, 45 mmol) was heated to 140° C. for three hours. The resulting mixture was poured onto 100 g of ice and 100 ml water. The mixture was stirred for 1 hour and the resulting solids were filtered to yield the title compound. (5.1 g, 80% yield) MS APCI (+) 286, 288, and 290 (M+1 of each isotope combination) detected.

Step 2D: Preparation of 8-bromo-2-(7-(2-methoxyethoxy) imidazo[1,2-a]pyridin-3-yl)quinoline: A mixture of 2,8-dibromoquinoline (22.4 g, 78.0 mmol), 7-(2-methoxyethoxy) imidazo[1,2-a]pyridine (15.0 g, 78.0 mmol), $Pd(PPh_3)_4$ (4.51 g, 3.90 mmol), $K_2CO_3$ (21.6 g, 156 mmol) and $Pd(OAc)_2$ (0.876 g, 3.90 mmol), dioxane (312 mL) and water (3 ml) was heated to 100° C. for 18 hours. The resulting mixture was diluted with dichloromethane (500 ml) and filtered. The filtrate was concentrated under reduced pressure and to the resulting oil was added ethyl acetate (100 ml) and methyl tert-butyl ether (100 ml). The resulting mixture was stirred overnight. Filtration to collect the resulting solids yielded the title compound (22.2 g, 72% yield). MS ESI (+) m/z 398 and 400 (M+1 of each isotope) detected.

Step 2E: Preparation of (S)-tert-butyl 3-(2-(7-(2-methoxyethoxy)imidazo[1,2-a]pyridin-3-yl)quinolin-8-ylamino)pyrrolidine-1-carboxylate: A stream of argon was passed through a mixture of 8-bromo-2-(7-(2-methoxyethoxy)-imidazo[1,2-a]pyridin-3-yl)quinoline (0.100 g, 0.2511 mmol), (R)-tert-butyl 3-aminopyrrolidine-1-carboxylate (0.05537 ml, 0.3264 mmol), $Cs_2CO_3$ (0.1145 g, 0.3515 mmol), $Pd(OAc)_2$ (0.01127 g, 0.05022 mmol) and rac-BINAP (0.01564 g, 0.02511 mmol) in toluene (1 mL) for 15 minutes. The mixture was heated to 100° C. for 18 hours. The mixture was then allowed to cool to ambient temperature and dichloromethane was added. After stirring 30 minutes, the resulting mixture was filtered and the filtrate was concentrated to yield the title compound as an oil. MS APCI (+) m/z 504.1 (M+1) detected.

Step F: Preparation of (R)-2-(7-(2-methoxyethoxy)imidazo[1,2-a]pyridin-3-yl)-N-(pyrrolidin-3-yl)quinolin-8-amine: To a solution of (S)-tert-butyl 3-(2-(7-(2-methoxyethoxy)imidazo[1,2-a]pyridin-3-yl)quinolin-8-ylamino) pyrrolidine-1-carboxylate (0.127 g, 0.252 mmol) in dichloromethane (2 mL) was added trifluoroacetic acid (0.389 ml, 5.04 mmol). The resulting mixture was stirred for 2 hours at ambient temperature. The dichloromethane reaction mixture was concentrated under reduced pressure and then diluted with dichloromethane. The resulting solution was washed twice with saturated sodium bicarbonate and twice with a brine solution. The organic layer was dried over magnesium sulfate, filtered and concentrated under reduced pressure. Purification via flash column chromatography (40:1 $CH_2Cl_2$/MeOH to 20:1 $CH_2Cl_2$/MeOH to 10:1 $CH_2Cl_2$/MeOH) produced the title compound (53 mg, 52% Yield). MS APCI (+) m/z 404.3 (M+1) detected.

Example 2

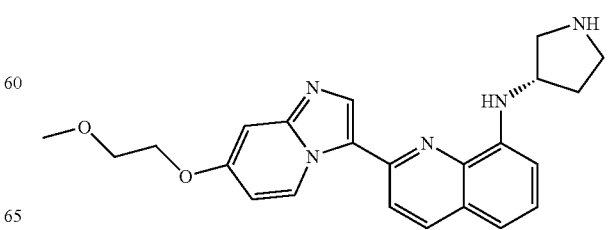

(S)-2-(7-(2-methoxyethoxy)imidazo[1,2-a]pyridin-3-yl)-N-(pyrrolidin-3-yl)quinolin-8-amine Prepared according to the procedure for Example 1 using (S)-tert-butyl 3-aminopyrrolidine-1-carboxylate in place of (R)-tert-butyl 3-aminopyrrolidine-1-carboxylate MS APCI (+) m/z 404.3 (M+1) detected.

Example 3

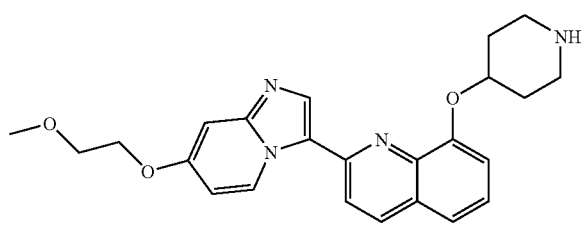

2-(7-(2-methoxyethoxy)imidazo[1,2-a]pyridin-3-yl)-8-(piperidin-4-yloxy)quinoline Step A: 8-(tert-butyldimethylsilyloxy)quinoline-2-carbaldehyde: 8-Hydroxyquinoline-2-carbaldehyde (5.00 g, 28.9 mmol) and imidazole (4.32 g, 63.5 mmol) was dissolved in dichloromethane (50 mL) under an atmosphere of dry $N_2$. The reaction mixture was then cooled to 0° C. and tert-butylchlorodimethylsilane (4.94 g, 31.8 mmol) was added. The reaction was stirred overnight at ambient temperature, and then partitioned between dichloromethane and water. The organic layer was washed with water and aqueous saturated $NaHCO_3$, dried over $Na_2SO_4$, filtered and concentrated under reduced pressure. Purification via flash chromatography (2:1 Hexanes/dichloromethane followed by 1:1 hexanes/dichloromethane) provided 6.50 g, 78% of the desired product as an oil.

Step B: (E)-8-(tert-butyldimethylsilyloxy)-2-(2-methoxyvinyl)quinoline: Methoxymethyl triphenylphosphonium chloride (3.94 g, 11.5 mmol) was suspended in anhydrous THF (25 mL) under an atmosphere of dry $N_2$. After cooling to 0° C., potassium tert-butoxide (1.41 g, 12.5 mmol) was added. The solution was stirred at 0° C. for 5 minutes, then warmed to ambient temperature. After 15 minutes 8-(tert-butyldimethylsilyloxy)quinoline-2-carbaldehyde (3.00 g, 10.4 mmol) was added. The reaction was stirred at ambient temperature overnight, and then concentrated under vacuum. Diethyl ether (200 mL) was added, and the mixture was stirred at ambient temperature for 1 hour and then filtered. The precipitate was washed with diethyl ether and the filtrate was collected and concentrated under vacuum. The resulting residue was dissolved in diethyl ether (50 mL) to which hexanes (50 mL) was added. The mixture was stirred for 1 hour and then filtered. The filtrate was concentrated under vacuum to give 3.12 g, 95% of the desired product as a mixture of cis-trans isomers.

Step C: 2-(7-(2-methoxyethoxy)imidazo[1,2-a]pyridin-3-yl)quinolin-8-ol: (E)-8-(tert-butyldimethylsilyloxy)-2-(2-methoxyvinyl)quinoline (1.90 g, 6.02 mmol) was dissolved in a solution of THF (20 mL) and water (3 mL). N-bromosuccinimide (1.13, 6.32 mmol) was added to the reaction mixture. After the reaction was judged to be complete (monitored by MS), 4-(2-methoxyethoxy)pyridin-2-amine 1.01 g, 6.02 mmol) was added. The reaction was then heated to reflux for 5 hours and then cooled to ambient temperature. To the reaction mixture was added 10 ml of 1.0 M tetrabutylammonium fluoride in THF. The reaction mixture was stirred at ambient temperature for 1 hour and then diluted with water. The mixture was extracted with 1:4 isopropyl acetate:dichloromethane. The combined organic phase was dried (sodium sulfate), filtered and condensed under reduced pressures. The residue was purified by flash chromatography, eluting with gradient from 100% EtOAc to 10% MeOH (w/6% $NH_4OH$)/EtOAc to obtain 700 mg of the desired product as a red solid.

Step D: tert-butyl 4-(2-(7-(2-methoxyethoxy)imidazo[1,2-a]pyridin-3-yl)quinolin-8-yloxy)piperidine-1-carboxylate: 2-(7-(2-Methoxyethoxy)imidazo[1,2-a]pyridin-3-yl)quinolin-8-ol (0.030 g, 0.0895 mmol), tert-butyl 4-hydroxypiperidine-1-carboxylate (0.0198 g, 0.0984 mmol), triphenylphosphine (0.0352 g, 0.134 mmol) and diethyl azodicarboxylate (0.0211 ml, 0.134 mmol) were combined in anhydrous THF (1 mL). The reaction mixture was stirred overnight at ambient temperature, then diluted with EtOAc and washed with saturated $NaHCO_3$ and brine, dried ($Na_2SO_4$), filtered and concentrated under reduced pressure. The residue was purified via flash column chromatography (dichloromethane followed by 40:1 dichloromethane/MeOH) which provided 29.0 mg of the desired product as a brown residue.

Step E: 2-(7-(2-methoxyethoxy)imidazo[1,2-a]pyridin-3-yl)-8-(piperidin-4-yloxy)quinoline: Trifluoroacetic acid 0.0862 ml, 1.12 mmol) was added to a solution of tert-butyl 4-(2-(7-(2-methoxyethoxy)imidazo[1,2-a]pyridin-3-yl)quinolin-8-yloxy)piperidine-1-carboxylate (0.029 g, 0.0559 mmol) in dichloromethane (0.50 mL). After stirring overnight at ambient temperature, the reaction mixture was concentrated under reduced pressure and partitioned between dichloromethane and saturated $NaHCO_3$. The organic layer was washed with saturated $NaHCO_3$ and brine, dried ($Na_2SO_4$), filtered and concentrated under reduced pressure. The residue was purified via flash column chromatography (40:1 dichloromethane/MeOH followed by 5:1 dichloromethane/MeOH followed by 2:1 dichloromethane/MeOH) provided 10.0 mg of the desired compound. MS APCI (+) m/z 419.2 (M+1) detected.

Example 4

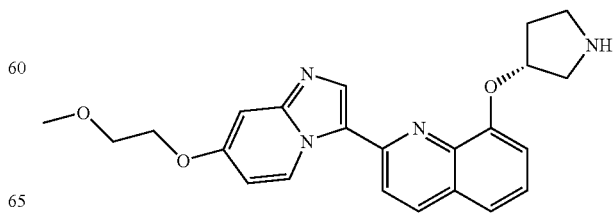

(R)-2-(7-(2-methoxyethoxy)imidazo[1,2-a]pyridin-3-yl)-8-(pyrrolidin-3-yloxy)quinoline Prepared according to the procedure for Example 3 using (S)-tert-butyl 3-hydroxypyrrolidine-1-carboxylate in place of tert-butyl 4-hydroxypiperidine-1-carboxylate. MS APCI (+) m/z 405.2 (M+1) detected.

Example 5

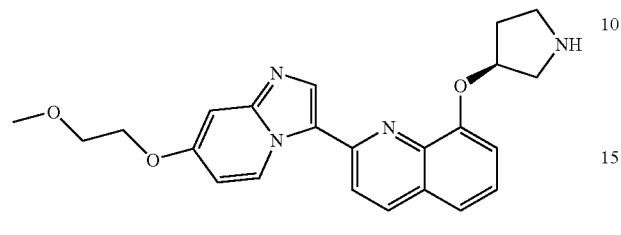

(S)-2-(7-(2-methoxyethoxy)imidazo[1,2-a]pyridin-3-yl)-8-(pyrrolidin-3-yloxy)quinoline Prepared according to the procedure for Example 3 using (R)-tert-butyl 3-hydroxypyrrolidine-1-carboxylate in place of tert-butyl 4-hydroxypiperidine-1-carboxylate. MS APCI (+) m/z 405.2 (M+1) detected.

Example 6

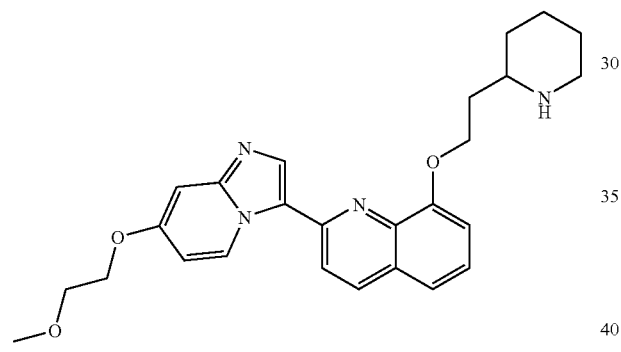

2-(7-(2-Methoxyethoxy)imidazo[1,2-a]pyridin-3-yl)-8-(2-(piperidin-2-yl)ethoxy)quinoline Prepared according to the procedure for Example 3 using the appropriate amine-protected 2-(piperidin-2-yl)ethanol. MS APCI (+) m/z 447.3 (M+1) detected.

Example 7

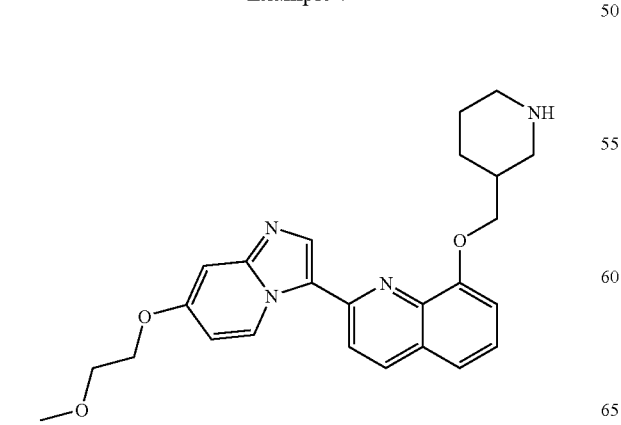

2-(7-(2-Methoxyethoxy)imidazo[1,2-a]pyridin-3-yl)-8-(piperidin-3-ylmethoxy)quinoline Prepared according to the procedure for Example 3 using the appropriate amine-protected piperidin-3-ylmethanol. MS APCI (+) m/z 433.3 (M+1) detected.

Example 8

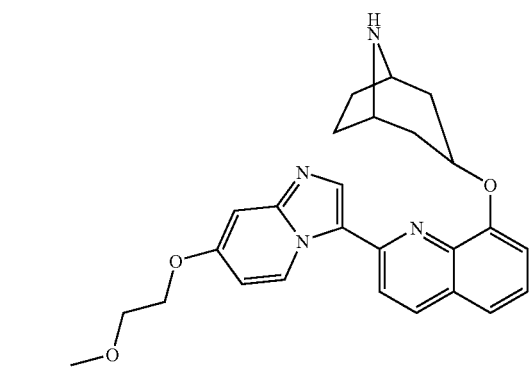

8-(8-Azabicyclo[3.2.1]octan-3-yloxy)-2-(7-(2-methoxyethoxy)imidazo[1,2-a]pyridin-3-yl)quinoline Prepared according to the procedure for Example 3 using the amine-protected 8-azabicyclo[3.2.1]octan-3-ol. MS APCI (+) m/z 445.2 (M+1) detected.

Example 9

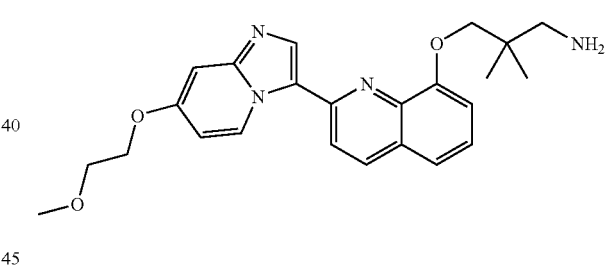

3-(2-(7-(2-Methoxyethoxy)imidazo[1,2-a]pyridin-3-yl)quinolin-8-yloxy)-2,2-dimethylpropan-1-amine Prepared according to the procedure for Example 3 using the appropriate amine-protected 3-amino-2,2-dimethylpropan-1-ol. MS APCI (+) m/z 421.2 (M+1) detected.

Example 10

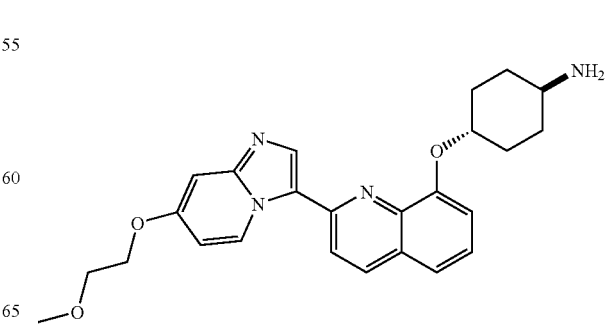

(1R, 4R)-4-(2-(7-(2-Methoxyethoxy)imidazo[1,2-a]pyridin-3-yl)quinolin-8-yloxy)cyclohexanamine Prepared according to the procedure for Example 3 using the appropriate amine-protected (1R,4R)-4-aminocyclohexanol. MS APCI (+) m/z 433.1 (M+1) detected.

Example 11

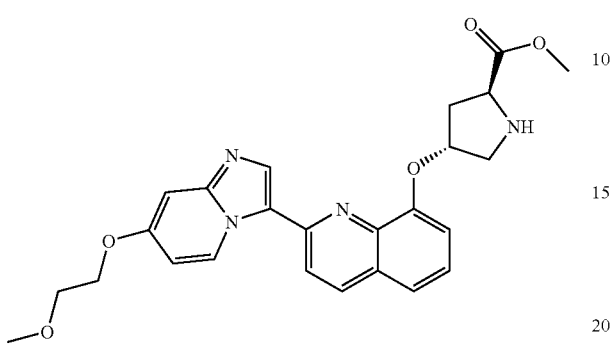

(2S,4R)-Methyl-4-(2-(7-(2-methoxyethoxy)imidazo[1,2-a]pyridin-3-yl)quinolin-8-yloxy)pyrrolidine-2-carboxylate Prepared according to the procedure for Example 3 using the appropriate amine-protected (2S,4R)-methyl 4-hydroxypyrrolidine-2-carboxylate. MS APCI (+) m/z 463.2 (M+1) detected.

Example 12

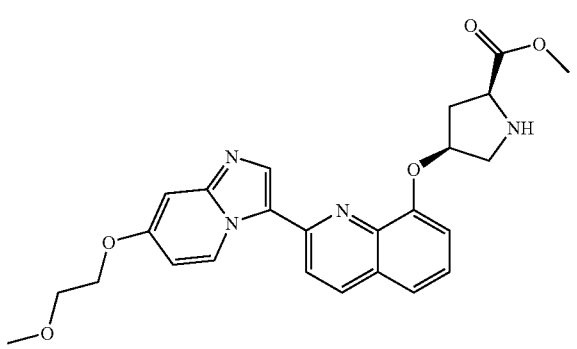

(2S,4S)-Methyl 4-(2-(7-(2-methoxyethoxy)imidazo[1,2-a]pyridin-3-yl)quinolin-8-yloxy)pyrrolidine-2-carboxylate Prepared according to the procedure for Example 3 using the appropriate amine-protected (2S,4S)-methyl 4-hydroxypyrrolidine-2-carboxylate. MS APCI (+) m/z 463.2 (M+1) detected.

Example 13

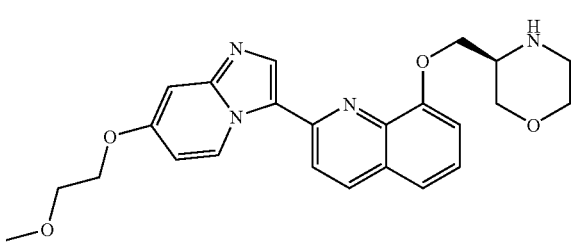

(S)-3-((2-(7-(2-Methoxyethoxy)imidazo[1,2-a]pyridin-3-yl)quinolin-8-yloxy)methyl)morpholine Prepared according to the procedure for Example 3 using the appropriate amine-protected (R)-morpholin-3-ylmethanol. MS ESI (+) m/z 435.2 (M+1) detected.

Example 14

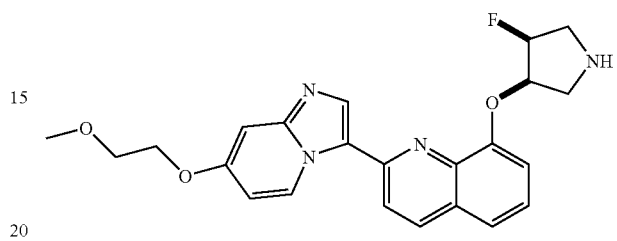

8-((cis)-4-fluoropyrrolidin-3-yloxy)-2-(7-(2-methoxyethoxy)imidazo[1,2-a]pyridin-3-yl)quinoline hydrochloride salt Step A: Preparation of benzyl 6-oxa-3-azabicyclo[3.1.0]hexane-3-carboxylate: Benzyl 2,5-dihydro-1H-pyrrole-1-carboxylate (11.0 g, 54.1 mmol, commercially available from Aldrich) and 3-chlorobenzoperoxoic acid (17.3 g, 70.4 mmol) were added to 150 mL of chloroform and heated to 46° C. for 20 hours. The mixture was cooled, dichloromethane was added, and the reaction was washed with a saturated solution of NaHCO₃ and Na₂S₂CO₃. The combined organic layers were dried over MgSO₄, filtered and concentrated to give 10.5 g (88% isolated yield) of the desired compound as an oil, which was used directly in the next step.

Step B: Preparation of (trans)-benzyl 3-fluoro-4-hydroxypyrrolidine-1-carboxylate: benzyl 6-oxa-3-azabicyclo[3.1.0]hexane-3-carboxylate (10.5 g, 47.9 mmol) and pyridine-hydrogen fluoride (14.2 g, 144.0 mmol) were added to a Teflon bottle containing dichloromethane and stirred vigorously overnight. After 20 hours, the reaction was slowly and carefully quenched with excess saturated solution of NaHCO₃ over several minutes and allowed to stir for one hour, and then the organic layer was isolated and washed with NaHCO₃ and a solution of brine. The combined organic layers were dried over MgSO₄, filtered and evaporated to yield an oil. This crude oil was purified on silica gel using ethyl acetate-hexane to produce 2.0 g (17% isolated yield) of the desired product as an oil.

Step C: Preparation of (trans)-benzyl 3-fluoro-4-(methylsulfonyloxy)pyrrolidine-1-carboxylate: (trans)-Benzyl 3-fluoro-4-hydroxypyrrolidine-1-carboxylate (2.0 g, 8.36 mmol) was added to dichloromethane and cooled to 0° C. Methanesulfonyl chloride (1.30 mL, 16.7 mmol) and triethylamine (2.3 mL, 16.7 mmol) were sequentially added, and the reaction was allowed to warm to ambient temperature overnight under vigorous stirring. The following day, additional dichloromethane was added, and the reaction mixture was washed with a saturated solution of NaHCO₃. The combined organic layers were dried over MgSO₄, filtered and evaporated. The crude oil was purified on silica gel using ethyl acetate and hexane to produce 2.0 g (70% isolated yield) of the desired product as an oil.

Step D: Preparation of (cis)-benzyl 3-fluoro-4-(2-(7-(2-methoxyethoxy)imidazo[1,2-a]pyridin-3-yl)quinolin-8-yloxy)pyrrolidine-1-carboxylate: 2-(7-(2-Methoxyethoxy)imidazo[1,2-a]pyridin-3-yl)quinolin-8-ol (1.75 g, 5.22 mmol), (trans)-benzyl 3-fluoro-4-(methylsulfonyloxy)pyrrolidine-1-carboxylate (1.99 g, 6.3 mmol) and cesium carbonate (3.40 g, 10.4 mmol) were added to a sealed tube containing dimethylacetamide and heated to 100° C. overnight with stirring. The dimethylacetamide was removed under vacuum concentration and heat, chloroform was added, and this organic phase was gently washed with water. The combined organic layers were dried over $MgSO_4$, filtered and evaporated. The crude material was purified on silica gel using a 6% solution of ammonium hydroxide in methanol and dichloromethane to yield three major products which could not be separated further by column purification (starting quinoline phenol, product and unidentified by-product). MS APCI (+) m/z 557.3 (M+1) detected. This crude material was taken directly on to the deprotection step.

Step E: Preparation of 8-((cis)-4-fluoropyrrolidin-3-yloxy)-2-(7-(2-methoxyethoxy)imidazo[1,2-a]pyridin-3-yl)quinoline hydrochloride salt: Crude (cis)-benzyl 3-fluoro-4-(2-(7-(2-methoxyethoxy)imidazo[1,2-a]pyridin-3-yl)quinolin-8-yloxy)pyrrolidine-1-carboxylate (1.0 g, 2.0 mmol) and palladium on carbon (1 g, 50% on a molar basis) were added to a mixture of ethanol and 1% HCl (v/v) and placed under hydrogen in a balloon with vigorous stirring. After 18 hours, the crude mixture was passed through Celite, rinsed several times with ethanol, and the collected filtrate was evaporated. The crude material was purified on silica gel using a 6% solution of ammonium hydroxide in methanol and dichloromethane to yield free base product, which, when subjected to HCl in dichloromethane and subsequent precipitation in diethyl ether yielded 150 mg (16% isolated yield) of highly pure product. MS APCI (+) m/z 423.3 (M+1) detected.

Example 15

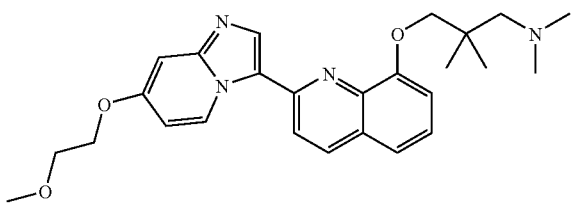

3-(2-(7-(2-methoxyethoxy)imidazo[1,2-a]pyridin-3-yl)quinolin-8-yloxy)-N,N,2,2-tetramethylpropan-1-amine Prepared according to Example 3, substituting 3-(dimethylamino)-2,2-dimethylpropan-1-ol for tert-butyl 4-hydroxypiperidine-1-carboxylate (50 mg, 0.15 mmol)] MS ESI (+) m/z 449.2 (M+1) detected.

Example 16

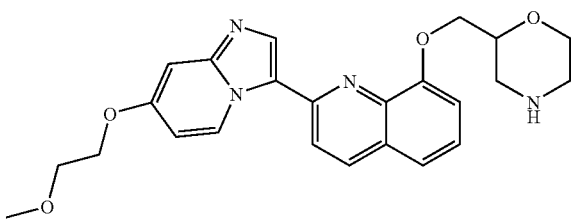

2-((2-(7-(2-methoxyethoxy)imidazo[1,2-a]pyridin-3-yl)quinolin-8-yloxy)methyl)morpholine To a solution of 2-(7-(2-methoxyethoxy)imidazo[1,2-a]pyridin-3-yl)quinolin-8-ol [prepared as in Example 3, Step C; 50 mg, 0.15 mmol] in anhydrous DMA (2 mL) was added cesium carbonate (150 mg, 0.45 mmol) followed by tert-butyl 2-((methylsulfonyloxy)methyl)morpholine-4-carboxylate (130 mg, 0.45 mmol). The heterogeneous mixture was stirred at 100° C. for 16 hours and allowed to cool. The mixture was treated with water (20 mL) and extracted with EtOAc. The combined organic phases were washed with water and brine, then dried over $Na_2SO_4$, filtered and concentrated. The residue was purified via flash column chromatography using gradient elution ($CH_2Cl_2$ to 1% $MeOH/CH_2Cl_2$ to 2% $MeOH/CH_2Cl_2$) to afford tert-butyl 2-((2-(7-(2-methoxyethoxy)imidazo[1,2-a]pyridin-3-yl)quinolin-8-yloxy)methyl)morpholine-4-carboxylate as a gum. This was dissolved in $CH_2Cl_2$ (4 mL) and treated with TFA (1 mL). After stirring for 2 hours at ambient temperature the mixture was concentrated. The residue was triturated with ether, filtered and dried in vacuo to provide 29.1 mg (76%) of desired product as its di-TFA salt as a powder. MS ESI (+) m/z 435.3 (M+1) detected.

Example 17

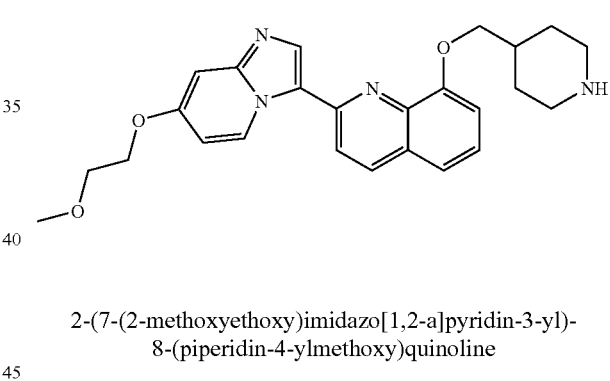

2-(7-(2-methoxyethoxy)imidazo[1,2-a]pyridin-3-yl)-8-(piperidin-4-ylmethoxy)quinoline Prepared according to the procedure for Example 16, using tert-butyl 4-((methylsulfonyloxy)methyl)piperidine-1-carboxylate in place of tert-butyl 2-((methylsulfonyloxy)methyl)morpholine-4-carboxylate. MS ESI (+) m/z 433.1 (M+1) detected.

Example 18

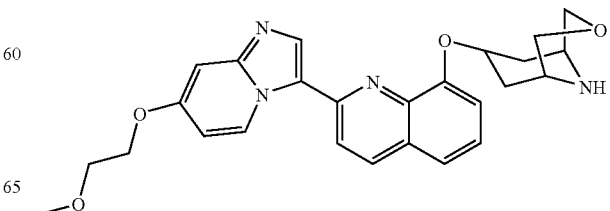

7-(2-(7-(2-methoxyethoxy)imidazo[1,2-a]pyridin-3-yl)quinolin-8-yloxy)-3-oxa-9-azabicyclo[3.3.1]nonane Prepared according to the procedure for Example 16, using tert-butyl 7-(methylsulfonyloxy)-3-oxa-9-azabicyclo[3.3.1]nonane-9-carboxylate in place of tert-butyl 2-((methylsulfonyloxy)methyl)morpholine-4-carboxylate. MS APCI (+) m/z 461.2 (M+1) detected.

Example 19

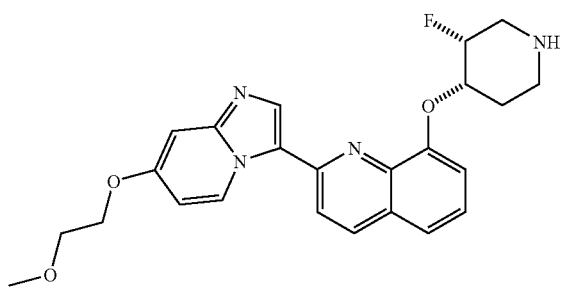

8-((cis)-3-fluoropiperidin-4-yloxy)-2-(7-(2-methoxyethoxy)imidazo[1,2-a]pyridin-3-yl)quinoline Prepared according to the procedure for Example 16, using (trans)-tert-butyl 3-fluoro-4-(methylsulfonyloxy)piperidine-1-carboxylate in place of tert-butyl 2-((methylsulfonyloxy)methyl)morpholine-4-carboxylate. MS ESI (+) m/z 437.2 (M+1) detected.

Example 20

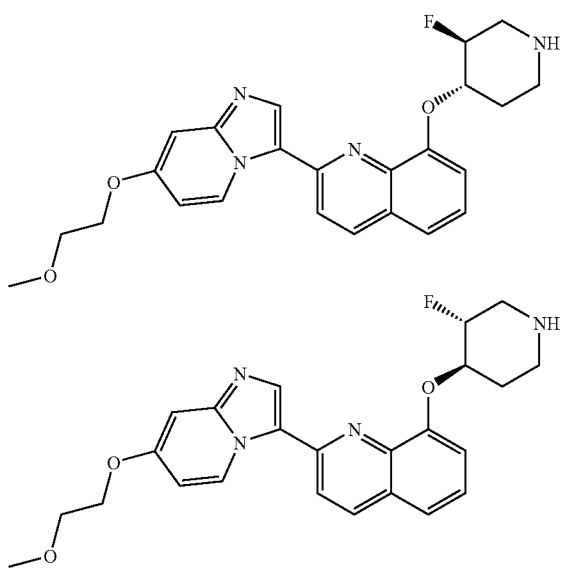

8-((3S,4S)-3-fluoropiperidin-4-yloxy)-2-(7-(2-methoxyethoxy)imidazo[1,2-a]pyridin-3-yl)quinoline and 8-((3R,4R)-3-fluoropiperidin-4-yloxy)-2-(7-(2-methoxyethoxy)imidazo[1,2-a]pyridin-3-yl)quinoline Step A: Preparation of tert-butyl 4-(trimethylsilyloxy)-5,6-dihydropyridine-1(2H)-carboxylate: To a solution of t-butyl 4-oxopiperidine-1-carboxylate (52.6 g, 264 mmol) in anhydrous DMF (140 mL) was added TMSCl (40.2 mL, 317 mmol) followed by triethylamine (88.3 mL, 634 mmol). The resulting heterogeneous mixture was warmed to 80° C. and stirred for 16 hours. The cooled mixture was diluted with hexanes (500 mL), washed with saturated NaHCO₃ (3×300 mL) and brine (200 mL), then dried over Na₂SO₄, filtered and concentrated to afford 68 g (95%) of desired product as an oil.

Step B: Preparation of tert-butyl 3-fluoro-4-oxopiperidine-1-carboxylate: To a solution of tert-butyl 4-(trimethylsilyloxy)-5,6-dihydropyridine-1(2H)-carboxylate (64.4 g, 237 mmol) in anhydrous ACN (1.5 L) at ambient temperature was added Selectfluor (92.5 g, 261 mmol) portion wise over 10 minutes, during which a slight exotherm (to 40° C.) was observed. The mixture was stirred for 2 hours, then concentrated to dryness and partitioned between EtOAc and brine. The aqueous layer was extracted with EtOAc and the combined organic phases were washed with brine, dried over Na₂SO₄, filtered and concentrated to afford 51 g (99%) of desired product as a solid.

Step C: Preparation of 3-fluoropiperidin-4-one hydrochloride: To a hazy solution of tert-butyl 3-fluoro-4-oxopiperidine-1-carboxylate (52.66 g, 242 mmol) in EtOAc (1 L) was added 4M HCl/dioxane (303 mL, 1212 mmol). The mixture was allowed to stir at ambient temperature for 16 hours. The resulting precipitate was collected by filtration, washed with EtOAc and dried in vacuo to afford 37 g (99%) of desired product as a solid.

Step D: Preparation of naphthalen-2-ylmethyl 3-fluoro-4-oxopiperidine-1-carboxylate: To a suspension of 3-fluoropiperidin-4-one hydrochloride (35.66 g, 232.2 mmol) in THF (800 mL) at 0° C. was added a solution of NaHCO₃ (46.81 g, 557.3 mmol) in water (800 mL). After most of the bubbling had subsided the ensuing solution was treated with a solution of naphthalen-2-ylmethyl carbonochloridate (56.36 g, 255.4 mmol) in THF (300 mL) dropwise, over 30 minutes. The mixture was allowed to warm to ambient temperature over 16 hours with vigorous stirring. The mixture was diluted with water and extracted with EtOAc. The combined organic phases were washed with brine, then dried over Na₂SO₄, filtered arid concentrated. The residue was triturated with methanol and the resulting solid was filtered and dried in vacuo to afford 41.8 g (60%) of desired product as a cream-colored powder.

Step E: Preparation of (cis)-naphthalen-2-ylmethyl 3-fluoro-4-hydroxypiperidine-1-carboxylate: To a suspension of naphthalen-2-ylmethyl 3-fluoro-4-oxopiperidine-1-carboxylate (41.75 g, 138.6 mmol) in anhydrous THF (800 mL) at 0° C. was added L-Selectride (346 mL, 1.0 M, 346 mmol) dropwise over 30 minutes, during which a yellow solution formed. The solution was allowed to warm to ambient temperature and stir for 16 hours. The mixture was cooled to 0° C., then treated with methanol (160 mL) and 2 N NaOH (350 mL) followed by the dropwise addition of 30% H₂O₂ (160 mL), during which an exotherm was observed. After stirring at 0° C. for an additional 1 hour and then at ambient temperature for 3 hours, the mixture was extracted with EtOAc. The combined organic phases were washed with brine, dried over Na₂SO₄, filtered and concentrated. The residue was purified on a large silica gel plug eluting with hexanes:EtOAc, 1:1 to afford 26.78 g (64%) of desired product as a solid.

A 2 g sample of the material of Step E was separated by chiral HPLC (3 cm×250 mm Chiral Technologies IA column; mobile phase 15% Ethanol, 85% hexanes; flow rate 28 mL/min; 50 mg/mL injections; 254 and 220 nM) to afford first eluting peak (Peak 1, 616 mg, Rt 17.70 min) in >99% ee and second eluting peak (Peak 2, 639 mg, Rt 22.12 min) in >99% ee, both as white solids. The material obtained from peak 1 was arbitrarily assigned as (3S,4R)-naphthalen-2-ylmethyl 3-fluoro-4-hydroxypiperidine-1-carboxylate. The material obtained from peak 2 was arbitrarily assigned as (3R,4S)-naphthalen-2-ylmethyl 3-fluoro-4-hydroxypiperidine-1-carboxylate.

Step F: Preparation of (3S,4R)-naphthalen-2-ylmethyl 3-fluoro-4-(methylsulfonyloxy)piperidine-1-carboxylate and (3R,4S)-naphthalen-2-ylmethyl 3-fluoro-4-(methylsulfonyloxy)piperidine-1-carboxylate: To a solution of naphthalen-2-ylmethyl 3-fluoro-4-hydroxypiperidine-1-carboxylate (Peak 1), (616 mg, 2.03 mmol) in anhydrous $CH_2Cl_2$ (30 mL) at 0° C. was added triethylamine (368 μL, 2.64 mmol) followed by mesyl chloride (173 μL, 2.23 mmol). The mixture was allowed to warm slowly to ambient temperature over 16 hours, then treated with $Et_3N$ (200 μL) and mesyl chloride (100 μL) and stirred for an additional 1 hour. The mixture was partitioned between $CH_2Cl_2$ (30 mL) and saturated $NaHCO_3$ (30 mL) and the aqueous layer was extracted with $CH_2Cl_2$. The combined organic phases were washed with brine, dried over $Na_2SO_4$, filtered and concentrated. The residue was purified via flash column chromatography (hexanes:EtOAc, 2:1) to afford 540 mg (70%) of desired product as a solid.

The compound of step E designated as Peak 2 (639 mg, 2.11 mmol) was treated in the same way to afford 616 mg (77%) of desired product as a white solid.

Step G: Preparation of (3S,4S)-naphthalen-2-ylmethyl 3-fluoro-4-(2-(7-(2-methoxyethoxy)imidazo[1,2-a]pyridin-3-yl)quinolin-8-yloxy)piperidine-1-carboxylate and (3R,4R)-naphthalen-2-ylmethyl 3-fluoro-4-(2-(7-(2-methoxyethoxy)imidazo[1,2-a]pyridin-3-yl)quinolin-8-yloxy)piperidine-1-carboxylate: To a solution of 2-(7-(2-methoxyethoxy)imidazo[1,2-a]pyridin-3-yl)quinolin-8-ol (prepared as in Example 3, 390 mg, 1.16 mmol) in anhydrous DMF (5 mL) was added cesium carbonate (1.14 g, 3.49 mmol) followed by naphthalen-2-ylmethyl 3-fluoro-4-(methylsulfonyloxy)piperidine-1-carboxylate (Peak 1) (532 mg, 1.40 mmol). The heterogeneous mixture was warmed to 90° C. and stirred for 6 hours. The cooled mixture was treated with water (50 mL) and extracted with EtOAc. The combined organic phases were washed with water and brine, then dried over $Na_2SO_4$, filtered and concentrated. The residue was purified via flash column chromatography using gradient elution ($CH_2Cl_2$ to 2% MeOH/$CH_2Cl_2$) to afford 293 mg (41%) of the Peak 1 desired product as a glass. MS APCI (+) m/z 621.2 (M+1) detected.

The (Peak 2) naphthalen-2-ylmethyl 3-fluoro-4-(methylsulfonyloxy)piperidine-1-carboxylate (450 mg, 1.34 mmol) was treated in the same way to afford 325 mg (39%) of the Peak 2 desired product as a pale yellow glass. MS APCI (+) m/z 621.2 (M+1) detected.

Step H: Preparation of 8-((3S,4S)-3-fluoropiperidin-4-yloxy)-2-(7-(2-methoxyethoxy)imidazo[1,2-a]pyridin-3-yl)quinoline and 8-((3R,4R)-3-fluoropiperidin-4-yloxy)-2-(7-(2-methoxyethoxy)imidazo[1,2-a]pyridin-3-yl)quinoline:
To a solution of the (Peak 1) naphthalen-2-ylmethyl 3-fluoro-4-(2-(7-(2-methoxyethoxy)imidazo[1,2-a]pyridin-3-yl)quinolin-8-yloxy)piperidine-1-carboxylate (293 mg, 0.47 mmol) in a 1:1 mixture of EtOH:EtOAc (20 mL) was added 10% Pd/C (wet, Degussa type, 30 mg). The mixture was purged with argon then allowed to stir under a balloon of $H_2$ for 16 hours. The mixture was treated with a further 20 mg of catalyst, recharged and hydrogenated for a further 16 hours. The mixture was filtered through GF paper and concentrated in vacuo. The residue was purified via flash column chromatography using gradient elution ($CH_2Cl_2$ to 2% MeOH/ $CH_2Cl_2$ to 5% MeOH/$CH_2Cl_2$) to afford 128 mg (62%) of desired product as a solid. MS APCI (+) m/z 437.2 (M+1) detected.

The (Peak 2) naphthalen-2-ylmethyl 3-fluoro-4-(2-(7-(2-methoxyethoxy)imidazo[1,2-a]pyridin-3-yl)quinolin-8-yloxy)piperidine-1-carboxylate (325 mg, 0.52 mmol) was treated in the same way to afford 128 mg (56%) of desired product as a pale yellow solid. MS APCI (+) m/z 437.2 (M+1) detected. Chiral HPLC analysis confirmed that the ee's were maintained and the elution order for final peaks was consistent with those of the alcohols from Step E.

Example 21

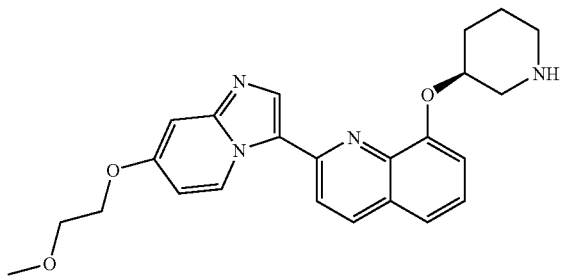

(S)-2-(7-(2-methoxyethoxy)imidazo[1,2-a]pyridin-3-yl)-8-(piperidin-3-yloxy)quinoline Prepared according to the procedure for Example 16, using (R)-tert-butyl 3-(methylsulfonyloxy)piperidine-1-carboxylate in place of tert-butyl 2-((methylsulfonyloxy)methyl)morpholine-4-carboxylate. MS ESI (+) m/z 419.1 (M+1) detected.

Example 22

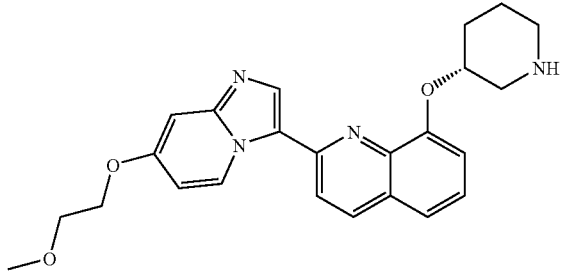

(R)-2-(7-(2-methoxyethoxy)imidazo[1,2-a]pyridin-3-yl)-8-(piperidin-3-yloxy)quinoline Prepared according to the procedure for Example 16, using (S)-tert-butyl 3-(methylsulfonyloxy)piperidine-1-carboxylate in place of tert-butyl 2-((methylsulfonyloxy)methyl)morpholine-4-carboxylate. MS ESI (+) m/z 419.1 (M+1) detected.

Example 23

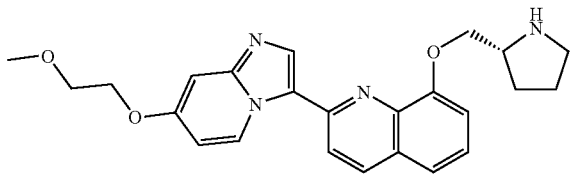

(R)-2-(7-(2-methoxyethoxy)imidazo[1,2-a]pyridin-3yl)-8-(pyrrolidin-2-ylmethoxy)quinoline Step A: Preparation of (R)-tert-butyl 2-((2-(7-(2-methoxyethoxy)imidazo[1,2-a]pyridin-3-yl)quinolin-8-yloxy)methyl)pyrrolidine-1-carboxylate: Prepared according to the procedure for Example 14 Step D, substituting (R)-tert-butyl 2-(tosyloxymethyl)pyrrolidine-1-carboxylate for (trans)-benzyl 3-fluoro-4-(methylsulfonyloxy)pyrrolidine-1-carboxylate.

Step B: Preparation of (R)-2-(7-(2-methoxyethoxy)imidazo[1,2-a]pyridin-3-yl)-8-(pyrrolidin-2-ylmethoxy)quinoline: (R)-tert-butyl 2-((2-(7-(2-methoxyethoxy)imidazo[1,2-a]pyridin-3-yl)quinolin-8-yloxy)methyl)pyrrolidine-1-carboxylate (241 mg, 0.47 mmol) was dissolved in 10 mL of chloroform, followed by addition of 4.0M HCl in dioxane (4.65 ml, 9.3 mmol). The reaction was allowed to stir for 30 hours at ambient temperature at which time all starting material was consumed by LC/TLC. The reaction was concentrated in vacuo, followed by flash column chromatography (eluting with a 1-20% MeOH/DCM gradient), affording an oil on concentration. The crude oil was treated with 1000 uL of 4.0 M HCl in dioxane, affording the desired product (80 mg, 41% yield). MS APCI (+) m/z 419.1 (M+1) detected.

Example 24

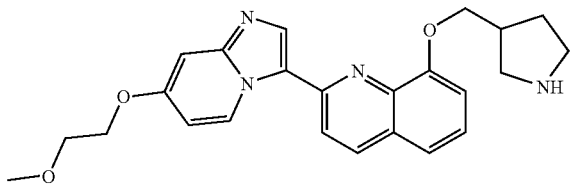

2-(7-(2-methoxyethoxy)imidazo[1,2-a]pyridin-3-yl)-8-(pyrrolidin-3-ylmethoxy)quinoline To a solution of 2-(7-(2-methoxyethoxy)imidazo[1,2-a]pyridin-3-yl)quinolin-8-ol [prepared as in Example 16; 204 mg, 0.61 mmol] in anhydrous DMA (5 mL) was added cesium carbonate (0.60 g, 1.8 mmol) followed by tert-butyl 3-((methylsulfonyloxy)methyl)pyrrolidine-1-carboxylate (221 mg, 0.79 mmol). The heterogeneous mixture was stirred at 70° C. for 20 hours and allowed to cool. The mixture was treated with water (50 mL) and extracted with chloroform and EtOAc. The combined organic extracts were dried over anhydrous Na₂SO₄, filtered and concentrated to afford the crude product (386 mg, 122% yield) as a viscous oil. MS ESI (+) m/z 519.1 (M+1) detected. The oil (315 mg) was dissolved in CH₂Cl₂ (2 mL) and treated with TFA (1 mL). After stirring for 2 hours at ambient temperature the mixture was concentrated. The residue was treated with excess (20 ml) saturated aqueous sodium bicarbonate solution, and the resulting mixture was extracted with chloroform and EtOAc. The combined organic extracts were dried over anhydrous Na₂SO₄ and concentrated to afford a viscous oil. The oil was purified by column chromatography on silica gel (elution with 7 N NH₃/MeOH-chloroform) to provide the title compound (74 mg, 36% yield over two steps) as a solid. MS ESI (+) m/z 419.3 (M+1). detected.

Example 25

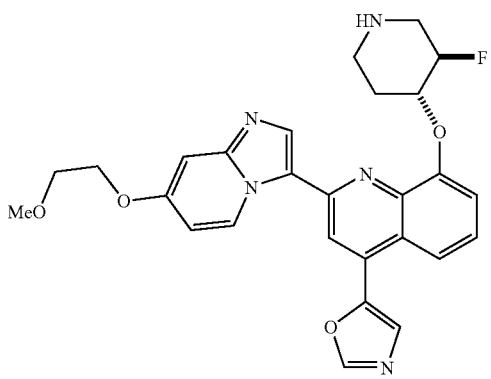

5-(8-((trans)-3-fluoropiperidin-4-yloxy)-2-(7-(2-methoxyethoxy)imidazo[1.2-a]pyridin-3-yl)quinolin-4-yl)oxazole 1. Preparation of tert-butyl 2-ethynyl-6-methoxyphenylcarbamate Step 1A: Preparation of tert-butyl 2-iodo-6-methoxyphenylcarbamate: To tert-butyl 2-methoxyphenylcarbamate (24.1 g, 108 mmol) in dry Et₂O (100 mL) at −20° C. was added dropwise tert-butyllithium (140 ml, 237 mmol). The clear solution turned cloudy at the end of the addition. The reaction was stirred for 3 hours at −20° C., then cooled to −100° C. with a liquid N₂/Et₂O bath. Iodine (27.4 g, 108 mmol) in Et₂O (250 mL) was added to the solution. Following addition of I₂, the reaction was slowly warmed to ambient temperature over night. Na₂S₂O₃ (saturated, 200 mL) was then added to the reaction mix and phases were separated. The aqueous was extracted with Et₂O, and the combined organic layers were dried (MgSO₄), filtered and concentrated. DCM (50 mL) was added, followed by hexanes (200 mL). The solution was concentrated to remove DCM. The product crashed out, and was collected by filtration and washed with hexanes (100 mL) to give the crude product (58%).

Step 1B: Preparation of tert-butyl 2-methoxy-6-((trimethylsilyl)ethynyl)phenylcarbamate: To tert-butyl 2-iodo-6-methoxyphenylcarbamate (10.36 g, 29.67 mmol), ethynyltrimethylsilane (3.20 g, 32.63 mmol), copper(I) iodide (0.28 g, 1.48 mmol), and PdCl₂(PPh₃)₂ (1.04 g, 1.48 mmol) in THF (100 mL) was added triethylamine (3.60 g, 35.6 mmol), followed by overnight stirring. The crude reaction was then concentrated and the mixture was flashed through silica gel with 10:1 Hex/EtOAc to give the desired product (98%).

Step 1C: Preparation of tert-butyl 2-ethynyl-6-methoxyphenylcarbamate: To tert-butyl 2-methoxy-6-((trimethylsilyl)ethynyl)phenylcarbamate (4.21 g, 13.2 mmol) in MeOH (30 mL) was added K₂CO₃ (9.11 g, 65.9 mmol). The reaction was stirred for 30 minutes, then filtered and washed with DCM (50 mL). The combined organic layers were concentrated and diluted with DCM (20 mL), filtered, washed a second time with DCM (50 mL), then concentrated. The residue was purified by flash chromatography through a pad of silica gel with 10:1 Hexane/EtOAc (500 mL), affording the desired product (62%).

2. Preparation of N-methoxy-7-(2-methoxyethoxy)-N-methylimidazo[1,2-a]pyridine-3-carboxamide Step 2A: Preparation of ethyl 7-(2-methoxyethoxy)imidazo[1,2-a]pyridine-3-carboxylate: Ethyl 2-chloro-3-oxopropanoate (5.1 g, 33.9 mmol, Heterocycles 1991, pg. 699) and 4-(2-methoxyethoxy)pyridin-2-amine (5.70 g, 33.9 mmol) was dissolved in EtOH (50 mL) and heated to reflux overnight. The crude reaction mixture was concentrated and purified by flash column chromatography (EtOAc/MeOH 10:0 to 10:1) provided the desired product (57%).

Step 2B: Preparation of 7-(2-methoxyethoxy)imidazo[1,2-a]pyridine-3-carboxylic acid: To ethyl 7-(2-methoxyethoxy)imidazo[1,2-a]pyridine-3-carboxylate (5.01 g, 19.0 mmol) in THF/EtOH (32/6 mL) was added lithium hydroxide (37.9 ml, 37.9 mmol), and the reaction was stirred overnight. HCl (57 mmol, 2M in ether) was added to the mixture, followed by concentration to give the desired product.

Step 2C: Preparation of N-methoxy-7-(2-methoxyethoxy)-N-methylimidazo[1,2-a]pyridine-3-carboxamide: To EDCI (2.196 g, 11.45 mmol) and HOBT-$H_2O$ (1.754 g, 11.45 mmol) in DMF (50 mL) was added N-ethyl-N-isopropylpropan-2-amine (1.4.80 g, 11.45 mmol), followed by the addition of N,O-dimethylhydroxylamine hydrochloride (1.117 g, 11.45 mmol). The reaction was stirred overnight, followed by concentration to remove most of the DMF. The crude mixture was diluted with saturated $NaHCO_3$ (20 mL)/EtOAc (40 mL). The aqueous phase was ten extracted with EtOAc, dried over $Na_2SO_4$ and concentrate to give the desired product (72%).

3. Preparation of 5-(8-((trans)-3-fluoropiperidin-4-yloxy)-2-(7-(2-methoxyethoxy)imidazo[1,2-a]pyridin-3-yl)quinolin-4-yl)oxazole Step 3A: Preparation of tert-butyl 2-methoxy-6-(3-(7-(2-methoxyethoxy)imidazo[1,2-a]pyridin-3-yl)-3-oxoprop-1-ynyl)phenylcarbamate: To tert-butyl 2-ethynyl-6-methoxyphenylcarbamate (1.77 g, 7.18 mmol) in THF (40 mL) was added butyllithium (0.919 g, 14.4 mmol) at −78° C., and the reaction was stirred for 1 hour. N-methoxy-7-(2-methoxyethoxy)-N-methylimidazo[1,2-a]pyridine-3-carboxamide (1.67 g, 5.98 mmol) in THF (55 mL) was then added to the reaction mixture dropwise. After the addition, the cold bath was removed and the reaction was warmed to ambient temperature. Following a 2 hour stir at ambient temperature, the reaction mixture was poured into cold saturated $NH_4Cl$ (40 mL) and EtOAc (50 mL). The phases were separated and the aqueous phase was extracted with EtOAc, dried over $Na_2SO_4$, filtered and concentrated. The residue was triturated with DCM to give product as a solid. The DCM solution was concentrated and purified by flash column chromatography (EtOAc/MeOH 10:0 to 10:1) to provide the desired product.

Step 3B: Preparation of 4-iodo-8-methoxy-2-(7-(2-methoxyethoxy)imidazo[1,2-a]pyridin-3-yl)quinoline: To tert-butyl 2-methoxy-6-(3-(7-(2-methoxyethoxy)imidazo[1,2-a]pyridin-3-yl)-3-oxoprop-1-ynyl)phenylcarbamate (2.51 g, 5.39 mmol) and sodium iodide (16.2 g, 108 mmol) was added acetic acid/formic acid (5 mL/5 mL). The reaction vessel was purged with $N_2$ and heated to 60° C. for 3 hours. The reaction was then cooled to ambient temperature and diluted with $H_2O$/DCM (50 mL/100 mL), followed by extraction with DCM. The combined organics were washed with saturated $NaHCO_3$, dried over $Na_2SO_4$, filtered and concentrated in vacuo. The residue was purified by flash column chromatography (EtOAc/MeOH 10:1) provided the desired product (92%).

Step 3C: Preparation of 8-methoxy-2-(7-(2-methoxyethoxy)imidazo[1,2-a]pyridin-3-yl)-4-vinylquinoline: To 4-iodo-8-methoxy-2-(7-(2-methoxyethoxy)imidazo[1,2-a]pyridin-3-yl)quinoline (898 mg, 1.89 mmol) in NMP (10 mL) was added Pd2dba3 (87 mg, 0.09 mmol), trifuran-2-ylphosphine (88 mg, 0.37 mmol) and tributyl(vinyl)stannane (659 mg, 2.1 mmol). The reaction flask was purged with $N_2$ and the reaction was stirred at 80° C. for 2 hours. The crude mixture was diluted with EtOAc (30 mL) then washed with $H_2O$, dried over $Na_2SO_4$ and concentrated. The residue was purified by flash column chromatography (EtOAc/Hexane 8:1) affording the desired product (80%).

Step 3D: Preparation of 1-(8-methoxy-2-(7-(2-methoxyethoxy)imidazo[1,2-a]pyridin-3-yl)quinolin-4-yl)ethane-1,2-diol: To 8-methoxy-2-(7-(2-methoxyethoxy)imidazo[1,2-a]pyridin-3-yl)-4-vinylquinoline (656 mg, 1.75 mmol) in DCM (20 mL) at 0° C. was added dropwise a solution of triethylbenzylammonium chloride (504 mg, 2.62 mmol) and $kMnO_4$ (414 mg, 2.62 mmol) in DCM (40 mL), and the reaction was stirred for 2 hours at 0° C. The reaction mixture was then warmed to ambient temperature and treated with 3% NaOH (30 mL). The mixture was filtered through celite and washed with DCM (100 mL), followed by extraction with DCM. The combined organic phases were dried over $Na_2SO_4$, filtered and concentrated to give the desired product (44%).

Step 3E: Preparation of 8-methoxy-2-((7-(2-methoxyethoxy)imidazo[1,2-a]pyridin-3-yl)quinoline-4-carbaldehyde: To silica gel (1.5 g) in DCM (5 mL) was added dropwise sodium periodate (131 μl, 0.850 mmol), affording a slurry after the addition. 1-(8-Methoxy-2-(7-(2-methoxyethoxy)imidazo[1,2-a]pyridin-3-yl)quinolin-4-yl)ethane-1,2-diol (232 mg, 0.567 mmol) in DCM (3 mL) was added to the slurry, followed by 30 minute stir. The mixture was then filtered, washed with DCM (10 mL), and concentrated to give the desired product (100%).

Step 3F: Preparation of 5-(8-methoxy-2-(7-(2-methoxyethoxy)imidazo[1,2-a]pyridin-3-yl)quinolin-4-yl)oxazole: To 8-Methoxy-2-(7-(2-methoxyethoxy)imidazo[1,2-a]pyridin-3-yl)quinoline-4-carbaldehyde (210 mg, 0.556 mmol) and 1-(isocyanomethylsulfonyl)-4-methylbenzene (130 mg, 0.668 mmol) in MeOH (5 mL) was added $K_2CO_3$ (154 mg, 1.11 mmol), followed by heating to reflux for 3 hours. The reaction was then cooled to ambient temperature, concentrated and purified by flash column chromatography (EtOAc/MeOH 10:1) providing the desired product (73%). MS APCI (+) m/z 417.2 (M+1) detected.

Step 3G: Preparation of 2-(7-(2-methoxyethoxy)imidazo[1.2-a]pyridin-3-yl)-4-(oxazol-5-yl)quinolin-8-ol: To 5-(8-methoxy-2-(7-(2-methoxyethoxy)imidazo[1,2-a]pyridin-3-yl)quinolin-4-yl)oxazole (80 mg, 0.19 mmol) in DMF (3 mL) was added sodium ethanethiolate (162 mg, 1.9 mmol). The reaction vial was sealed and heated to 150° C. for 2 hours. The reaction was then cooled to ambient temperature and concentrated. The residue was purified by flash column chromatography (DCM/MeOH 10:1) providing the desired product (39%).

Step 3H: Preparation of (trans)tert-butyl 3-fluoro-4-(2-(7-(2-methoxyethoxy)imidazo[1,2-a]pyridin-3-yl)-4-oxazol-5-yl)quinolin-8-yloxy)piperidine-1-carboxylate: To 2-(7-(2-methoxyethoxy)imidazo[1,2-a]pyridin-3-yl)-4-(oxazol-5-yl)quinolin-8-ol (9 mg, 0.02 mmol) in DMA (2 mL) was added (cis)-tert-butyl 3-fluoro-4-(methylsulfonyloxy)piperidine-1-carboxylate (13 mg, 0.04 mmol) and Cs₂CO₃ (22 mg, 0.07 mmol). The reaction vial was sealed and heated to 106° C. for 4 hours. The reaction was cooled to ambient temperature and concentrated. The crude residue was purified by flash column chromatography (DCM/MeOH 10:1) providing the desired product (3%).

Step 3I: Preparation of 5-(8-((trans)-3-fluoropiperidin-4-yloxy)-2-(7-(2-methoxyethoxy)imidazo[1,2-a]pyridin-3-yl)quinolin-4-yl)oxazole: To (trans)-tert-butyl 3-fluoro-4-(2-(7-(2-methoxyethoxy)imidazo[1,2-a]pyridin-3-yl)-4-(oxazol-5-yl)quinolin-8-yloxy)piperidine-1-carboxylate (4 mg, 0.007 mmol) in DCM (1 mL) was added TFA (1 mL), followed by a 30 minute stir. The crude reaction was concentrated and purified by flash column chromatography (DCM/MeOH/NH₄OH 10:1:0.1) affording the desired product (60%). MS APCI (+) m/z 504.2 (M+1) detected.

Example 26

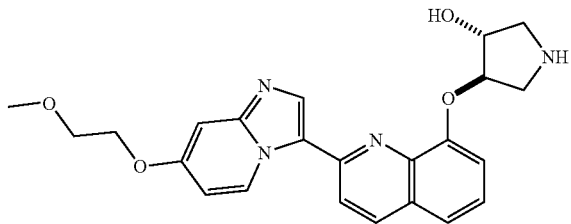

(trans)-4-(2-(7-(2-methoxyethoxy)imidazo[1,2-a]pyridin-3-yl)quinolin-8-yloxy)pyrrolidin-3-ol 1. Preparation of naphthalen-2-ylmethyl 6-oxa-3-azabicyclo[3.1.0]hexane-3-carboxylate Step 1A: Preparation of naphthalen-2-ylmethyl 2,5-dihydro-1H-pyrrole-1-carboxylate: Naphthalen-2-ylmethyl carbonochloridate (31.93 g, 144.7 mmol) was added to a solution of 2,5-dihydro-1H-pyrrole (10 g, 144.7 mmol) in a 1:1 mixture of saturated NaHCO₃ (400 mL) and THF (400 mL). The reaction was stirred for 12 hours, condensed to a small volume, diluted with saturated NaHCO₃, extracted with CH₂Cl₂, wash with 1 N HCl, dried over sodium sulfate, filtered and condensed to afford 27.5 g of the desired product as a solid.

Step 1B: Preparation of naphthalen-2-ylmethyl 6-oxa-3-azabicyclo[3.1.0]hexane-3-carboxylate: mCPBA (4.203 g, 17.04 mmol) was added to a solution of naphthalen-2-ylmethyl 2,5-dihydro-1H-pyrrole-1-carboxylate (2.15 g, 8.52 mmol) in chloroform (35 mL), and the reaction was stirred for 4 days. The reaction mixture was diluted with saturated NaHCO₃ and chloroform, and the organic layer was washed with CHCl₃, dried over sodium sulfate and condensed. The residue was purified by silica gel chromatography, eluting with a gradient from 1% EtOAc/DCM to 15% EtOAc/DCM, to provide the desired product as a solid (1.0 g).

2. Preparation of 2-(7-(2-methoxyethoxy)imidazo[1,2-a]pyridin-3-yl)quinolin-8-ol Step 2A: Preparation of 8-(benzyloxy)quinolin-2-ol: To a flask was added quinoline-2,8-diol (20.0 g, 124.1 mmol), K₂CO₃ (17.15 g, 124.1 mmol), benzyl bromide (14.76 ml, 124.1 mmol) and DMF (124.1 ml, 124.1 mmol). The resulting mixture was heated to 65° C. overnight. The reaction mixture was poured into 1000 ml water and stirred for 5 hours, filtered solids and then washed with 1000 ml diethyl ether to yield 26.5 g (85% yield) of desired product.

Step 2B: Preparation 8-(benzyloxy)-2-chloroquinoline: A flask was charged with 8-(benzyloxy)quinolin-2-ol (26.5 g, 105 mmol) and DCE (105 ml, 105 mmol). Oxalyl chloride (18.4 ml, 211 mmol) was added dropwise, and then a couple of drops of DMF (0.5 ml, 105 mmol) were added. The reaction was heated to 85° C. overnight, then cooled to ambient temperature and concentrated to an oil. DCM (300 mL) was added to the oil, and the organic layer was washed with 300 ml of saturated NaHCO₃. The layers were separated and the organic phase was dried over Na₂SO₄, filtered and concentrated to an oil. The oil was crystallized from toluene to yield 28.4 g of desired product (quantitative yield).

Step 2C: Preparation of 8-(benzyloxy)-2-(7-(2-methoxyethoxy)-imidazo[1,2-a]pyridin-3-yl)quinoline: 8-(Benzyloxy)-2-chloroquinoline (5.0 g, 18.5 mmol), 7-(2-methoxyethoxy)imidazo[1,2-a]pyridine (3.56 g, 18.5 mmol), Pd(PPh₃)₄ (1.07 g, 0.927 mmol), K₂CO₃ (5.12 g, 37.1 mmol), and Pd(OAc)₂ (0.208 g, 0.927 mmol) were added into dioxane (74.1 ml, 18.5 mmol) and water (0.735 ml, 40.8 mmol) and heated to 100° C. overnight under nitrogen. The reaction was diluted with DCM and carbon (5 g) was added, followed by filtration. The filtrate was concentrated and then triturated with 1:1 EtOAc/MTBE (30 mL). The resulting solids were allowed to stir for 5 hours and then filtered to isolate of the desired product as a solid (5.4 g, 69% yield).

Step 2D: Preparation of 2-(7-(2-methoxyethoxy)imidazo[1,2-a]pyridin-3-yl)quinolin-8-ol: 8-(Benzyloxy)-2-(7-(2-methoxyethoxy)-imidazo[1,2-a]pyridin-3-yl)quinoline (5.00 g, 11.8 mmol) was slurried in MeOH (118 ml). Ammonium formate (7.41 g, 117 mmol) and Pd(OH)₂/C (0.82 g, 0.59 mmol) were added, and the reaction was heated at reflux for 2 hours. The reaction mixture was cooled to 20° C. and formic acid was added to the slurry until solids went into solution. The resulting mixture was filtered and washed with 100 ml 10% formic acid in methanol. The filtrate was concentrated to an oil. To the oil was added an excess of NH3 in methanol and resulting the solids were concentrated to dryness. Water was added and solids were allowed to stir for 1 hour (pH was 6.5-7.0 by pH paper). The solids were collected by filtration and then taken up in toluene and concentrated to dryness. The solids were dried under vacuum for 12 hours to obtain 3.8 g (96% yield) of the desired product.

3. Preparation of (trans)-4-(2-(7-(2-methoxyethoxy)imidazo[1,2-a]pyridin-3-yl)quinolin-8-yloxy)pyrrolidin-3-ol Step 3A: Preparation of (trans)-naphthalen-2-ylmethyl 3-hydroxy-4-(2-(7-(2-methoxyethoxy)imidazo[1,2-a]pyridin-3-yl)quinolin-8-yloxy)pyrrolidine-1-carboxylate: Cs₂CO₃. (0.2201 g, 1.141 mmol) was added to a solution of 2-(7-(2-methoxyethoxy)imidazo[1,2-a]pyridin-3-yl)quinolin-8-ol (0.294 g, 0.878 mmol) and (cis)-naphthalen-2-ylmethyl 6-oxa-3-azabicyclo[3.1.0]hexane-3-carboxylate (0.260 g, 0.966 mmol) in DMF (4.5 mL). The reaction was heated to 100° C. overnight, then cooled and poured into 30 mL of ice water. This mixture was extracted with 25%. IPA in CH₂Cl₂, and the organic layer was dried over sodium sulfate and condensed. The residue was purified by silica gel chromatography, eluting with gradient from 1% to 25% MeOH (with 6% NH₄OH) in EtOAc, to collect 223 mg of the desired product. MS APCI (+) m/z 605.1 (M+1) detected.

Step 3B: Preparation of (trans)-4-(2-(7-(2-methoxyethoxy)imidazo[1,2-a]pyridin-3-yl)quinolin-8-yloxy)pyrrolidin-3-ol: A 25 mL flask was charged with (trans)-naphthalen-2-ylmethyl 3-hydroxy-4-(2-(7-(2-methoxyethoxy)imidazo[1,2-a]pyridin-3-yl)quinolin-8-yloxy)pyrrolidine-1-carboxylate (0.100 g, 0.165 mmol), EtOH (1.6 mL), THF (1.6 mL), 2 N HCl (0.2 mL) and 10% Degussa type Pd/C (0.018 g, 0.017 mmol), and the reaction was placed under a balloon of H₂ and stirred for 2 hours. The reaction was filtered (GF/F paper), the filter paper was washed with 2 N HCl and THF, the aqueous phase was washed with DCM, neutralized with saturated NaHCO₃, and then extracted with DCM. The organic layer was dried and condensed to afford 14 mg of the desired product. MS APCI (+) m/z 421.2 (M+1) detected.

Example 27

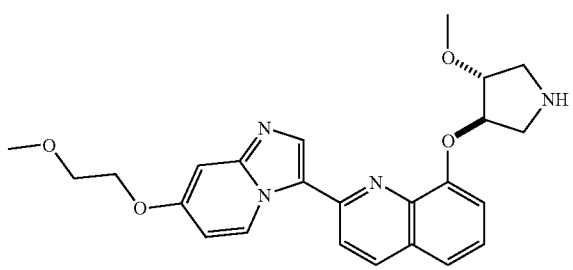

2-(7-(2-methoxyethoxy)imidazo[1,2-a]pyridin-3-yl)-
8-((trans)-4-methoxypyrrolidin-3-yloxy)quinoline Step A: Preparation of (trans)-naphthalen-2-ylmethyl 3-methoxy-4-(2-(7-(2-methoxyethoxy)imidazo[1,2-a]pyridin-3-yl)quinolin-8-yloxy)pyrrolidine-1-carboxylate.
Sodium hydride (0.017 g, 0.43 mmol) was added to a solution of (trans)-naphthalen-2-ylmethyl 3-hydroxy-4-(2-(7-(2-methoxyethoxy)imidazo[1,2-a]pyridin-3-yl)quinolin-8-yloxy)pyrrolidine-1-carboxylate (0.117 g, 0.194 mmol) in DMF (1 mL). The reaction was cooled to 0° C. and stirred for 20 minutes. Iodomethane (0.012 ml, 0.194 mmol) was added, and the ice bath was removed. The reaction was stirred for 1 hour. Water was added, and the reaction mixture was extracted with CHCl₃. The combined organic layers were washed with brine, dried and condensed. The residue was purified by silica gel chromatography to provide 54 mg of the desired product. MS APCI (+) m/z 619.1 (M+1) detected.

Step B: Preparation of 2-(7-(2-methoxyethoxy)imidazo[1,2-a]pyridin-3-yl)-8-((trans)-4-methoxypyrrolidin-3-yloxy)quinoline: A flask was charged with (trans)-naphthalen-2-ylmethyl 3-methoxy-4-(2-(7-(2-methoxyethoxy)imidazo[1,2-a]pyridin-3-yl)quinolin-8-yloxy)pyrrolidine-1-carboxylate (0.054 g, 0.087 mmol), 2 N HCl (0.1 mL), THF (1 mL), EtOH (1 mL), and 10% Degussa type Pd/C (0.0186 g, 0.0175 mmol), and the reaction mixture was placed under a balloon of H₂ and stirred for 3 hours. The reaction was neutralized with saturated NaHCO₃ and filtered (GF/F paper). The filter cake was washed with CHCl₃ and water. The layers were separated, the aqueous phase was washed with chloroform, and the organic phase was dried over Na₂SO₄, filtered and condensed. The residue was purified by silica gel chromatography to provide 24 mg of the desired product. MS APCI (+) m/z 435.2 (M+1) detected.

Example 28

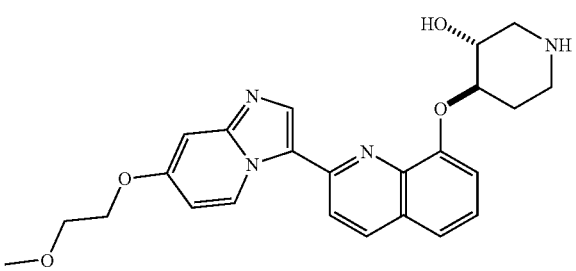

(trans)-4-(2-(7-(2-methoxyethoxy)imidazo[1,2-a]pyridin-3-yl)quinolin-8-yloxy)piperidin-3-ol Step A: Preparation of naphthalen-2-ylmethyl carbonochloridate: A solution of naphthalen-2-yl methanol (51.2 g, 324 mmol) dissolved in anhydrous THF (1 L) was treated with phosgene (205 mL, 20% solution in toluene, 388 mmol). The solution was stirred at ambient temperature for 45 minutes and then concentrated to afford the desired product as a solid, which was dried under vacuum and used directly in the next step.

Step B: Preparation of naphthalen-2-ylmethyl 5,6-dihydropyridine-1(2H)-carboxylate: Naphthalen-2-ylmethyl carbonochloridate (11.00 g, 49.85 mmol) was dissolved in THF (25 mL) and this was added dropwise to a cooled (0° C.) solution of 1,2,3,6-tetrahydropyridine (3.79 ml, 41.5 mmol) and NaHCO₃ (4.18 g, 49.8 mmol) in water (88 mL). A precipitate formed in the reaction immediately, therefore after the addition, additional THF (63 mL) was added to solubilize the reaction mixture. The solution was removed from the bath and warmed to ambient temperature for 16 hours. The reaction was concentrated in vacuo then methylene chloride was added. The mixture was separated, the aqueous layer was washed with methylene chloride, and the combined organics were dried over Na₂SO₄ and concentrated in vacuo to provide the desired product as an oil (11 g).

Step C: Preparation of naphthalen-2-ylmethyl 7-oxa-3-azabicyclo[4.1.0]heptane-3-carboxylate: A suspension of mCPBA (13.02 g, 58.13 mmol) dissolved in methylene chloride (50 mL) was added dropwise to a cooled (0° C.) solution of naphthalen-2-ylmethyl 5,6-dihydropyridine-1(2H)-carboxylate (11 g, 41.5 mmol) dissolved in methylene chloride (33 mL). The solution was allowed to warm to ambient temperature and stirred overnight. The reaction was quenched with 5% K₂CO₃ and then the layers were separated. The organic phase was washed with 5% K₂CO₃, saturated NaCl, dried over Na₂SO₄ and concentrated in vacuo (9.5 g).

Step D: Preparation of (trans)-naphthalen-2-ylmethyl 3-hydroxy-4-(2-(7-(2-methoxyethoxy)imidazo[1,2-a]pyridin-3-yl)quinolin-8-yloxy)piperidine-1-carboxylate: 2-(7-(2-Methoxyethoxy)imidazo[1,2-a]pyridin-3-yl)quinolin-8-ol (0.10 g, 0.309 mmol) was slurried in DMA (1.0 mL) and treated with Cs₂CO₃ (0.201 g, 0.618 mmol). After 10 minutes, naphthalen-2-ylmethyl 7-oxa-3-azabicyclo[4.1.0]heptane-3-carboxylate (0.100 g, 0.355 mmol) was added. The reaction was warmed to 90° C. and stirred for 40 hours. The reaction mixture was cooled to ambient temperature then added dropwise into saturated NH₄Cl (5 mL). Chloroform (25 mL) was added and the layers were separated. The aqueous layer was washed with CHCl₃ and the combined organic layers were dried over Na₂SO₄, filtered and concentrated in vacuo. The residue was purified by silica gel chromatography, eluting with a gradient from 1 to 20% (6% NH₄OH in MeOH)/ethyl acetate to provide the desired product (111 mg). MS ESI (+) m/z 619.2 (M+1) detected.

Step E: Preparation of (trans)-4-(2-(7-(2-methoxyethoxy)imidazo[1.2-a]pyridin-3-yl)quinolin-8-yloxy)piperidin-3-ol: (trans)-Naphthalen-2-ylmethyl 3-hydroxy-4-(2-(7-(2-methoxyethoxy)imidazo[1,2-a]pyridin-3-yl)quinolin-8-yloxy)piperidine-1-carboxylate (0.045 g, 0.072 mmol) was dissolved in 95% EtOH/ethyl acetate (1:1, 2 mL) and treated with 10% Pd/C (Degeussa type, 20 mg). The reaction was purged with argon then subjected to hydrogen atmosphere at balloon pressure. After 19 hours, the reaction was purged with N₂ and treated with fresh catalyst (ca. 5 mg) and re-subjected to hydrogen atmosphere for 5 hours. The reaction was filtered through a nylon membrane (0.45 uM) and concentrated in vacuo. The residue was purified by silica gel chromatography, eluting with a gradient from 1-20% (6% NH$_4$OH in MeOH)/ ethyl acetate. A solid was recovered after concentration in vacuo. The solid was dissolved in MeOH (2 mL) and treated with 4 M HCl in dioxane (0.5 mL). After stirring for 10 minutes the solution was concentrated in vacuo, then re-dissolved in MeOH and re-concentrated three times. The material was dissolved in MeOH (1 mL) then added dropwise to Et$_2$O (40 mL). A precipitate formed, and after stirring for 20 minutes, this precipitate was collected by filtration, washed with Et$_2$O and dried under a blanket of nitrogen (15 mg). $^1$H NMR (400 MHz, CD$_3$OD) δ 10.72 (d, 1H), 8.75 (s, 1H), 8.45 (d, 1H), 8.11 (D, 1H), 7.65-7.59 (m, 2H), 7.49-7.43 (m, 1H), 7.43-7.38 (m, 2H), 4.94-4.87 (m, 1H), 4.48-4.43 (m, 2H), 4.37-4.32 (m, 1H), 3.89-3.84 (m, 2H), 3.64-3.57 (m, 1H), 3.49-3.40 (m, 1H), 3.46 (s, 3H), 3.37-3.31 (m, 1H), 2.58-2.48 (m, 1H), 2.27-2.18 (m, 1H). MS APCI (+) m/z 435.1 (M+1) detected.

Example 29

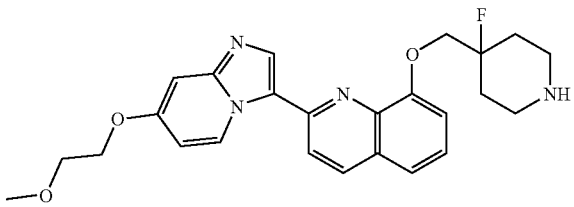

8-((4-fluoropiperidin-4-yl)methoxy)-2-(7-(2-methoxyethoxy)imidazo[1.2-a]pyridin-3-yl)quinoline Step A: Preparation of tert-butyl 4-fluoro-4-(hydroxymethyl)piperidine-1-carboxylate: 4-Fluoro-1-(1,1-dimethylethyl)1,4-piperidinedicarboxylic acid-4-ethyl ester (0.40 g, 1.45 mmol) was dissolved in THF (1.5 mL), cooled to 0° C. and treated with lithium aluminum hydride (1 M in THF, 2.90 ml, 2.90 mmol). The reaction mixture was stirred at 0° C. for 2 hours, then warmed to ambient temperature for 3 hours. The reaction was quenched with sequential additions of water (110 μL), 15% NaOH (110 μL), and water (330 μL), and then stirred for 20 minutes. The slurry was diluted with ethyl acetate and filtered. The filtrate was concentrated in vacuo to provide the desired product (0.303 g).

Step B: Preparation of tert-butyl 4-fluoro-4-((methylsulfonyloxy)methyl)piperidine-1-carboxylate: tert-Butyl 4-fluoro-4-(hydroxymethyl)piperidine-1-carboxylate (0.150 g, 0.643 mmol) was dissolved in dichloromethane (1.8 mL) and cooled to 0° C. The solution was treated with triethylamine (0.134 ml, 0.964 mmol) followed by methanesulfonyl chloride (0.0547 ml, 0.707 mmol). The reaction was stirred at 0° C. for 2 hours then diluted with methylene chloride and quenched with saturated NH$_4$Cl and separated. The organic layer was washed with saturated NH$_4$Cl, 6% NaHCO$_3$, dried over Na$_2$SO$_4$, filtered and concentrated in vacuo to provide the desired product (200 mg).

Step C: Preparation of tert-butyl 4-fluoro-4-((2-(7-(2-methoxyethoxy)imidazo[1,2-a]pyridin-3-yl)quinolin-8-yloxy)methyl)piperidine-1-carboxylate: 2-(7-(2-Methoxyethoxy)imidazo[1,2-a]pyridin-3-yl)quinolin-8-ol (0.050 g, 0.149 mmol) was dissolved in DMA (0.5 mL) and treated with Cs$_2$CO$_3$ (0.097 g, 0.29 mmol). After stirring for several minutes, tert-butyl 4-fluoro-4-((methylsulfonyloxy)methyl)piperidine-1-carboxylate (0.053 g, 0.171 mmol) was added. The mixture was heated to 90° C. for 40 hours. The entire reaction mixture was applied to a SiO$_2$ column and eluted with a gradient from 1-20% (6% NH$_4$OH in MeOH)/ethyl acetate to provide the desired product (11 mg). MS ESI (+) m/z 551.1 (M+1) detected.

Step D: Preparation of 8-((4-fluoropiperidin-4-yl)methoxy)-2-(7-(2-methoxyethoxy)imidazo[1,2-a]pyridin-3-yl)quinoline: tert-Butyl 4-fluoro-4-((2-(7-(2-methoxyethoxy)imidazo[1,2-a]pyridin-3-yl)quinolin-8-yloxy)methyl)piperidine-1-carboxylate (0.011 g, 0.020 mmol) was dissolved in dioxane (0.5 mL) and treated with 4 M hydrogen chloride in dioxane (0.126 ml, 0.504 mmol). The reaction was stirred at ambient temperature for 24 hours. The mixture was concentrated in vacuo, redissolved and re-concentrated from MeOH three times. The crude material was loaded onto a SiO$_2$ column and eluted with a gradient from 1 to 20% (6% NH$_4$OH in MeOH)/ethyl acetate to provide the desired product (3 mg). $^1$H NMR (400 MHz, CDCl$_3$) δ 10.67 (d, 1H), 8.22 (s, 1H), 8.08 (d, 1H), 7.83 (s, 1H), 7.41-7.33 (m, 2H), 7/09-6.98 (m, 2H), 6.90-6.84 (m, 1H), 4.29-4.16 (m, 3H), 3.87-3.79 (m, 2H), 3.49 (s, 3H), 3.23-3.10 (m, 3H), 2.29-2.15 (m, 1H), 2.14-1.94 (m, 2H), 0.93-0.81 (m, 1H). MS APCI (+) m/z 451.2 (M+1) detected.

Example 30

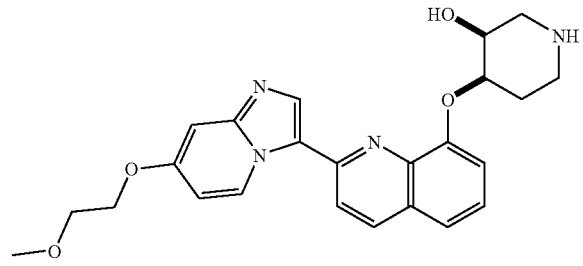

(cis)-4-(2-(7-(2-methoxyethoxy)imidazo[1,2-a]pyridin-3-yl)quinolin-8-yloxy)piperidin-3-ol Step A: Preparation of (cis)-naphthalen-2-ylmethyl 3-(benzoyloxy)-4-(2-(7-(2-methoxyethoxy)imidazo[1,2-a]pyridin-3-yl)quinolin-8-yloxy)piperidine-1-carboxylate: (trans)-Naphthalen-2-ylmethyl 3-hydroxy-4-(2-(7-(2-methoxyethoxy)imidazo[1,2-a]pyridin-3-yl)quinolin-8-yloxy)piperidine-1-carboxylate (Example 28, Steps A-D; 0.075 g, 0.121 mmol) was dissolved in THF (0.50 mL) and treated with benzoic acid (0.022 g, 0.181 mmol), PPh$_3$ (0.036 g, 0.139 mmol) and diisopropylazodicarboxylate (0.026 ml, 0.133 mmol). The mixture was stirred at ambient temperature for 40 hours, and then the whole reaction mixture was applied to a column of SiO$_2$ and eluted with a gradient from 1-20% (6% NH$_4$OH in MeOH)/ethyl acetate (75 mg). MS ESI (+) m/z 723.2 (M+1) detected.

Step B: Preparation of (cis)-naphthalen-2-ylmethyl 3-hydroxy-4-(2-(7-(2-methoxyethoxy)imidazo[1,2-a]pyridin-3-yl)quinolin-8-yloxy)piperidine-1-carboxylate: (cis)-Naphthalen-2-ylmethyl-3-(benzoyloxy)-4-(2-(7-(2-methoxyethoxy)imidazo[1,2a]pyridin-3-yl)quinolin-8-yloxy)piperidine-1-carboxylate (0.075 g, 0.103 mmol) was dissolved in THF/MeOH/water (2:2:1, 0.5 mL) and cooled to 0° C. The solution was treated with LiOH—H$_2$O (0.008 g, 0.2 mmol) and stirred at ambient temperature for 5 days. The reaction was quenched with saturated NH₄Cl and concentrated in vacuo. The residue was diluted with CHCl₃ and separated. The aqueous layer (pH ca. 8) was extracted 3 additional times with CHCl₁₃. The combined organic layers were dried over Na₂SO₄, filtered and concentrated in vacuo. The material was purified by silica gel chromatography, eluting with a gradient from 1-20% (6% NH₄OH in MeOH)/ethyl acetate to provide the desired product (31.2 mg). MS ESI (+) m/z 619.1 (M+1) detected.

Step C: Preparation of (cis)-4-(2-(7-(2-methoxyethoxy)imidazo[1,2-a]pyridin-3-yl)quinolin-8-yloxy)piperidin-3-ol: (cis)-Naphthalen-2-ylmethyl-3-hydroxy-4-(2-(7-(2-methoxyethoxy)imidazo[1,2-a]pyridin-3-yl)quinolin-8-yloxy)piperidine-1-carboxylate (0.030 g, 0.048 mmol) was dissolved in EtOH (1 mL), treated with 10% palladium on carbon (Degussa type, 50 mg), placed under a hydrogen atmosphere (balloon pressure) and stirred for 3 days. The reaction was filtered through a nylon membrane and concentrated in vacuo. The mixture was purified by preparative TLC (10 cm×20 cm×0.5 mm) eluting with 20% (6% NH₄OH in MeOH)/ethyl acetate. The recovered product was dissolved in MeOH and treated with 4 M HCl in dioxane then concentrated in vacuo. The residue was re-dissolved in MeOH and re-concentrated three times. The residue was slurried in MeOH (0.3 mL) and added dropwise to Et₂O (20 mL). The resultant solid was filtered and dried under N₂ to provide the desired product (3 mg). MS ESI (+) m/z 435.1 (M+1) detected.

Example 31

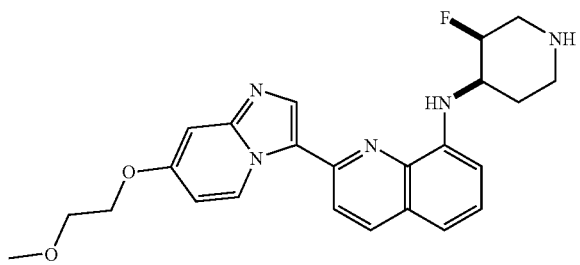

N-((cis)-3-fluoropiperidin-4-yl)-2-(7-(2-methoxyethoxy)imidazo[1,2-a]pyridin-3-yl)quinolin-8-amine 1. Preparation of 2-(7-(2-methoxyethoxy)imidazo[1.2-a]pyridin-3-yl)quinolin-8-yl trifluoromethanesulfonate Step 1A: Preparation of 8-(benzyloxy)quinolin-2-ol: A flask was charged with quinoline-2,8-diol (20.0 g, 124.1 mmol), K₂CO₃ (17.15 g, 124.1 mmol), benzyl bromide (14.76 ml, 124.1 mmol) and DMF (124.1 ml, 124.1 mmol). The resulting mixture was heated to 65° C. overnight, then poured into 1000 ml water and stirred for 5 hours. The solids were filtered and washed with 1000 ml diethyl ether to yield 26.5 g (85% yield) of desired product.

Step 1B: Preparation 8-(benzyloxy)-2-chloroquinoline: A flask was charged with 8-(benzyloxy)quinolin-2-ol (26.5 g, 105 mmol) and DCE (105 ml, 105 mmol). Oxalyl chloride (18.4 ml, 211 mmol) was added dropwise, followed by a few drops of DMF (0.5 ml, 105 mmol), and the reaction mixture was heated to 85° C. overnight. The reaction was cooled to ambient temperature and concentrated to an oil. DCM (300 mL) was added to the oil and the organic layer was washed with 300 ml of saturated NaHCO₃. The layers were separated and the organic phase was dried over Na₂SO₄, filtered and concentrated to an oil. The oil was crystallized from toluene to yield 28.4 g of desired product (quantitative yield).

Step 1C: Preparation of 8-(benzyloxy)-2-(7-(2-methoxyethoxy)-imidazo[1,2-a]pyridin-3-yl)quinoline: 8-(Benzyloxy)-2-chloroquinoline (5.0 g, 18.5 mmol), 7-(2-methoxyethoxy)-imidazo[1,2-a]pyridine (3.56 g, 18.5 mmol), Pd(PPh₃)₄ (1.07 g, 0.927 mmol), K₂CO₃ (5.12 g, 37.1 mmol), and Pd(OAc)₂ (0.208 g, 0.927 mmol) were added to dioxane (74.1 ml, 18.5 mmol) and water (0.735 ml, 40.8 mmol) and the reaction mixture was heated to 100° C. overnight under nitrogen. The reaction was diluted with DCM and 5 g of carbon were added followed by filtration. The slurry was concentrated and the filtrate was triturated with 1:1 EtOAc/MTBE (30 mL). The resulting solids were stirred for 5 hours and then filtered to isolate the desired product as a solid (5.4 g, 69% yield).

Step 1D: Preparation of 2-(7-(2-methoxyethoxy)imidazo[1,2-a]pyridin-3-yl)quinolin-8-ol: 8-(Benzyloxy)-2-(7-(2-methoxyethoxy)-imidazo[1,2-a]pyridin-3-yl)quinoline (5.0 g, 11.75 mmol) was slurried in MeOH (117.5 ml). Ammonium formate (7.410 g, 117.5 mmol) and Pd(OH)₂/C (0.8252 g, 0.5876 mmol) were added. The reaction mixture was heated to reflux for 2 hours, then cooled to 20° C. Formic acid was added to the slurry until solids went into solution. The mixture was filtered and the filter paper was washed with 10% formic acid in methanol. The filtrate was concentrated to an oil. To the oil was added an excess of NH₃ in methanol and resulting the solids were concentrated to dryness. Water was added to the solids and the slurry was stirred for 1 hour (pH was 6.5-7.0 by pH paper). The solids were collected by filtration and then taken up in toluene and concentrated to dryness under vacuum dry for 12 hours to obtain 3.8 g (96% yield) of the desired product.

2. Preparation of N-((cis)-3-fluoropiperidin-4-yl)-2-(7-(2-methoxyethoxy)imidazo[1,2-a]pyridin-3-yl)quinolin-8-amine Step 2A: Preparation of tert-butyl 3-fluoro-4-hydroxypiperidine-1-carboxylate: tert-Butyl 3-fluoro-4-oxopiperidine-1-carboxylate [van Niel, M. B.; et al.; J. Med: Chem. 1999, 42, 2087-2104] (52.27 g, 241 mmol) was dissolved in anhydrous MeOH (600 mL), cooled to 0° C. and treated in portions with sodium borohydride (37.8 g, 361 mmol) over a 15 minute period. After stirring at 0° C. for 30 minutes, the mixture was stirred at ambient temperature for 4 hours. The mixture was concentrated under reduced pressure and the residue was partitioned between saturated ammonium chloride solution (400 mL) and EtOAc (400 mL). The aqueous layer was extracted with EtOAc and the combined organic extracts were washed with brine (200 mL), dried over Na₂SO₄, filtered and concentrated to provide the desired product as a thick oil that slowly solidified upon standing (52.7 g).

Step 2B: Preparation of (trans)-tert-butyl 3-fluoro-4-(methylsulfonyloxy)piperidine-1-carboxylate: A solution of tert-butyl 3-fluoro-4-hydroxypiperidine-1-carboxylate (52.76 g, 241 mmol) dissolved in anhydrous methylene chloride (1 L) was cooled to 0° C. and treated with triethylamine (43.6 mL, 313 mmol) followed by methanesulfonyl chloride (20.5 mL, 265 mmol). The solution was allowed to warm slowly to ambient temperature and stirred for 14 hours. The mixture was partitioned between saturated NaHCO₃ (400 mL) and methylene chloride (400 mL). The aqueous layer was extracted with methylene chloride. The combined organic phases were washed with 1N HCl and brine, dried over Na₂SO₄, filtered and concentrated in vacuo. The residue was purified by silica gel chromatography, eluting with hexanes:EtOAc to provide the desired product (7.24 g).

Step 2C: Preparation of (cis)-tert-butyl 4-azido-3-fluoropiperidine-1-carboxylate: Sodium azide (4.045 g, 62.22 mmol) was added to a solution of (trans)-tert-butyl 3-fluoro-4-(methylsulfonyloxy)piperidine-1-carboxylate (3.700 g, 12.44 mmol) dissolved in DMF (25 mL). The reaction was heated to 115° C. for 24 hours. The mixture was cooled and diluted with water and methylene chloride. After separation, the organic layer was dried over Na₂SO, filtered and concentrated in vacuo to provide the desired product (quantitative yield).

Step 2D: Preparation of (cis)-tert-butyl 4-amino-3-fluoropiperidine-1-carboxylate: Palladium on carbon (10%, 0.876 g, 0.823 mmol) was added to a solution of (cis)-tert-butyl 4-azido-3-fluoropiperidine-1-carboxylate (2.01 g, 8.23 mmol) dissolved in THF and EtOH (1:1, 82 mL). The reaction was placed under a hydrogen atmosphere (balloon pressure) and stirred for 2 hours. The mixture was filtered through GF/F paper and concentrated in vacuo. The amine was purified on a Varian Bond Elut SCX column, eluting with methylene chloride followed by a solution of MeOH containing 6% aqueous NH₄OH. The second eluant was concentrated in vacuo to provide the desired product (642 mg). MS ESI (+) m/z 218.8 (M+1) detected.

Step 2E: Preparation of (cis)-tert-butyl 3-fluoro-4-(2-(7-(2-methoxyethoxy)imidazo[1,2-a]pyridin-3-yl)quinolin-8-ylamino)piperidine-1-carboxylate: (cis)-tert-Butyl 4-amino-3-fluoropiperidine-1-carboxylate (0.040 g, 0.18 mmol) was combined with 2-(7-(2-methoxyethoxy)imidazo[1,2-a]pyridin-3-yl)quinolin-8-yl trifluoromethanesulfonate (Steps 1A-1D; 0.065 g, 0.140 mmol), micronized Cs₂CO₃ (0.064 g, 0.197 mmol), BINAP-racemic (0.0087 g, 0.014 mmol) and Pd₂dba₃ (0.0064 g, 0.0070 mmol). The mixture was treated with toluene (0.75 mL), degassed with argon and heated to reflux for 16 hours. The reaction was cooled, diluted with CHCl₃ and purified by silica gel chromatography, eluting with a gradient from 1-20% (6% NH₄OH in MeOH)/ethyl acetate to provide the desired product (82 mg). MS ESI (+) m/z 536.1 (M+1) detected.

Step 2F: Preparation of N-(cis)-3-fluoropiperidin-4-yl)-2-(7-(2-methoxyethoxy)imidazo[1,2-a]pyridin-3-yl)quinolin-8-amine: (cis)-tert-Butyl 3-fluoro-4-(2-(7-(2-methoxyethoxy)imidazo[1,2-a]pyridin-3-yl)quinolin-8-ylamino)piperidine-1-carboxylate (0.050 g, 0.093 mmol) was dissolved in MeOH (1 mL) the solution was treated with 4 M hydrogen chloride in dioxane (0.583 ml, 2.33 mmol). The mixture was stirred at ambient temperature for 4 hours, then concentrated in vacuo. The residue was redissolved and reconcentrated from MeOH three times. This material was purified by silica gel chromatography, eluting with (6% NH₄OH in MeOH)/ethyl acetate to provide the desired product (16 mg). ¹H NMR (400 MHz, CDCl₃) δ 9.89 (d, 1H), 8.14 (s, 1H), 8.05 (d, 1H), 7.77 (d, 1H), 7.38-7.29 (m, 1H), 7.08 (d, 1H), 7.02 (s, 1H), 6.85-6.74 (m, 2H), 6.30 (d, 1H), 4.89 (d, J=49 Hz, 1H), 4.26-4.19 (m, 2H), 3.87-3.78 (m, 2H), 3.79-3.69 (m, 1H), 3.54-3.42 (m, 1H), 3.48 (s, 3H), 3.27-3.18 (m, 1H), 3.04-2.87 (dd, 1H), 2.79 (t, 1H), 2.17-2.09 (m, 1H), 2.00-1.86 (brd, 1H), 1.81-1.67 (m, 1H), 1.30-1.22 (m, 1H).

Example 32

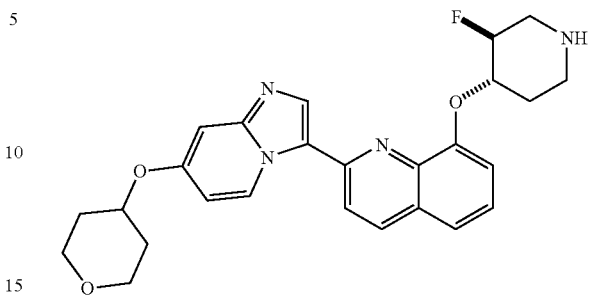

8-((trans)-3-fluoropiperidin-4-yloxy)-2-(7-(tetrahydro-2H-pyran-4-yloxy)imidazo[1,2-a]pyridin-3-yl) quinoline 1. Preparation of (trans)-benzyl 4-(2-chloroquinolin-8-yloxy)-3-fluoropiperidine-1-carboxylate Step 1A: Preparation of (trans)-tert-butyl 3-fluoro-4-(quinolin-8-yloxy)piperidine-1-carboxylate: To a solution of quinolin-8-ol (3.50 g, 24.1 mmol) in 60 mL DMF was added cesium carbonate (23.6 g, 72.3 mmol), followed by (cis)-tert-butyl 3-fluoro-4-(methylsulfonyloxy)piperidine-1-carboxylate (8.24 g, 27.7 mmol). The reaction mixture was heated in a 100° C. sand bath and stirred 20 hours. The reaction mixture was cooled to ambient temperature, filtered through GF/F paper topped with compressed Celite, rinsed with DMF, and concentrated. The crude was purified on silica gel (Biotage 40M, 9:1 DCM:EtOAc until the product eluted, then 2:1 DCM:EtOAc) to give (trans)-tert-butyl 3-fluoro-4-(quinolin-8-yloxy)piperidine-1-carboxylate (0.701 g, 2.02 mmol, 42% yield). LC/MS ESI (+) m/z 347 (M+1) detected.

Step 1B: Preparation of 8-((trans)-3-fluoropiperidin-4-yloxy)quinoline dihydrochloride: To a solution of (trans)-tert-butyl 3-fluoro-4-(quinolin-8-yloxy)piperidine-1-carboxylate (5.4 g, 15.6 mmol) in 100 mL DCM was added neat TFA (24.0 ml, 311.78 mmol). The reaction mixture was stirred at ambient temperature for 4 hours, after which it was concentrated. The resulting residue was dissolved in 40 mL DCM, and this solution was added dropwise by addition funnel to a flask containing vigorously stirring 60 mL 2 M HCl in ether in 500 mL ether, causing precipitation. The solids were isolated by filtration through a medium pore glass fritted funnel by forcing solvent through the frit with nitrogen pressure, rinsed with ether, and dried in vacuo to give 8-(trans-3-fluoropiperidin-4-yloxy)quinoline dihydrochloride (6.6 g, 21 mmol) as a solid which was used without further purification in the next step. LC/MS ESI (+) m/z 247 (M+H)⁻ detected.

Step 1C: Preparation of (trans)-benzyl 3-fluoro-4-(quinolin-8-yloxy)piperidine-1-carboxylate: To a 0° C. solution of 8-((trans)-3-fluoropiperidin-4-yloxy)quinoline dihydrochloride (6.6 g, 26.8 mmol) and TEA (18.7 ml, 134.0 mmol) in 134 mL DCM was added benzyl carbonochloridate (4.4 ml, 29.5 mmol). The reaction mixture was stirred 15 minutes at 0° C., then warmed to ambient temperature and stirred another 16 hours. Water was added, and the mixture was extracted with DCM. The combined extracts were dried (Na₂SO₄), filtered, and concentrated. The crude was purified on silica gel (Biotage 40M, loaded with 4:1 hexanes:ethyl acetate and 500 mL flushed, then gradient to 1:1 hexanes:ethyl acetate) to give (trans)-benzyl 3-fluoro-4-(quinolin-8-yloxy)piperidine-1-carboxylate (5.2 g, 13.67 mmol, 51.01% yield) as an oil. MS APCI (+) m/z 381 (M+1) detected.

Step 1D: Preparation of 8-((trans)-1-(benzyloxycarbonyl-3-fluoropiperidin-4-yloxy)quinoline 1-oxide: To a 0° C. solution of (trans)-benzyl 3-fluoro-4-(quinolin-8-yloxy)piperidine-1-carboxylate (1.0 g, 2.63 mmol) in 20 mL CHCl$_3$ and 2 mL MeOH was added 77% max. mCPBA in 4×250 mg portions. The reaction mixture was stirred 20 minutes, then another 2×250 mg portions of 77% max. mCPBA was added (total 77% max. mCPBA (1.51 g, 6.57 mmol)). The reaction mixture was stirred 10 minutes, warmed to ambient temperature, and stirred another 3 hours, after which it was cooled to 0° C. Another 2 equivalents of 77% max. mCPBA was added in 4 equal portions, and the reaction mixture was warmed to ambient temperature and stirred an additional 1.5 hours. The reaction mixture was cooled to 0° C., and saturated Na$_2$S$_2$O$_3$ was added, followed by saturated NaHCO$_3$. The mixture was stirred 10 minutes, then warmed to ambient temperature and stirred another 30 minutes. Solid NaCl was added, and the mixture was extracted with CHCl$_3$. The combined extracts were dried (Na$_2$SO$_4$), filtered, concentrated, and dried in vacuo to give 8-((trans)-1-(benzyloxycarbonyl)-3-fluoropiperidin-4-yloxy)quinoline 1-oxide (1.0 g, 2.52 mmol, 96.0% yield), which was used without further purification in the next step.

Step 1E: Preparation of (trans)-benzyl 4-f2-chloroquinolin-8-yloxy)-3-fluoropiperidine-1-carboxylate: To a 0° C. solution of 4 mL 1:1 DMF:toluene was added neat POCl$_3$ (0.360 ml, 3.94 mmol). The reaction mixture was warmed to ambient temperature, stirred 10 minutes, and then cooled to 0° C. A solution of 8-((trans)-1-(benzyloxycarbonyl)-3-fluoropiperidin-4-yloxy)quinoline 1-oxide (1.04 g, 2.62 mmol) in 1.2 mL 1:1 DMF:toluene was added dropwise by syringe to the reaction mixture, and the reaction mixture was heated in a 110° C. sand bath and stirred for 1 hours. The reaction mixture was cooled to ambient temperature and added dropwise to a stirring ice/saturated NaHCO$_3$ mixture. The mixture was stirred 20 minutes, then extracted with DCM, and the combined extracts were dried (Na$_2$SO$_4$), filtered, and concentrated. The crude was purified on silica gel (Biotage 40S, loaded with 12:1hexanes:ethyl acetate, flushed 300 mL, then gradient to 5:1 hexanes:ethyl acetate) to give (trans)-benzyl 4-(2-chloroquinolin-8-yloxy)-3-fluoropiperidine-1-carboxylate (0.563 g, 1.36 mmol, 51.7% yield) as a syrup. MS APCI (+) m/z 415 (M+1) detected.

2. Preparation of 8-((trans)-3-fluoropiperidin-4-yloxy)-2-(7-(tetrahydro-2H-pyran-4-yloxy)imidazo[1,2-a]pyridin-3-yl)quinoline dihydrochloride Step 2A: Preparation of 7-(tetrahydro-2H-pyran-4-yloxy)imidazo[1,2-a]pyridine: Prepared according to the procedure for Example 1, Steps 1A-C, using tetrahydro-2H-pyran-4-ol in place of 2-methoxyethanol. MS APCI (+) m/z 219 (M+1) detected.

Step 2B: Preparation of (trans)-benzyl 3-fluoro-4-(2-(7-(tetrahydro-2H-pyran-4-yloxy)imidazo[1,2-a]pyridin-3-yl)quinolin-8-yloxy)piperidine-1-carboxylate: Prepared according to the procedure used for Example 1, Step D, using 7-(tetrahydro-2H-pyran-4-yloxy)imidazo[1,2-a]pyridine in place of 7-(2-methoxyethoxy)imidazo[1,2-a]pyridine and (trans)-benzyl 4-(2-chloroquinolin-8-yloxy)-3-fluoropiperidine-1-carboxylate in place of 2,8-dibromoquinoline. MS APCI (+) m/z 597 (M+1) detected.

Example 33

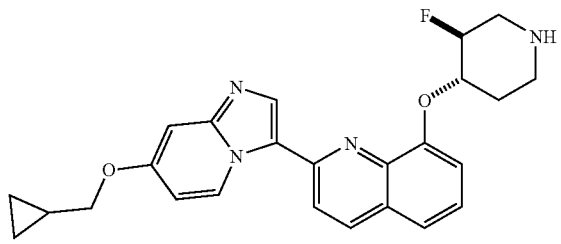

2-(7-(cyclopropylmethoxy)imidazo[1,2-a]pyridin-3-yl)-8-((trans)-3-fluoropiperidin-4-yloxy)quinoline Prepared according to the procedure of Example 32, using cyclopropylmethanol in place of tetrahydro-2H-pyran-4-ol. MS APCI (+) m/z 433 (M+1) detected.

Example 34

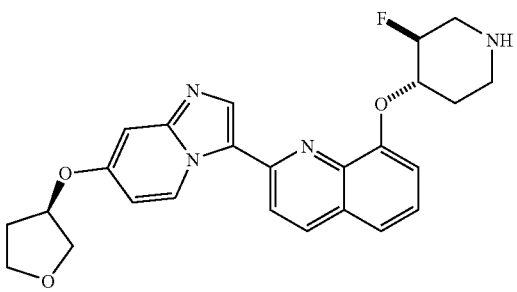

8-((trans)-3-Fluoropiperidin-4-yloxy)-2-(7-((R)-tetrahydrofuran-3-yloxy)imidazo[1,2-a]pyridin-3-yl)quinoline Prepared according to the procedure of Example 32, using (R)-tetrahydrofuran-3-ol in place of tetrahydro-2H-pyran-4-ol. The title compound was isolated as a 1:1 mixture of diastereomers. MS APCI (+) m/z 449 (M+1) detected.

Example 35

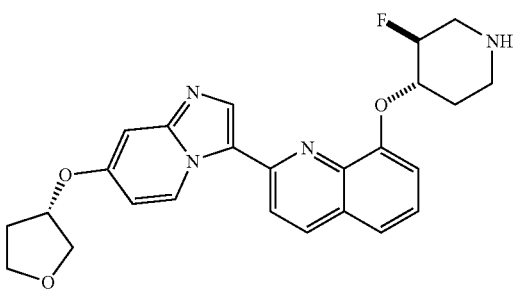

8-((trans)-3-Fluoropiperidin-4-yloxy)-2-(7-((S)-tetrahydrofuran-3-yloxy)imidazo[1,2-a]pyridin-3-yl)quinoline Prepared according to the procedure of Example 32, using (S)-tetrahydrofuran-3-ol in place of tetrahydro-2H-pyran-4-ol. The title compounds was isolated as a 1:1 mixture of trans diastereomers. MS APCI (+) m/z 449 (M+1) detected.

Example 36

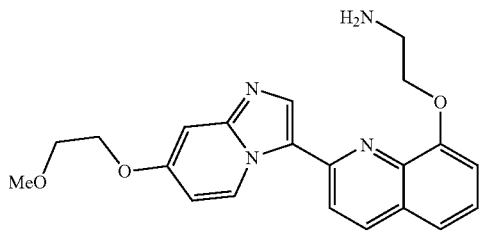

2-(2-(7-(2-methoxyethoxy)imidazo[1.2-a]pyridin-3-yl)quinolin-8-yloxy)ethanamine

To 2-(7-(2-methoxyethoxy)imidazo[1,2-a]pyridin-3-yl)quinolin-8-ol (50 mg, 0.15 mmol) in DMF (3 mL) was added 4 angstrom molecular sieves (2 g), tert-butyl 2-bromoethylcarbamate (40 mg, 0.18 mmol), t-butylammonium iodide (3 mg) and cesium hydroxide hydrate (50 mg, 0.30 mmol). The reaction mixture was stirred overnight, then dilute with EtOAc/H$_2$O (10 mL/10 mL). The aqueous layer was extracted with EtOAc. The combined organic layers were dried (Na$_2$SO$_4$), filtered, and concentrated to give crude, N-Boc-protected product, to which was added DCM (1 mL) and TFA (1 mL). This mixture was stirred for 30 minutes and then concentrated. The residue was purified by silica gel chromatography, eluting with DCM/MeOH/NH$_4$OH (10:1: 0.1) to provide the desired product (20 mg). APCI (+) m/z 379.2 (M+1) detected.

Example 37

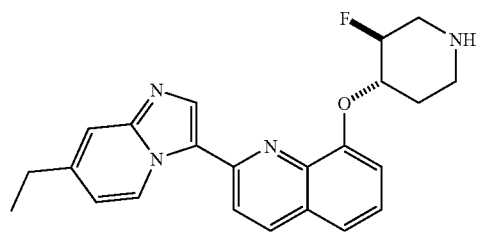

2-(7-ethylimidazo[1,2-a]pyridin-3-yl)-8-((trans)-3-fluoropiperidin-4-yloxy)quinoline 1. Preparation of 2-(7-ethylimidazo[1,2-a]pyridin-3-yl)quinolin-8-ol Step 1A: Preparation of 7-ethylimidazo[1.2-a]pyridine: A mixture of 4-ethylpyridin-2-amine (3.21 g, 8.19 mmol), and chloroacetaldehyde (50% aqueous solution, 2.6 ml, 10.5 mmol) in EtOH (10 ml) was refluxed vigorously for 12 hours. The reaction mixture was concentrated, and the residue was suspended in saturated aqueous sodium bicarbonate solution. The aqueous mixture was extracted with CH$_2$Cl$_2$ and EtOAc, and the combined organic extracts were dried over Na$_2$SO$_4$, filtered and concentrated to afford the desired product (1.18 g, 98% yield) as a viscous oil. MS APCI (+) m/z 147.2 (M+1) detected.

Step 1B: Preparation of 8-(benzyloxy)-2-(7-ethylimidazo[1.2-a]pyridin-3-yl)quinoline: A mixture of 7-ethylimidazo[1,2-a]pyridine (1.18 g, 8.06 mmol), 8-benzyloxy-2-chloroquinoline (2.17 g, 8.06 mmol), potassium carbonate (2.23 g, 16.2 mmol), palladium (II) acetate (90.5 mg, 0.40 mmol), tetrakis(triphenylphosphine)palladium (0) (466 mg, 0.40 mmol), 1,4-dioxane (33 ml) and water (0.33 ml) was heated under a nitrogen atmosphere overnight. The reaction mixture was diluted with water, extracted with CH$_2$Cl$_2$ and EtOAc, and the combined organic extracts were dried over Na$_2$SO$_4$, filtered and concentrated to afford the desired product (3.45 g) as a solid. MS APCI (+) m/z 380.2 (M+1) detected.

Step 1C: Preparation of 2-(7-ethylimidazo[1,2-a]pyridin-3-yl)quinolin-8-ol: A suspension of 8-(benzyloxy)-2-(7-ethylimidazo[1,2-a]pyridin-3-yl)quinoline (3.06 g, 8.06 mmol), Pearlman's catalyst (20% wt Pd, 283 mg) and ammonium formate (5.08 g, 80.6 mmol) in MeOH (50 ml) was degassed under nitrogen and heated at 80° C. for three hours, followed by stirring at ambient temperature overnight. The reaction mixture was poured into excess water and extracted with CH$_2$Cl$_2$ and EtOAc. The combined organic extracts were dried over Na$_2$SO$_4$, filtered and concentrated. The crude product was purified by silica gel chromatography (eluting with MeOH/CH$_2$Cl$_2$) to afford a mixture of starting material and desired product. This mixture was resubmitted to the original reaction conditions and refluxed for four hours. The reaction mixture was poured into excess water and extracted with CH$_2$Cl$_2$ and EtOAc. The combined organic extracts were dried over Na$_2$SO$_4$, filtered and concentrated to afford the title compound (768 mg, 33% yield) as a solid. MS APCI (+) m/z 290.3 (M+1) detected.

Step 2: Preparation of 2-(7-ethylimidazo[1,2-a]pyridin-3-yl)-8-((trans)-3-fluoropiperidin-4-yloxy)quinoline: Prepared according to the procedure for Example 16, using (cis)-tert-butyl 3-fluoro-4-(methylsulfonyloxy)piperidine-1-carboxylate in place of tert-butyl 2-((methylsulfonyloxy)methyl)morpholine-4-carboxylate and 2-(7-ethylimidazo[1,2-a]pyridin-3-yl)quinolin-8-ol in place of 2-(7-(2-methoxyethoxy)imidazo[1,2-a]pyridin-3-yl)quinolin-8-ol. MS APCI (+) m/z 391.2 (M+1) detected.

Example 38

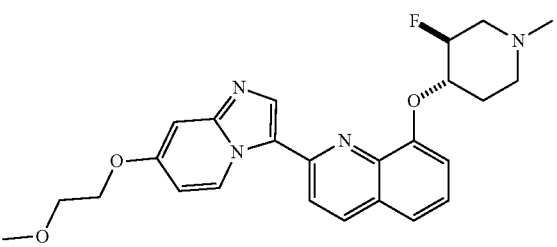

8-((trans)-3-fluoro-1-methylpiperidin-4-yloxy)-2-(7-(2-methoxyethoxy)imidazo[1,2-a]pyridin-3-yl)quinoline To a solution of 8-((trans)-3-fluoropiperidin-4-yloxy)-2-(7-(2-methoxyethoxy)imidazo[1,2-a]pyridin-3-yl)quinoline (Example 20; 185 mg, 0.42 mmol) in CH$_2$Cl$_2$ (5 mL) was added formaldehyde (316 µL, 37% in water, 4.2 mmol) followed by acetic acid (30 µL, 0.51 mmol) and sodium triacetoxyborohydride (270 mg, 1.27 mmol). The mixture was stirred vigorously at ambient temperature for 48 hours, then treated with 10% aq. K$_2$CO$_3$ (20 mL) and stirred for 10 minutes. The mixture was extracted with CH$_2$Cl$_2$, and the combined organic phases were washed with brine, dried over Na$_2$SO$_4$, filtered and concentrated. The residue was purified via flash column chromatography using gradient elution (CH$_2$Cl$_2$ to 2% MeOH/CH$_2$Cl$_2$ to 5% MeOH/CH$_2$Cl$_2$) then dissolved in CHCl$_3$ (5 mL) and treated with 4N HCl/dioxane (2 mL). After stirring for 20 minutes at ambient temperature the mixture was concentrated. The residue was triturated with ether, filtered and dried in vacuo to provide 136 mg (61%) of desired product as the di-HCl salt as a solid. MS APCI (+) m/z 451.2 (M+1) detected.

Example 39

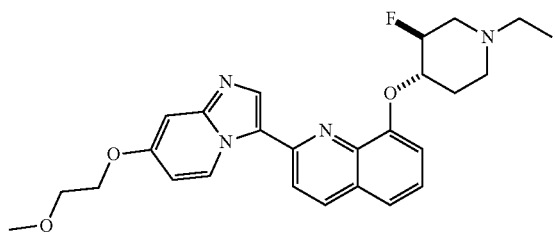

8-((trans)-1-ethyl-3-fluoropiperidin-4-yloxy)-2-(7-(2-methoxyethoxy)imidazo[1,2-a]pyridin-3-yl)quinoline Prepared from 8-((trans)-3-fluoropiperidin-4-yloxy)-2-(7-(2-methoxyethoxy)imidazo[1,2-a]pyridin-3-yl)quinoline according to the procedure for Example 29, using acetaldehyde in place of formaldehyde. MS APCI (+) m/z 465.1 (M+1) detected.

Example 40

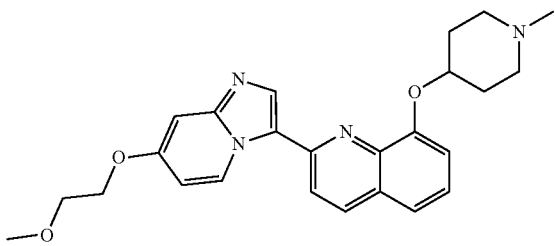

2-(7-(2-methoxyethoxy)imidazo[1,2-a]pyridin-3-yl)-8-(1-methylpiperidin-4-yloxy)quinoline Prepared according to the procedure for Example 38, using 2-(7-(2-methoxyethoxy)imidazo[1,2-a]pyridin-3-yl)-8-(piperidin-4-yloxy)quinoline (prepared as in Example 3) in place of 8-((trans)-3-fluoropiperidin-4-yloxy)-2-(7-(2-methoxyethoxy)imidazo[1,2-a]pyridin-3-yl)quinoline. MS APCI (+) m/z 433.2 (M+1) detected.

Example 41

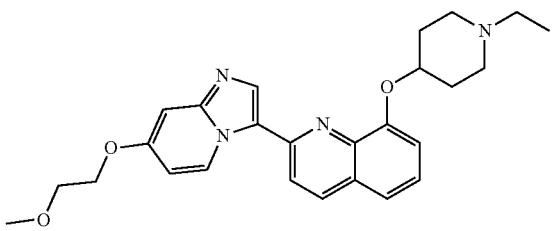

8-(1-ethylpiperidin-4-yloxy)-2-(7-(2-methoxyethoxy)imidazo[1,2-a]pyridin-3-yl)quinoline Prepared according to the procedure for Example 38, using acetaldehyde in place of formaldehyde. MS APCI (+) m/z 447.1 (M+1) detected.

Example 42

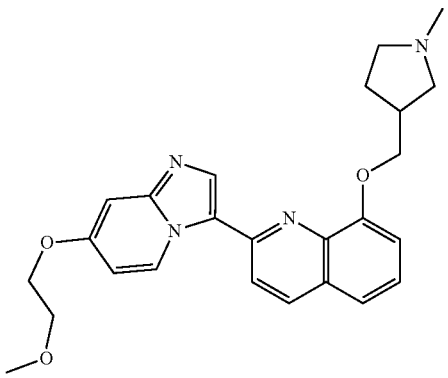

2-(7-(2-methoxyethoxy)imidazo[1,2-a]pyridin-3-yl)-8-((1-methylpyrrolidin-3-yl)methoxy)quinoline To a solution of 2-(7-(2-methoxyethoxy)imidazo[1,2-a]pyridin-3-yl)quinolin-8-ol (300 mg, 0.90 mmol) in anhydrous THF (15 ml) were added at ambient temperature under a nitrogen atmosphere triphenylphosphine (352 mg, 1.34 mmol), (1-methylpyrrolidin-3-yl) methanol (155 mg, 1.34 mmol) and diethyl azodicarboxylate (0.21 ml, 1.34 mmol). The reaction mixture was stirred at ambient temperature under nitrogen atmosphere overnight. The mixture was treated with saturated aqueous sodium bicarbonate solution (20 mL) and extracted with CH$_2$Cl$_2$ and EtOAc. The combined organic extracts were dried over anhydrous Na$_2$SO$_4$, filtered and concentrated to afford the crude product. The crude product was purified by column chromatography on silica gel (elution with 10% MeOH/CH$_2$Cl$_2$) to afford partially purified product. This material was purified by silica gel chromatography (eluting with 10% 7N NH$_3$/MeOH/CH$_2$Cl$_2$) to provide the title compound (34.2 mg, 9% yield) as a solid. MS ESI (+) m/z 433.2 (M+1) detected.

Example 43

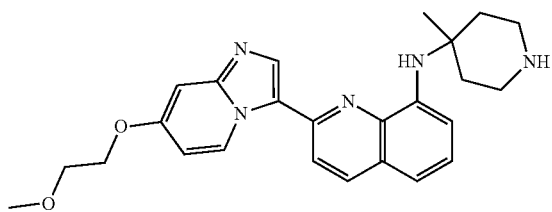

2-(7-(2-methoxyethoxy)imidazo[1,2-a]pyridin-3-yl)-
N-(4-methylpiperidin-4-yl)quinolin-8-amine Step A: Preparation of tert-butyl 4-(2-(7-(2-methoxyethoxy)imidazo[1,2-a]pyridin-3-yl)quinolin-8-ylamino)-4-methylpiperidine-1-carboxylate: Prepared according the procedure for Example 31, Step 2E, using tert-butyl 4-amino-4-methylpiperidine-1-carboxylate (Barth, W. E.; et al.; WO 0140217) in place of (cis)-tert-butyl 4-amino-3-fluoropiperidine-1-carboxylate. MS APCI (+) m/z 532.1 (M+1) detected.

Step B: Preparation of 2-(7-(2-methoxyethoxy)imidazo[1,2-a]pyridin-3-yl)-N-(4-methylpiperidin-4-yl)quinolin-8-amine: Prepared according to the procedure for Example 31, Step 2F, using tert-butyl 4-(2-(7-(2-methoxyethoxy)imidazo[1,2-a]pyridin-3-yl)quinolin-8-ylamino)-4-methylpiperidine-1-carboxylate. $^1$H NMR (400 MHz, CD$_3$OD) δ 9;83 (d, J=7.5 Hz, 1H), 8.25-8.18 (m, 2H), 7.94 (d, J=8.6 Hz, 1H), 7.37 (t, J=7.8 Hz, 1H), 7.19 (d, J=8.3 Hz, 1H), 7.11-7.05 (m, 2H), 6.91 (dd, 1H), 4.30-4.24 (m, 2H), 3.85-3.79 (m, 2H), 3.45 (s, 3H), 3.43-3.30 (m, 4H), 2.57-2.46 (m, 2H), 2.11-1.99 (m, 2H), 1.59 (s, 3H). MS APCI (+) m/z 432.0 (M+1) detected.

Example 44

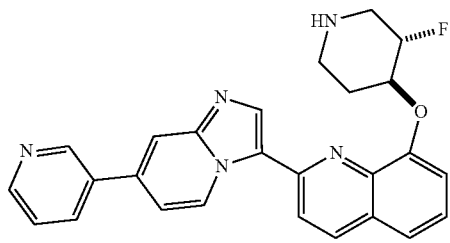

8-((trans)-3-fluoropiperidin-4-yloxy)-2-(7-(pyridin-3-yl)imidazo[1,2-a]pyridin-3-yl)quinoline Step A: Preparation of 7-bromoimidazo[1,2-a]pyridine: A solution of 4-bromopyridin-2-amine (1.00 g, 5.78 mmol) and 2-chloroacetaldehyde (50% wt aqueous solution, 1.83 ml, 14.45 mmol) in absolute ethanol (9.5 ml) was refluxed for 12 hours, and then allowed to cool to ambient temperature overnight. The reaction mixture was concentrated under reduced pressure and carefully re-suspended in saturated aqueous bicarbonate solution (100 ml). The resulting mixture was extracted thoroughly with DCM and EtOAc, and the combined organic extracts were dried over anhydrous sodium sulfate and concentrated to afford 1.31 g of a solid. The solid was purified by silica gel chromatography (eluting with 3% MeOH-chloroform) to afford the desired compound (0.808 g, 71% yield). MS APCI (+) m/z 197.1 and 199.1 (M+1 for each isotope) detected.

Step B: Preparation of 7-(pyridin-3-yl)imidazo[1,2-a]pyridine: A suspension of potassium carbonate (0.351 g, 2.54 mmol), pyridin-3-ylboronic acid (68.6 mg, 0.558 mmol), 7-bromoimidazo[1,2-a]pyridine (0.100 g, 0.508 mmol) and tetrakis(triphenylphosphine)palladium (0) (29.3 mg, 0.025 mmol) in 6.5 ml of a 1:1:4.5 mixture of water:dimethylformamide:acetonitrile was degassed thoroughly under a nitrogen atmosphere, and heated at 60° C. for 18 hours. The reaction mixture was poured in water (50 ml) and extracted with dichloromethane and EtOAc. The combined organic extracts were dried over anhydrous sodium sulfate and concentrated to afford a solid. The solid was purified by silica gel chromatography (eluting with 6% MeOH-chloroform) to afford the desired compound (74.1 mg, 75% yield). MS APCI (+) m/z 196.3 (M+1) detected.

Step C: Preparation of 2-(7-(pyridin-3-yl)imidazo[1,2-a]pyridin-3-yl)quinolin-8-ol: Prepared according to the procedure for Example 31, steps 1A to 1D using 7-(pyridin-3-yl)imidazo[1,2-a]pyridine in place of 7-(2-methoxyethoxy)-imidazo[1,2-a]pyridine.

Step D: Preparation of tert-butyl trans-3-fluoro-4-(2-(7-(pyridin-3-yl)imidazo[1,2-a]pyridin-3-yl)quinolin-8-yloxy)piperidine-1-carboxylate: A mixture of 2-(7-(pyridin-3-yl)imidazo[1,2-a]pyridin-3-yl)quinolin-8-ol (30.2 mg, 0.089 mmol), tert-butyl cis-3-fluoro-4-(methylsulfonyloxy)piperidine-1-carboxylate (39.8 mg, 0.134 mmol) and Cs$_2$CO$_3$ (43.6 mg, 0.134 mmol) in DMA (7.78 mg, 0.089 mmol) was heated to 100° C. for 1 hour. The reaction mixture was cooled to ambient temperature and diluted with water and EtOAc. The combined organic layers were dried over Na$_2$SO$_4$, filtered and concentrated. The residue was purified by preparative TLC, eluting with 10% MeOH 0.5% NH$_4$OH in DCM to provide the desired product (22 mg, 46% yield).

Step E: Preparation of 8-(trans-3-fluoropiperidin-4-yloxy)-2-(7-(pyridin-3-yl)imidazo[1,2-a]pyridin-3-yl)quinoline: tert-Butyl trans-3-fluoro-4-(2-(7-(pyridin-3-yl)imidazo[1,2-a]pyridin-3-yl)quinolin-8-yloxy)piperidine-1-carboxylate (22 mg, 0.041 mmol) was added to 2 ml DCM at ambient temperature. TFA (2 mL) was added and the reaction was stirred for 1 hour, then diluted with DCM and water. The mixture was washed with 1N NaOH amine and extracted with DCM, followed by extraction with 20% IP A/Chloroform. The combined organic layers were dried over Na$_2$SO$_4$, filtered and concentrated. The residue was purified by preparative TLC, eluting with 15% MeOH/0.5% NH$_4$OH in DCM to provide the desired product as a film (5.6 mg, 31% yield). MS APCI (+) m/z 440.1 (M+1) detected.

Example 45

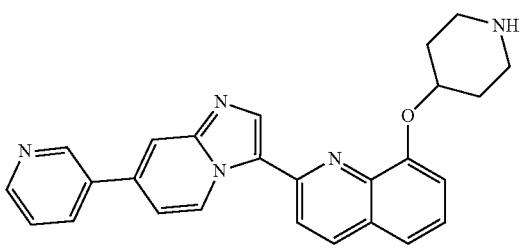

8-(piperidin-4-yloxy)-2-(7-(pyridin-3-yl)imidazo[1,2-a]pyridin-3-yl)quinoline

Compound was isolated during purification of the compound prepared according to Example 44. MS APCI (+) m/z 422.1 (M+1) detected.

Example 46

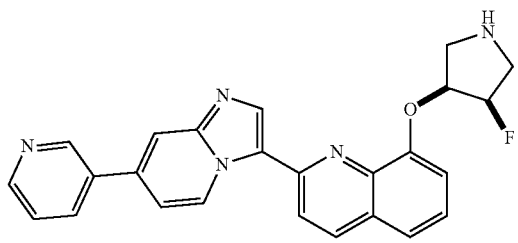

8-((cis)-4-fluoropyrrolidin-3-yloxy)-2-(7-(pyridin-3-yl)imidazo[1,2-a]pyridin-3-yl)quinoline Step A: Preparation of (trans)-naphthalen-2-ylmethyl 3-fluoro-4-hydroxypyrrolidine-1-carboxylate: A plastic (HDPE) bottle was charged with naphthalen-2-ylmethyl 6-oxa-3-azabicyclo[3.1.0]hexane-3-carboxylate (945 mg, 3.509 mmol) and HF-pyridine (264 μL, 10.527 mmol) in DCM (17.55 ml, 3.509 mmol) and the reaction mixture was stirred for 36 hours at ambient temperature. The reaction was slowly quenched with aqueous saturated NaHCO₃ and diluted with water and DCM. The reaction mixture was extracted with DCM, and the combined organics layers were dried over Na₂SO₄ and concentrated to give the product as an oil (237 mg, 23.3% yield)

Step B: Preparation of (trans)-naphthalen-2-ylmethyl 3-fluoro-4-(tosyloxy)pyrrolidine-1-carboxylate: A flask was charged with (trans)-naphthalen-2-ylmethyl 3-fluoro-4-hydroxypyrrolidine-1-carboxylate (237 mg, 0.819 mmol), TEA (0.343 ml, 2.458mmol) and DMAP (10.0 mg, 0.082 mmol) in DCM (4.3 ml, 0.86 mmol). The reaction mixture was cooled to 0° C., and 4-methylbenzene-1-sulfonyl chloride (234 mg, 1.23 mmol) was added. The reaction was warmed to ambient temperature and stirred for 3 hours. The reaction was diluted with water and extracted with DCM. The combined organic layers were dried over Na₂SO₄ and concentrated. The residue was purified by flash column chromatography, eluting with 0-5% MeOH in DCM to give the product as an oil (160 mg, 44% yield).

Step C: Preparation of (cis)-naphthalen-2-ylmethyl-2-fluoro-4-(2-(7-(pyridin-3-yl)imidazo[1,2-a]pyridin-3-yl)quinolin-8-yloxy)pyrrolidine-1-carboxylate: A flask was charged with 2-(7-(pyridin-3-yl)imidazo[1,2-a]pyridin-3-yl)quinolin-8-ol (97.7 mg, 0.289 mmol), (trans)-naphthalen-2-ylmethyl 3-fluoro-4-(tosyloxy)pyrrolidine-1-carboxylate (160 mg, 0.361 mmol) and Cs₂CO₃ (282 mg, 0.866 mmol) in DMF (1443 μL 0.289 mmol). The mixture was heated to 70° C. for 4 hours, then diluted with water and EtOAc. The aqueous layer was extracted with EtOAc, and the combined organic layers were dried over Na₂SO₄, filtered and concentrated. The residue was purified by silica gel chromatography to give the desired product (50 mg, 28% yield). MS APCI (+) m/z 610.2 (M+1) detected.

Step D: Preparation of 8-((cis)-4-fluoropyrrolidin-3-yloxy)-2-(7-(pyridin-3-yl)imidazo[1,2-a]pyridin-3-yl)quinoline: A solution of cis-naphthalen-2-ylmethyl 3-fluoro-4-(2-(7-(pyridin-3-yl)imidazo[1,2-a]pyridin-3-yl)quinolin-8-yloxy)pyrrolidine-1-carboxylate (2.0 mg, 0.003 mmol) in 1 ml DCM was cooled to 0° C. and 1 ml TFA was added. The mixture was stirred for 16 hours at ambient temperature and then concentrated. The residue was purified by preparative TLC, eluting with 15% MeOH/0.5% NE₄OH in chloroform to give the title compound as a film (1.1 mg, 78% yield). MS APCI (+) m/z 426.2 (M+1) detected.

Example 47

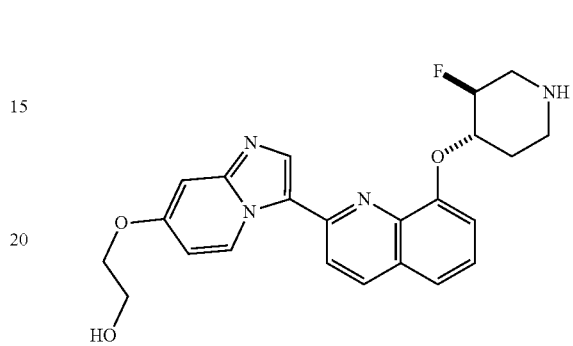

2-(3-(8-(trans-3-fluoropiperidin-4-yloxy)quinolin-2-yl)imidazo[1,2-a]pyridin-7-yloxy)ethanol To a flask containing 8-(-3-fluoropiperidin-4-yloxy)-2-(7-(2-methoxyethoxy)imidazo[1,2-a]pyridin-3-yl)quinoline (Prepared according to Example 20; 0.062 g, 0.14 mmol) was added CH₂Cl₂ (14 mL) and the solution was cooled to −78° C. BBr₃ (1.0M in CH₂Cl₂, 0.71 ml, 0.71 mmol) was added dropwise and the reaction stirred at −78° C. for 1 hour, then slowly warmed to 0° C. over 2.0 hours, then warmed to ambient temperature and stirred for 0.5 hours. The reaction was quenched by the addition of a saturated aqueous NaHCO₃ solution (15 mL) and the layers were separated. The aqueous phase was extracted with CH₂Cl₂ and the combined organic phases were washed with brine and dried over Na₂SO₄. The mixture was filtered and concentrated in vacuo and purified via column chromatography (6% NH₄OH in MeOH/CH₂Cl₂, 2% to 20% linear gradient) to afford 0.015 g (0.25%) of the title compound as a solid. MS APCI (+) m/z 423.2 [M+H]⁺ detected.

Example 48

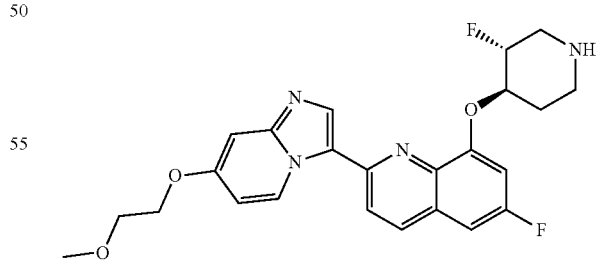

6-fluoro-8-((3R,4R)-3-fluoropiperidin-4-yloxy)-2-(7-(2-methoxyethoxy)imidazo[1,2-a]pyridin-3-yl)quinoline Step 1A: Preparation of 6-fluoro-2-methylquinolin-8-ol: 2-Amino-5-fluorophenol (13.0 g, 102 mmol) was dissolved in 6N HCl (78 mL) and heated to reflux. The solution was treated with (E)-but-2-enal (8.8 ml, 107 mmol) in 1 mL portions over 1 hour. The reaction was heated at reflux for 13 hours. The reaction mixture was cooled and adjusted to pH 8 with concentrated NH$_4$OH. The reaction was diluted with ethyl acetate, stirred for 30 minutes then filtered through a nylon membrane (0.45 µM). The filtrate was separated and the aqueous was washed with ethyl acetate. The combined organics were washed with saturated NaHCO$_3$, saturated NaCl, dried over Na$_2$SO$_4$ and concentrated in vacuo to a thick dark oil (19 g). MS APCI (+) m/z 178.1 (M+1) detected.

Step 1B: Preparation of 6-fluoro-2-methyl-8-(triisopropylsilyloxy)quinoline: 6-Fluoro-2-methylquinolin-8-ol (19.0 g, 107 mmol) was dissolved in methylene chloride (300 mL) and treated with 1H-imidazole (10.9 g, 160 mmol) and triisopropylsilyl trifluoromethanesulfonate (33.1 ml, 123 mmol). The reaction was stirred at ambient temperature for 13 hours. The reaction mixture was quenched with saturated NH$_4$Cl and separated. The organic layer was washed twice with saturated NH$_4$Cl, dried over Na$_2$SO$_4$ and concentrated in vacuo (35 g).

Step 1C: Preparation of 6-fluoro-8-(triisopropylsilyloxy)quinoline-2-carbaldehyde: 6-Fluoro-2-methyl-8-(triisopropylsilyloxy)quinoline (1.76 g, 5.29 mmol) was dissolved in dioxane (58 mL) and water (0.49 mL). The reaction was treated with selenium dioxide (0.76 g, 6.8 mmol) and the mixture was heated to reflux for 13 hours. The mixture was cooled and filtered through GF/F paper. The filtered solids were washed with Et$_2$O then all the filtrates were concentrated in vacuo. The crude mixture was chromatographed on silica gel, eluting with a gradient of 1-5% Et$_2$O/hexanes, (0.515 g). $^1$H NMR (400 MHz, CDCl$_3$) δ 10.19 (s, 1H), 8.18 (d, J=8.7 Hz, 1H), 8.01 (d, J=8.4 Hz, 1H), 7.14-7.08 (m, 1H), 7.06-7.00 (m, 1H), 1.52-1.41 (m, 3H), 1.16 (d, 18H).

Step 1D: Preparation of 6-fluoro-2-(2-methoxyvinyl)-8-(triisopropylsilyloxy)quinoline: (Methoxymethyl)triphenylphosphonium chloride (8.355 g, 24.37 mmol) was dissolved in THF (130 mL), cooled to 0° C., and treated dropwise with a solution of 1M KOtBu in THF (26.5 ml, 26.5 mmol). The mixture was warmed and stirred at ambient temperature for 15 minutes. A solution of 6-fluoro-8-(triisopropylsilyloxy)quinoline-2-carbaldehyde (7.70 g, 22.1 mmol) dissolved in THF (15 mL) was added. The reaction was stirred at ambient temperature for 10 hours. The mixture was concentrated in vacuo and applied directly to a column of SiO$_2$ eluting with a stepped gradient from 1-4% Et$_2$O/hexanes, (4.75 g). $^1$H NMR (400 MHz, CDCl$_3$) δ 7.86 (d, J=8.6 Hz, 1H), 7.74 (d, J=13 Hz, 1H), 7.23 (d, J=8.6 Hz, 1H), 6.93 (dd, J$_1$=2.8 Hz, J$_2$=8.7 Hz, 1H), 6.88 (dd, J$_1$=2.7 Hz, J$_2$=10.2 Hz, 1H), 6.02 (d, J=12.5 Hz, 1H), 3.77 (s, 3H), 1.47-1.38 (m, 3H), 1.15 (d, 18H).

Step 2A: Preparation of 2-chloro-4-(2-methoxyethoxy)pyridine: A mixture of 2-chloro-4-nitropyridine (43.6 g, 275 mmol) and 2-methoxyethanol (325 ml, 425 mmol) was cooled to 0° C. Potassium 2-methylpropan-2-olate (35.7 g, 302 mmol) was added and the resulting mixture was stirred while warming to ambient temperature over 2 hours. The reaction mixture was concentrated under reduced pressure followed by dilution with 500 ml of water. The resulting mixture was extracted with dichloromethane. The combined organic layers were dried over MgSO$_4$ and concentrated under reduced pressure to produce the desired compound as an oil (50.2 g). MS APCI (+) m/z 188 and 189.9 (M+1 of each isotope) detected.

Step 2B: Preparation of 4-(2-methoxyethoxy)pyridin-2-amine: A steady stream of nitrogen was passed through a mixture of 2-chloro-4-(2-methoxyethoxy)pyridine (50.1 g, 267 mmol), Pd$_2$dba$_3$ (4.89 g, 5.34 mmol), XPHOS (5.09 g, 10.7 mmol) and tetrahydrofuran (445 ml) for 10 minutes. To the resulting degassed mixture was added lithium bis(trimethylsilyl)amide (561 ml, 561 mmol). After addition, the resulting mixture was heated to 60° C. for 18 hours. The reaction was cooled to ambient temperature and diluted with 1 N hydrochloric acid (200 mL). The resulting solution was washed twice with 500 ml of methyl-tert-butyl ether. The pH of the aqueous layer was adjusted to 11 with 6 N NaOH and extracted with dichloromethane. The combined organic layers were dried over MgSO$_4$ and concentrated under reduced pressure to yield title compound (35 g) MS APCI (+) m/z 169 (M+1) detected.

Step 2C: Preparation of 6-fluoro-2-(7-(2-methoxyethoxy)imidazo[1,2-a]pyridin-3-yl)quinolin-8-ol: 6-Fluoro-2-(2-methoxyvinyl)-8-(triisopropylsilyloxy)quinoline (2.5 g, 6.6 mmol) was dissolved in THF (10.3 mL) and water (2.6 mL) and cooled to 0° C. The solution was treated dropwise with a solution of freshly recrystallized N-bromosuccinimide (1.24 g, 6.99 mmol) dissolved in THF (7 mL) and water (1.75 mL). The reaction was stirred at 0° C. for 20 minutes then warmed and stirred at ambient temperature for 2.5 hours. The reaction was treated with 4-(2-methoxyethoxy)pyridin-2-amine (1.12 g, 6.65 mmol) and the mixture was heated to reflux overnight. The mixture was cooled and solids formed in the flask. Chloroform (50 mL), ethyl acetate (300 mL), and water (50 mL) were added to disperse the solids and the undissolved solids were collected by filtration and washed with ethyl acetate and water, then air-dried, (1.2 g). MS APCI (+) m/z 354.1 (M+1) detected.

Step A: Preparation of (3R,4R)-naphthalen-2-ylmethyl 3-fluoro-4-(6-fluoro-2-(7-(2-methoxyethoxy)imidazo[1,2-a]pyridin-3-yl)quinolin-8-yloxy)piperidine-1-carboxylate: (3R,4S)-naphthalen-2-ylmethyl 3-fluoro-4-(methylsulfonyloxy)piperidine-1-carboxylate (170 mg, 0.44 mmol) (Example 20, Step F, derived from Peak 2), 6-fluoro-2-(7-(2-methoxyethoxy)imidazo[1,2-a]pyridin-3-yl)quinolin-8-ol (173 mg, 0.49 mmol) and Cs$_2$CO$_3$ (290 mg, 0.89 mmol) were weighed into a flask and suspended in 10 mL of DMA. The reaction was then heated to 90° C. overnight. The reaction was then cooled to ambient temperature, followed by workup with water and EtOAc. The combined organic phase was concentrated in vacuo, followed by flash column chromatography (1-10% MeOH/DCM) affording the desired product as a brown semi-solid (270 mg, 0.43 mmol, 95%). MS APCI (+) m/z 639.2 and 640.1 (M+1/+3) detected.

Step B: Preparation of 6-fluoro-8-((3R,4R)-3-fluoropiperidin-4-yloxy)-2-(7-(2-methoxyethoxy)imidazo[1,2-a]pyridin-3-yl)quinoline: Pd/C (45 mg, 0.042 mmol) 10% wet was added to a solution of (3R,4R)-naphthalen-2-ylmethyl 3-fluoro-4-(6-fluoro-2-(7-(2-methoxyethoxy)imidazo[1,2-a]pyridin-3-yl)quinolin-8-yloxy)piperidine-1-carboxylate (270 mg, 0.42 mmol) in a 1:1 mixture of EtOH/EtOAc (10 mL) and 500 uL of 6 N HCl. The mixture was purged with H$_2$, and then allowed to stir under a balloon of hydrogen for 48 hours. The mixture was filtered through GF paper removing the desired product salt as a precipitate, with the palladium catalyst. The combined solids were washed into a beaker with 30 mL of MeOH and the palladium removed by subsequent filtration through GF filter paper. The organic phase was concentrated in vacuo, followed by flash column chromatography (1-20% MeOH/DCM (4% NH$_4$OH). The resulting product was dissolved in chloroform and subject to four equivalents of 4 M HCl in dioxane. The desired product was then isolated as the bis-HCl salt. MS APCI (+) m/z 455.2 (M+1) detected.

Example 49

8-((trans)-3-fluoropiperidin-4-yloxy)-2-(7-(pyrimidin-5-yl)imidazo[1,2-a]pyridin-3-yl)quinoline Step A: Preparation of 7-(pyrimidin-5-yl)imidazo[1,2-a]pyridine: Prepared according to the procedure for Example 44, Step B using pyrimidin-5-ylboronic acid in place of pyridin-3-ylboronic acid. MS APCI (+) m/z 197 (M+1) detected.

Step B: Preparation of benzyl trans-3-fluoro-4-(2-(7-(pyrimidin-5-yl)imidazo[1,2-a]pyridin-3-yl)quinolin-8-yloxy)piperidine-1-carboxylate: Prepared according to the procedures of Example 44, steps C to D, using 7-(pyrimidin-5-yl)imidazo[1,2-a]pyridine in place of 7-(pyridin-3-yl)imidazo[1,2-a]pyridine. MS APCI (+) m/z 575 (M+1) detected.

Step C. Preparation of 8-((trans)-3-fluoropiperidin-4-yloxy)-2-(7-(pyrimidin-5-yl)imidazo[1,2-a]pyridin-3-yl)quinoline: To a solution of (trans)-benzyl 3-fluoro-4-(2-(7-(pyrimidin-5-yl)imidazo[1,2-a]pyridin-3-yl)quinolin-8-yloxy)piperidine-1-carboxylate (0.005 g, 0.009 mmol) in 0.80 mL 1:1 THF:EtOH was added 5% Pd/C (0.009 g, 0.004 mmol). Hydrogen was bubbled through the reaction mixture, and the reaction was stirred under a hydrogen balloon for 15 hours at ambient temperature. The reaction mixture was then vacuum filtered through compressed Celite, rinsed with MeOH, and the filtrate was concentrated and dried in vacuo. The resulting solids were dissolved in 1 mL DCM, and this solution was added dropwise to a vigorously stirring solution of 1 mL 2 M HCl in ether in 10 mL ether, causing precipitation. The mixture was concentrated and dried in vacuo to give the title compound as the dihydrochloride salt (0.002 g, 0.003 mmol, 40% yield) as a solid. MS APCI (+) m/z 441 (M+1) detected.

Example 50

8-((trans)-3-fluoropiperidin-4-yloxy)-2-(7-(4-methylpyridin-3-yl)imidazo[1,2-a]pyridin-3-yl)quinoline Step A: Preparation of (trans)-benzyl 3-fluoro-4-(2-(7-(4-methylpyridin-3-yl)imidazo[1,2-a]pyridin-3-yl)quinolin-8-yloxy)piperidine-1-carboxylate: Prepared according the procedures of Example 44, steps A through D, using 4-methylpyridin-3-ylboronic acid in place of pyridin-3-ylboronic acid. MS APCI (+) m/z 588 (M+1) detected.

Step B: Preparation of 8-((trans)-3-fluoropiperidin-4-yloxy)-2-(7-(4-methylpyridin-3-yl)imidazo[1,2-a]pyridin-3-yl)quinoline: The Cbz group can be removed using the conditions described for Example 49, Step C to give the title compound.

Example 51

5-fluoro-8-((3R,4R)-3-fluoropiperidin-4-yloxy)-2-(7-(2-methoxyethoxy)imidazo[1,2-a]pyridin-3-yl)quinoline Prepare according to the procedure of Example 48, using 2-amino-4-fluorophenol in place of 2-amino-5-fluorophenol.

What is claimed is:

1. A compound of general Formula I:

or a pharmaceutically acceptable salt thereof, wherein:
A is —Z—(CH$_2$)$_p$-(hetCyc$^{2a}$), —Z-(hetCyc$^{2b}$), Z—R$^{10}$ or Z—R$^{11}$;
Z is O or NH;
p is 0, 1, or 2;
hetCyc$^{2a}$ is a 5 or 6 membered heterocyclic ring optionally substituted with one or more R$^9$ groups;
hetCyc$^{2b}$ is a 7-12 membered spirocyclic or bridged heterobicyclic ring system optionally substituted with one or more R$^9$ groups;
R$^{10}$ is (1-6C)alkyl substituted with NR'R";
R$^{11}$ is (5-6C)cycloalkyl substituted with NR'R";
B is H, CN, OR$^h$, Ar$^1$, hetAr$^2$, C(O)NR'R$^j$, C(O)-hetCyc$^3$, C(O)NH(1-6C alkyl)-hetCyc$^3$, C(O)(1-6C alkyl)-hetCyc$^3$, SR$^k$, SO$_2$N(1-6C alkyl)$_2$, (1-6C alkyl)NR'R" or (1-3C)alkyl;

65

R$^1$, R$^2$, R$^3$ and R$^4$ are independently H, F, Cl, CN, Me, Et, isopropyl, cyclopropyl, C(O)NR'R", CH$_2$OH, or hetAr$^3$;
R$^{1a}$ is H, F, Cl, or Me;
R$^5$, R$^6$, R$^7$ and R$^8$ are independently H, F, Cl, CN or Me;
each R$^9$ is independently selected from halogen, CN, CF$_3$, (1-6C)alkyl, NR$^a$R$^b$, -(1-6C alkyl)NR$^a$R$^c$, OR$^a$, (1-6C alkyl)OR$^a$ [optionally substituted with amino], C(O)NR$^a$R$^c$, C(O)(CR$^x$R$^y$)NR$^a$R$^c$, NHC(O)R$^e$, NHC(O)(CR$^m$R$^n$)NR$^a$R$^c$, NHC(O)NR$^f$R$^g$, (1-6C alkyl)-hetAr$^1$, (1-6C alkyl)-hetCyc$^1$, oxo, and C(O)O(1-6C alkyl);
each R$^a$ is independently H or (1-6C)alkyl;
each R$^b$ is independently H, (1-6C)alkyl, (1-6C alkyl)OH, (3-6C)cycloalkyl, CH$_2$hetAr$^4$, (1-6C fluoroalkyl) or -(1-6C alkyl)-O-(1-6C alkyl),
  each R$^c$ is independently H, (1-6C)alkyl, (3-6C)cycloalkyl, or aryl;
each R$^e$ is independently (1-6C alkyl);
each R$^f$ and R$^g$ is independently H or (1-6C alkyl);
R$^h$ is H, CF$_3$, (1-6C)alkyl, (1-6Calkyl)-(3-6C cycloalkyl), (1-6C alkyl)-O-(1-6C alkyl), (1-6C alkyl)OH, (1-6C alkyl)-S-(1-6C alkyl), (1-6C alkyl)NR'R", hetCyc$^4$,(1-6C alkyl)hetCyc$^4$, (1-6C alkyl)aryl, or (1-6C alkyl)-hetAr$^5$;
R$^i$ is H or 1-6C alkyl;
R$^j$ is (1-6C)alkyl, (1-6C alkyl)-O-(1-6C alkyl), or (1-6C alkyl)-OH;
R$^k$ is (1-6C)alkyl, (3-6C)cycloalkyl, or (1-6C alkyl)-O-(1-6C alkyl);
R$^m$ and R$^n$ are independently H or (1-6C alkyl);
R$^x$ and R$^y$ are independently H or (1-6C alkyl),
or R$^x$ and R$^y$ together with the atom to which they are attached form a cyclopropyl ring;
Ar$^1$ is aryl optionally substituted with OH, O-(1-6C alkyl), C(O)$_2$(1-6C alkyl), or (1-6C alkyl)NR'R";
hetCyc$^1$ is a 5-6 membered heterocyclic ring which is optionally substituted with (1-6C)alkyl or OH;
hetCyc$^3$ and hetCyc$^4$ are independently a 5 or 6 membered heterocyclic ring optionally substituted with OH or —O(1-6C alkyl);
hetAr$^1$ and hetAr$^2$ are a 5-6 membered heteroaryl ring optionally substituted with one to three groups independently selected from (1-6C)alkyl, (3-6C)cycloalkyl, halogen, CN, CF$_3$, OCH$_2$F, OCF$_3$, O(1-6C alkyl), O(3-6C)cycloalkyl, and NR'R";
hetAr$^3$ and hetAr$^4$ are independently a 5-6 membered heteroaryl ring;
hetAr$^5$ is a 5-6 membered heteroaryl ring optionally substituted with (1-6C)alkyl; and
R' and R" are independently H or (1-6C)alkyl.

2. A compound of claim 1, wherein A is —NH(hetCyc$^{2a}$), —NH—(CH$_2$)-hetCyc$^{2a}$, or —NH—(CH$_2$)$_2$-hetCyc$^{2a}$, wherein said hetCyc$^{2a}$ is optionally substituted with one or more R$^9$ groups.

3. A compound of claim 1, wherein A is —O-hetCyc$^{2a}$, —O—(CH$_2$)-hetCyc$^{2a}$, or —O—(CH$_2$)$_2$-hetCyc$^{2a}$, wherein said hetCyc$^{2a}$ is optionally substituted with one or more R$^9$ groups.

4. A compound as defined in claim 1, wherein hetCyc$^{2a}$ is optionally substituted with one or more R$^9$ groups independently selected from halogen, —C(O)O(1-6C alkyl), (1-6C alkyl), and —OR$^2$.

5. A compound of claim 4, wherein hetCyc$^{2a}$ is optionally substituted with one or more R$^9$ groups independently selected from F, methyl, OH, —C(O)$_2$Me, and OMe.

6. A compound as defined in claim 1, wherein hetCyc$^{2a}$ is a pyrrolidinyl, piperidinyl or morpholinyl ring optionally substituted with one or more R$^9$ groups.

66

7. A compound of claim 1, wherein A is —O-hetCyc$^{2a}$ and hetCyc$^{2a}$ is a piperidinyl ring substituted with a fluoro group.

8. A compound of claim 1, wherein A is —NH(hetCyc$^{2b}$) or —O-(hetCyc$^{2b}$), wherein said hetCyc$^{2b}$ is optionally substituted with one or more R$^9$ groups.

9. A compound of claim 8, wherein hetCyc$^{2b}$ is 7-11 membered bridged aza- or diaza-heterocycle optionally substituted with one or more R$^9$ groups.

10. A compound according to claim 9, wherein R$^9$ is selected from halogen, (1-6C alkyl), OH, and —O(1-6C alkyl).

11. A compound of claim 10, wherein R$^9$ is selected from F, Me and OH.

12. A compound of claim 1, wherein A is Z—R$^{10}$.

13. A compound of claim 1, wherein A is Z—R$^{11}$.

14. A compound as defined in claim 1, wherein B is selected from OR$^h$, (1-3C)alkyl, and hetAr$^2$.

15. A compound of claim 14, wherein B is selected from —OCH$_2$CH$_2$OCH$_3$, —OCH$_2$CH$_2$OH, —OCH$_2$(cyclopropyl), ethyl, 2-pyridyl, 3-pyridyl, 4-pyridyl, 2-pyrimidyl,

[structures]

16. A compound as defined in claim 1, wherein B is OR$^h$.

17. A compound of claim 16, wherein B is selected from —OCH$_2$CH$_2$OCH$_3$, —OCH$_2$CH$_2$OH, —OCH$_2$(cyclopropyl),

[structures]

18. A compound of claim 17, wherein B is —OCH$_2$CH$_2$OCH$_3$.

19. A compound as defined in claim 1, wherein B is hetAr$^2$.

20. A compound of claim 19, wherein B is selected from 2-pyridyl, 3-pyridyl, 4-pyridyl, 2-pyrimidyl.

21. A compound of claim 20, wherein B is 3-pyridyl.

22. A compound as defined in claim 1, wherein R$^{1a}$ is H or F.

23. A compound as defined in claim 1, wherein R$^2$ is H or F.

24. A compound as defined in claim 1, wherein R$^3$ is H, methyl or oxazolyl.

25. A compound as defined in claim 1, wherein each of R$^5$, R$^6$, R$^7$ and R$^8$ is hydrogen.

26. A compound as defined in claim 1, wherein each of R$^1$ and R$^4$ is hydrogen.

27. A pharmaceutical composition, which comprises a compound of Formula I as defined in claim 1, or a pharmaceutically acceptable salt thereof, and a pharmaceutically acceptable diluent or carrier.

28. A process for the preparation a compound of claim 1, which comprises:
  (a) for a compound of the Formula I wherein A is —NH—(CH$_2$)$_n$(hetCyc$^{2a}$), —NH-(hetCyc$^{2b}$), —NHR$^{10}$ or —NHR$^{11}$, coupling a corresponding compound having the formula II

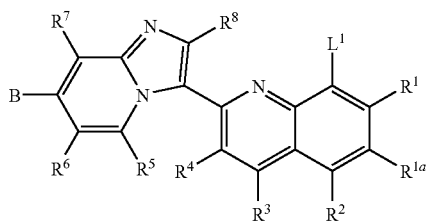

II wherein L¹ represents a leaving group or atom, with a compound having the formula $H_2N-(CH_2)_n hetCyc^{2a}$, $H_2N-hetCyc^{2b}$, $NH_2R^{10}$ or $NH_2R^{11}$, using a palladium catalyst and a ligand in the presence of a base; or (b) for a compound of Formula I where B is $OR^h$, reacting a corresponding compound having the Formula III

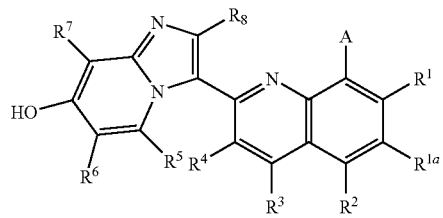

III with a compound of the formula $R^h$-$L^2$ wherein $L^2$ represents a leaving group in the presence of a base; or (c) for a compound of Formula I where B is $OR^h$, reacting a corresponding compound having the Formula III with a compound having the formula $R^h$—OH in the presence of a coupling reagent; or (d) for a compound of Formula I wherein A is —O—$(CH_2)_n$ hetCyc$^{2a}$, —O-hetCyc$^{2b}$, —$OR^{10}$ or —$OR^{11}$, reacting a corresponding compound having the formula IV

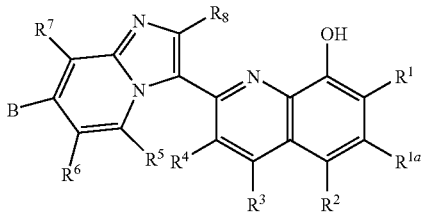

IV with a corresponding compound having the formula HO—$(CH_2)_n$hetCyc$^{2a}$, HO-hetCyc$^{2b}$, HOR$^{10}$ or HOR$^{11}$ in the presence of a coupling agent and triphenylphosphine in a suitable solvent; or (e) for a compound of Formula I wherein A is —O—$(CH_2)_n$ hetCyc$^{2a}$, reacting a compound of Formula IV with a compound having the formula $MeSO_2$—O—$(CH_2)_n$ hetCyc$^{2a}$ in the presence of a base; or (f) for a compound of Formula I wherein $R^3$ is hetAr$^3$ and hetAr$^3$ is oxazolyl, cyclizing a compound having the formula V

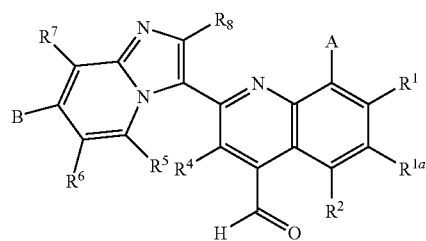

V with a compound having the formula

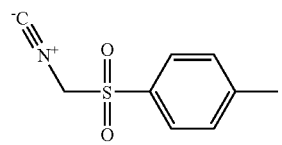

in the presence of a base; or (g) for a compound of Formula I wherein A is

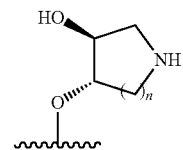

and n is 1 or 2, reacting a corresponding compound having the formula IV

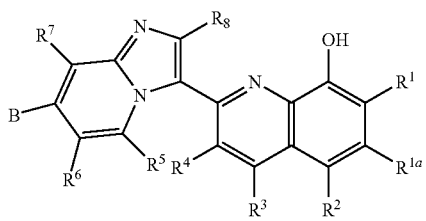

IV with a compound having the formula

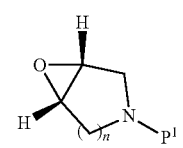

wherein n is 1 or 2 and P¹ is an amine protecting group, in the presence of a base; or (h) for a compound of Formula I wherein A is:

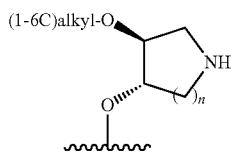

and n is 1 or 2, reacting a corresponding compound having the formula VII

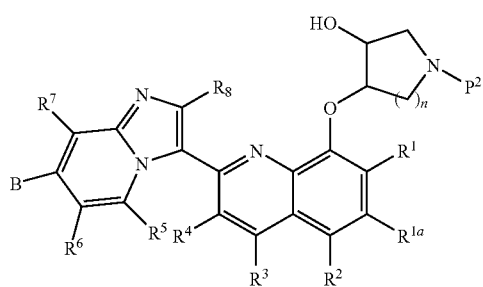

wherein n is 1 or 2 and $P^2$ is H or an amine protecting group, with a compound having the formula (1-6C alkyl)$L^3$ where $L^3$ is a leaving group or atom in the presence of a base; or (i) for a compound of Formula I wherein A is O-(1-6C alkyl)NR'R", reacting a compound having the formula IV

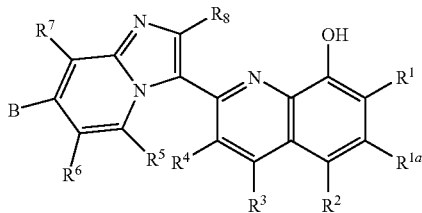

with a compound having the formula $L^4$-(1-6C alkyl)NR'R" where $L^4$ is a leaving group or atom, in the presence of a base and optionally in the presence of a phase transfer catalyst; or (j) for a compound of Formula I wherein A is:

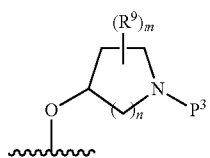

and n is 1 or 2, $P^3$ is H or (1-6C)alkyl, reacting a corresponding compound having the formula VIII

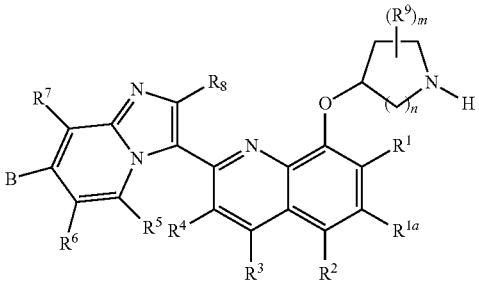

with a compound having the formula HC(O)$P^3$ where $P^3$ is H or (1-6C)alkyl, in the presence of a reducing agent; and removing any protecting group or groups and optionally forming a salt.

29. A compound of claim 1, selected from:
(R)-2-(7-(2-methoxyethoxy)imidazo[1,2-a]pyridin-3-yl)-N-(pyrrolidin-3-yl)quinolin-8-amine;
(S)-2-(7-(2-methoxyethoxy)imidazo[1,2-a]pyridin-3-yl)-N-(pyrrolidin-3-yl)quinolin-8-amine;
2-(7-(2-methoxyethoxy)imidazo[1,2-a]pyridin-3-yl)-8-(piperidin-4-yloxy)quinoline;
(R)-2-(7-(2-methoxyethoxy)imidazo[1,2-a]pyridin-3-yl)-8-(pyrrolidin-3-yloxy)quinoline;
(S)-2-(7-(2-methoxyethoxy)imidazo[1,2-a]pyridin-3-yl)-8-(pyrrolidin-3-yloxy)quinoline;
2-(7-(2-Methoxyethoxy)imidazo[1,2-a]pyridin-3-yl)-8-(2-(piperidin-2-yl)ethoxy)quinoline;
2-(7-(2-Methoxyethoxy)imidazo[1,2-a]pyridin-3-yl)-8-(piperidin-3-ylmethoxy)quinoline;
8-(8-Azabicyclo[3.2.1]octan-3-yloxy)-2-(7-(2-methoxyethoxy)imidazo[1,2-a]pyridin-3-yl)quinoline;
3-(2-(7-(2-Methoxyethoxy)imidazo[1,2-a]pyridin-3-yl)quinolin-8-yloxy)-2,2-dimethylpropan-1-amine;
(1R, 4R)-4-(2-(7-(2-Methoxyethoxy)imidazo[1,2-a]pyridin-3-yl)quinolin-8-yloxy)cyclohexanamine;
(2S,4R)-Methyl 4-(2-(7-(2-methoxyethoxy)imidazo[1,2-a]pyridin-3-yl)quinolin-8-yloxy)pyrrolidine-2-carboxylate;
(2S,4S)-Methyl 4-(2-(7-(2-methoxyethoxy)imidazo[1,2-a]pyridin-3-yl)quinolin-8-yloxy)pyrrolidine-2-carboxylate;
(S)-3-((2-(7-(2-Methoxyethoxy)imidazo[1,2-a]pyridin-3-yl)quinolin-8-yloxy)methyl)morpholine;
8-((cis)-4-fluoropyrrolidin-3-yloxy)-2-(7-(2-methoxyethoxy)imidazo[1,2-a]pyridin-3-yl)quinoline hydrochloride;
3-(2-(7-(2-methoxyethoxy)imidazo[1,2-a]pyridin-3-yl)quinolin-8-yloxy)-N,N,2,2-tetramethylpropan-1-amine;
2-((2-(7-(2-methoxyethoxy)imidazo[1,2-a]pyridin-3-yl)quinolin-8-yloxy)methyl)morpholine;
2-(7-(2-methoxyethoxy)imidazo[1,2-a]pyridin-3-yl)-8-(piperidin-4-ylmethoxy)quinoline;
7-(2-(7-(2-methoxyethoxy)imidazo[1,2-a]pyridin-3-yl)quinolin-8-yloxy)-3-oxa-9-azabicyclo[3.3.1]nonane;
8-((cis)-3-fluoropiperidin-4-yloxy)-2-(7-(2-methoxyethoxy)imidazo[1,2-a]pyridin-3-yl)quinoline;
8-((3S,4S)-3-fluoropiperidin-4-yloxy)-2-(7-(2-methoxyethoxy)imidazo[1,2-a]pyridin-3-yl)quinoline;

8-((3R,4R)-3-fluoropiperidin-4-yloxy)-2-(7-(2-methoxyethoxy)imidazo[1,2-a]pyridin-3-yl)quinoline;
(S)-2-(7-(2-methoxyethoxy)imidazo[1,2-a]pyridin-3-yl)-8-(piperidin-3-yloxy)quinoline;
(R)-2-(7-(2-methoxyethoxy)imidazo[1,2-a]pyridin-3-yl)-8-(piperidin-3-yloxy)quinoline;
(R)-2-(7-(2-methoxyethoxy)imidazo[1,2-a]pyridin-3-yl)-8-(pyrrolidin-2-ylmethoxy)quinoline;
2-(7-(2-methoxyethoxy)imidazo[1,2-a]pyridin-3-yl)-8-(pyrrolidin-3-ylmethoxy)quinoline;
5-(8-((trans)-3-fluoropiperidin-4-yloxy)-2-(7-(2-methoxyethoxy)imidazo[1,2-a]pyridin-3-yl)quinolin-4-yl)oxazole;
(trans)-4-(2-(7-(2-methoxyethoxy)imidazo[1,2-a]pyridin-3-yl)quinolin-8-yloxy)pyrrolidin-3-ol;
2-(7-(2-methoxyethoxy)imidazo[1,2-a]pyridin-3-yl)-8-((trans)-4-methoxypyrrolidin-3-yloxy)quinoline;
(trans)-4-(2-(7-(2-methoxyethoxy)imidazo[1,2-a]pyridin-3-yl)quinolin-8-yloxy)piperidin-3-01;
8-((4-fluoropiperidin-4-yl)methoxy)-2-(7-(2-methoxyethoxy)imidazo [1,2-a]pyridin-3-yl)quinoline;
(cis)-4-(2-(7-(2-methoxyethoxy)imidazo [1,2-a]pyridin-3-yl)quinolin-8-yloxy)piperidin-3-ol;
N-((cis)-3-fluoropiperidin-4-yl)-2-(7-(2-methoxyethoxy)imidazo [1,2-a]pyridin-3-yl)quinolin-8-amine;
8-((trans)-3-fluoropiperidin-4-yloxy)-2-(7-(tetrahydro-2H-pyran-4-yloxy)imidazo [1,2-a]pyridin-3-yl)quinoline;
2-(7-(cyclopropylmethoxy)imidazo[1,2-a]pyridin-3-yl)-8-((trans)-3-fluoropiperidin-4-yloxy)quinoline;
8-((trans)-3-Fluoropiperidin-4-yloxy)-2-(7-((R)-tetrahydrofuran-3-yloxy)imidazo [1,2-a]pyridin-3-yl)quinoline;
8-((trans)-3-Fluoropiperidin-4-yloxy)-2-(7-((S)-tetrahydrofuran-3-yloxy)imidazo[1,2-a]pyridin-3-yl)quinoline;
2-(2-(7-(2-methoxyethoxy)imidazo [1,2-a]pyridin-3-yl)quinolin-8-yloxy)ethanamine;
2-(7-ethylimidazo[1,2-a]pyridin-3-yl)-8-((trans)-3-fluoropiperidin-4-yloxy)quinoline;
8-((trans)-3-fluoro-1-methylpiperidin-4-yloxy)-2-(7-(2-methoxyethoxy)imidazo [1,2-a]pyridin-3-yl)quinoline;
8-((trans)-1-ethyl-3-fluoropiperidin-4-yloxy)-2-(7-(2-methoxyethoxy)imidazo [1,2-a]pyridin-3-yl)quinoline;
2-(7-(2-methoxyethoxy)imidazo [1,2-a]pyridin-3-yl)-8-(1-methylpiperidin-4-yloxy)quinoline;
8-(1-ethylpiperidin-4-yloxy)-2-(7-(2-methoxyethoxy)imidazo [1,2-a]pyridin-3-yl)quinoline;
2-(7-(2-methoxyethoxy)imidazo [1,2-a]pyridin-3-yl)-8-((1-methylpyrrolidin-3-yl)methoxy)quinoline;
2-(7-(2-methoxyethoxy)imidazo [1,2-a]pyridin-3-yl)-N-(4-methylpiperidin-4-yl)quinolin-8-amine;
8-((trans)-3-fluoropiperidin-4-yloxy)-2-(7-(pyridin-3-yl)imidazo [1,2-a]pyridin-3-yl)quinoline;
8-(piperidin-4-yloxy)-2-(7-(pyridin-3-yl)imidazo[1,2-a]pyridin-3-yl)quinoline;
8-((cis)-4-fluoropyrrolidin-3-yloxy)-2-(7-(pyridin-3-yl)imidazo[1,2-a]pyridin-3-yl)quinoline;
2-(3-(8-(trans-3-fluoropiperidin-4-yloxy)quinolin-2-yl)imidazo[1,2-a]pyridin-7-yloxy)ethanol;
6-fluoro-8-((3R,4R)-3-fluoropiperidin-4-yloxy)-2-(7-(2-methoxyethoxy)imidazo[1,2-a]pyridin-3-yl)quinoline;
8-((trans)-3-fluoropiperidin-4-yloxy)-2-(7-(pyrimidin-5-yl)imidazo[1,2-a]pyridin-3-yl)quinoline;
8-((trans)-3-fluoropiperidin-4-yloxy)-2-(7-(4-methylpyridin-3-yl)imidazo[1,2-a]pyridin-3-yl)quinoline; and
5-fluoro-8-(3R,4R)-3-fluoropiperidin-4-yloxy)-2-(7-(2-methoxyethoxy)imidazo[1,2-a]pyridin-3-yl)quinoline.

* * * * *